United States Patent
Ciaccio et al.

(10) Patent No.: US 6,236,883 B1
(45) Date of Patent: May 22, 2001

(54) METHODS AND SYSTEMS FOR LOCALIZING REENTRANT CIRCUITS FROM ELECTROGRAM FEATURES

(75) Inventors: Edward J. Ciaccio, Cherry Hill, NJ (US); Andrew L. Wit, Massapequa, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/244,549

(22) Filed: Feb. 3, 1999

(51) Int. Cl.⁷ .................................................. A61B 5/0402
(52) U.S. Cl. .......................................................... 600/515
(58) Field of Search .................................. 600/509, 515, 600/516, 517, 518

(56) References Cited

U.S. PATENT DOCUMENTS 5,609,158 * 3/1997 Chan .................................... 600/515
5,690,611 * 11/1997 Swartz et al. ......................... 600/515

OTHER PUBLICATIONS

Assadi, M., et al., (1990) "Reentrant ventricular arrhythmias in the late myocardial infarction period: 17. Correlation of activation patterns of sinus and reentrant ventricular tachycardia", *American Heart Journal* 119: 1014–1023 (Exhibit 1).

Cao, K., Gonska, B.D. (1996) "Catheter ablation of incessant ventricular *tachycardia: acute and long–term results*" *European Heart Journal* 17:756–763 (Exhibit 2).

Ciaccio, E.J. "Prediction of the Location and Time of Spontaneous Termination of Reentrant Ventricular Tachycardia for Radiofrequency Catheter Ablation Therapy" *Journal of Electrocardiology* 28:165–731 (Exhibit 3).

Ciaccio, E.J., et al. (1999) "Dynamic Changes in Electrogram Morphology at Functional Lines of Block in Reentrant Circuits During Ventricular Tachycardia in the Infarcted Canine Heart" *Journal of Cardiovascular Electrophysiology* 10:194–213 (Exhibit 4).

Fitzgerald, D.M., (1988) "Electrogram patterns predicting successful catheter ablation of ventricular tachycardia" *Circulation* 77:806–814 (Exhibit 5).

Habbab, M.A. El–Sherif, N., (1992) "Recordings from the Slow Zone of Reentry During Burst Pacing Versus Programmed Premature Stimulation for Initiation of Reentrant Coronary Artery Disease" *American Journal of Cardiology* 70:211–217 (Exhibit 6).

Llorens, JL Merino, et al. (1997) "Radiofrequency catheter ablatin of ventircular tachycardias in patients with postinfarction scars," *Revista Espanola de Cardiologia* 55(3):157–65 (Exhibit 8).

(List continued on next page.)

Primary Examiner—Scott Getzow
(74) Attorney, Agent, or Firm—John P. White; Cooper & Dunham LLP

(57) ABSTRACT

This invention provides a method comprising the steps of identifying and localizing reentrant circuits from electrogram features using feature detection and localization (FDL) algorithms. This invention provides the above method further comprising the steps of: a) using a contoured array of electrodes arranged in concentric circular patterns to obtain signals from the hearts surface to determine the direction and velocity of the activating wavefront at the catheter location; b) obtaining and preprocessing analog electrogram signals, digitizing the processed signals, and storing the digitized signals in real-time using a digital storage device; c) creating real-time maps and generating other textual information that are displayed on a computer screen, based on reentrant circuit features algorithms. This invention provides a system comprising a means for localizing reentrant circuits from electrogram features using reentrant circuit features algorithms.

157 Claims, 47 Drawing Sheets

OTHER PUBLICATIONS

Harada, T., et al., (1997) "Catheter Ablation of Ventricular Tachycardia After Myocardial Infarction: Relation of Endocardial sinus Rhythm Late Potentials to the Reentry Circuit" *Journal of American College of Cardiology* 30(4):1015–1023 (Exhibit 9).

Morad, M., et al. (1986) "An acousto–optically steered laser scanning system for measurement of action potential spread in intact heart," *Society of General Physiologists Series* 40:211–26 (Exhibit 10).

Miller, J.M. et al., (1985) "Pattern of Endocardial Activation During Sustained Ventricular Tachycardia" *Journal of the American College of Cardiology* 6(6):1280–1287 (Exhibit 10).

Morady, F., et al., (1988) "Identification and Catheter Ablation of a Zone of Slow Conduction in the Reentrant Circuit of Ventricular Tachycardia in Humans" *Journal of the American College of Cardiology* 11(4):775–782 (Exhibit 11).

Scheinman, M.M., et al., (1995) "Use of Bipolar Electrogram Characteristics and Activation Patterns During Sinus Rhythm and Ventricular Pacing to Predict the Location of Vetnricular Tachycardia Reentrant Circuits in a Canine Infarct Model" *Circulation* 92(8) (Exhibit 12).

Stevenson, W.G., et al., (1992) "Identifying sites for catheter ablation of ventricular tachycardia" *Herz*17(3)185–170 (Exhibit 13).

Stevenson,W., et al.,(1993)"Arrhythmias/Drugs:Identification of Reentry Circuit Sites During Catheter Mapping and Radiofrequency Ablation of Ventricular Tachhycardia Late After Myocardial Infarction" *Circulation* 88(4):1647–1670 (Exhibit 14).

\* cited by examiner

FIG. 2A  FIG. 2B  FIG. 2C  FIG. 2D
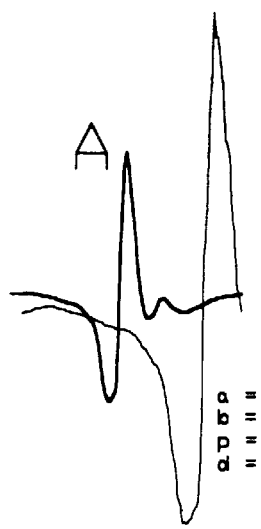
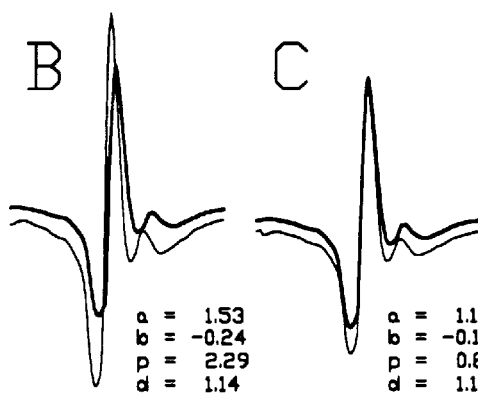
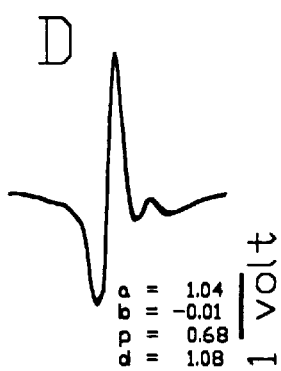
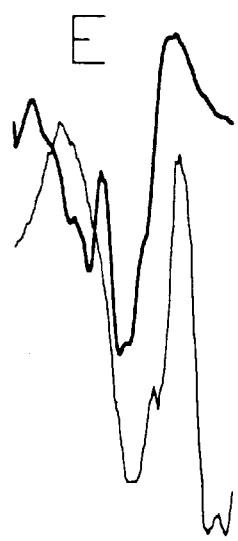
FIG. 2E  FIG. 2F  FIG. 2G  FIG. 2H

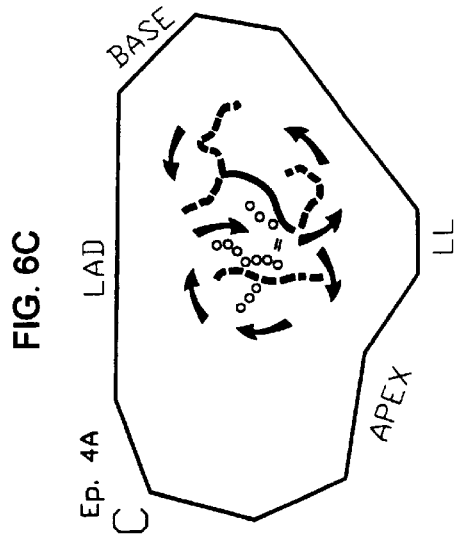
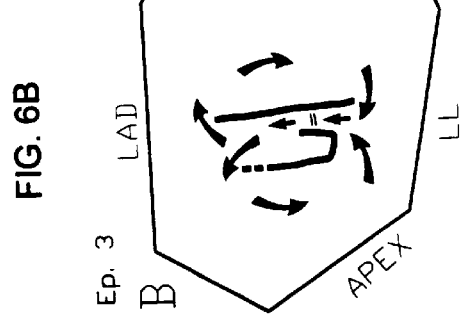
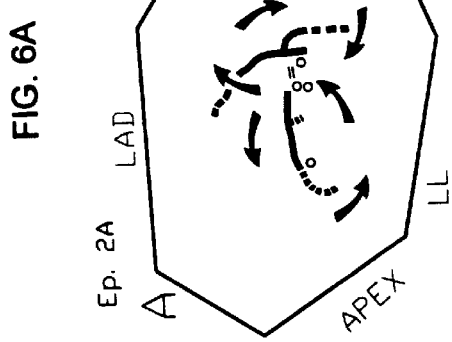
FIG. 6C
FIG. 6B
FIG. 6A

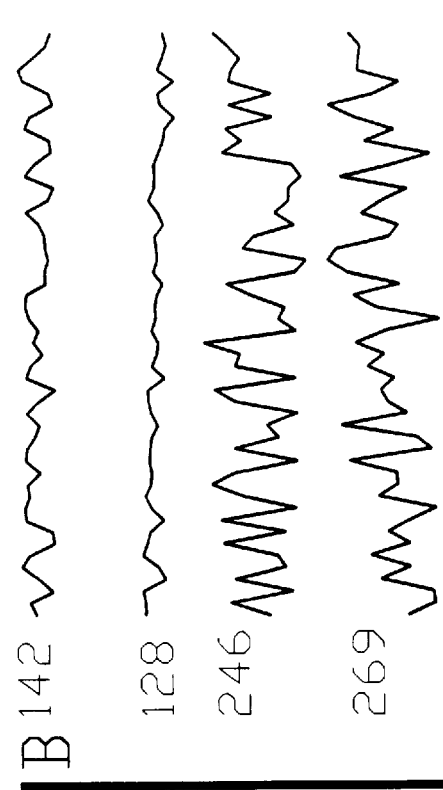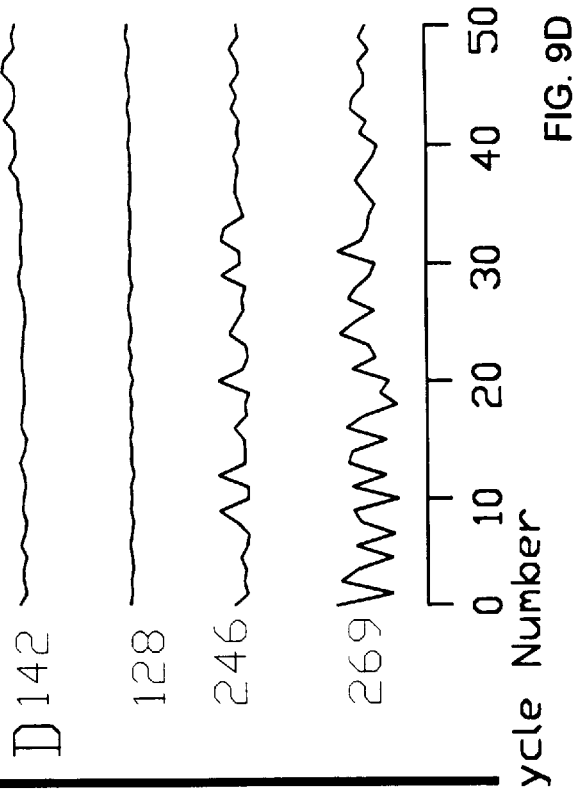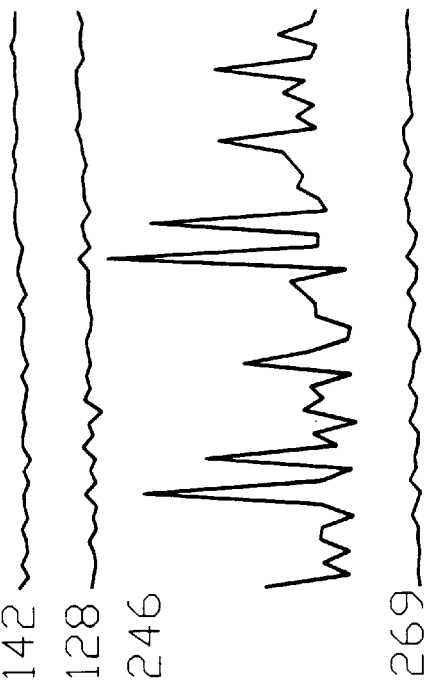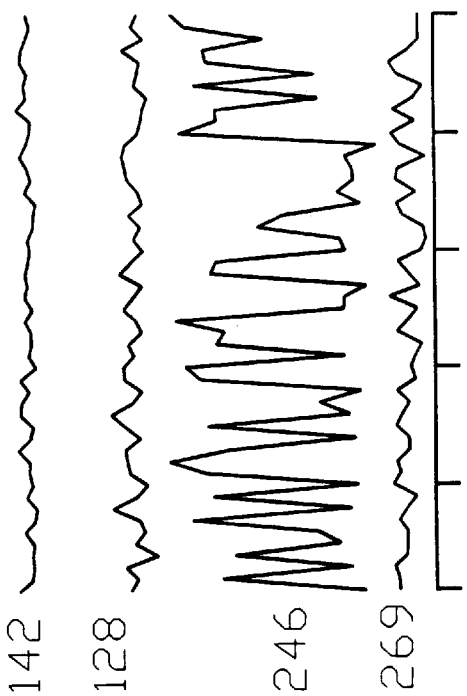

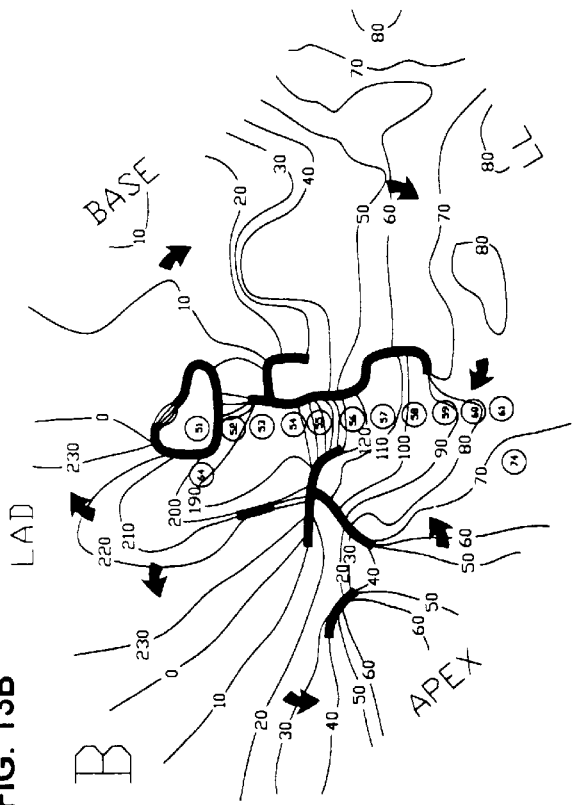
FIG. 13A
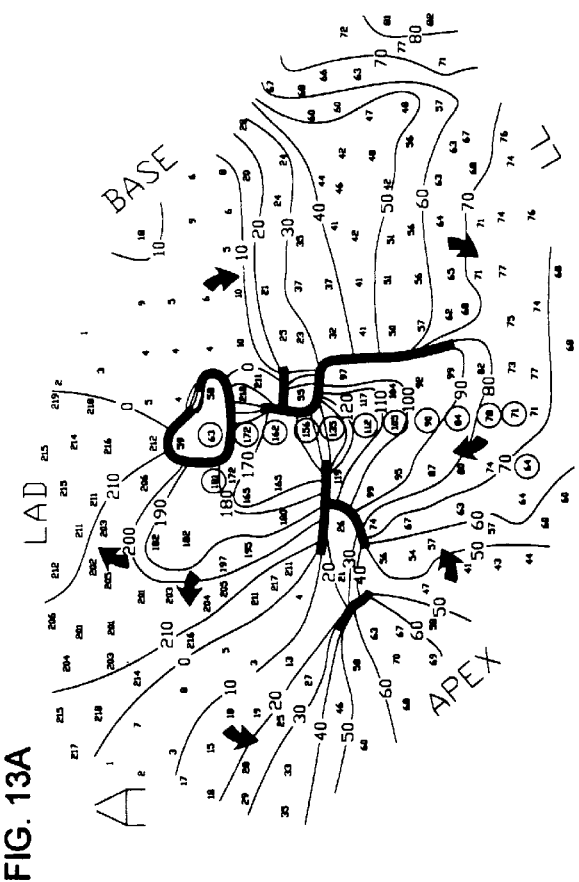
FIG. 13B
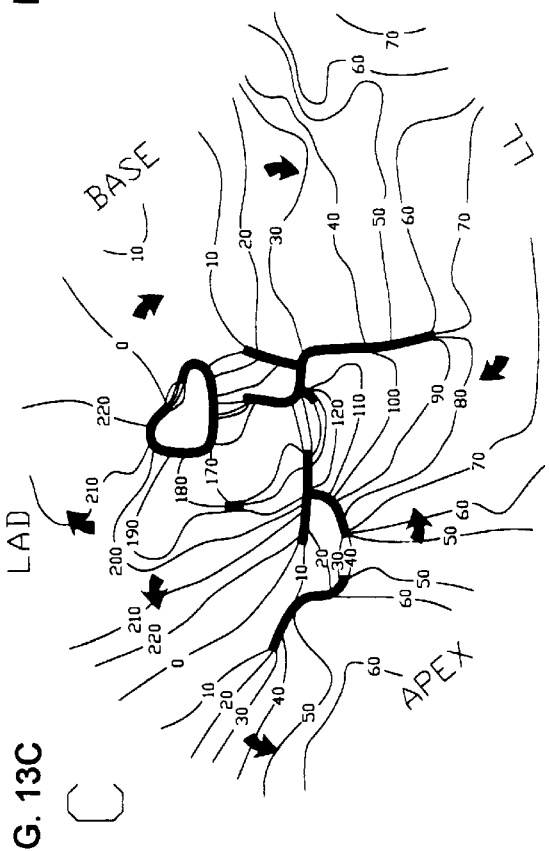
FIG. 13C
FIG. 13D

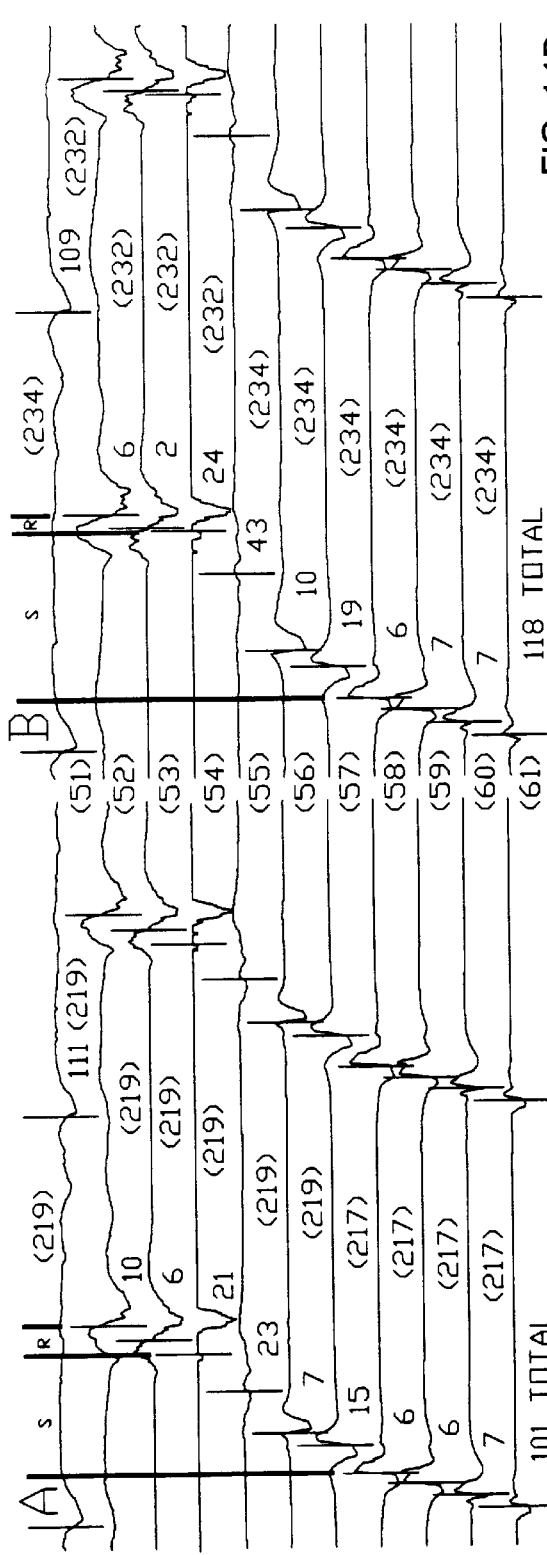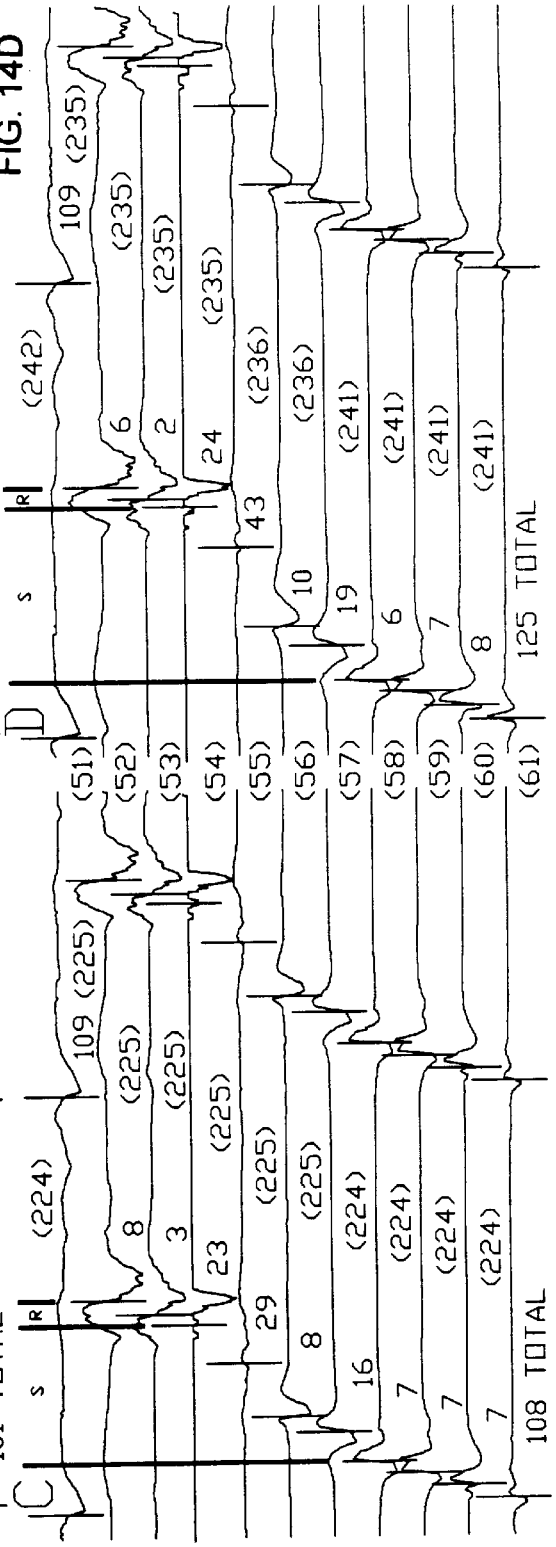
FIG. 14A  FIG. 14B  FIG. 14C  FIG. 14D

A
(51)

B
(55)

C
(74)

D
(64)

A
(51)

B
(55)

C
(74)

D
(64)

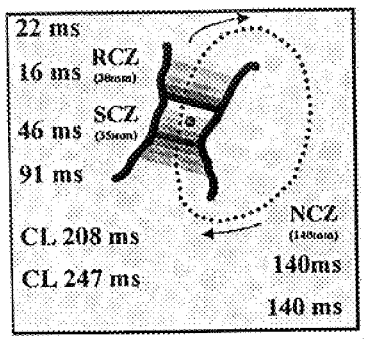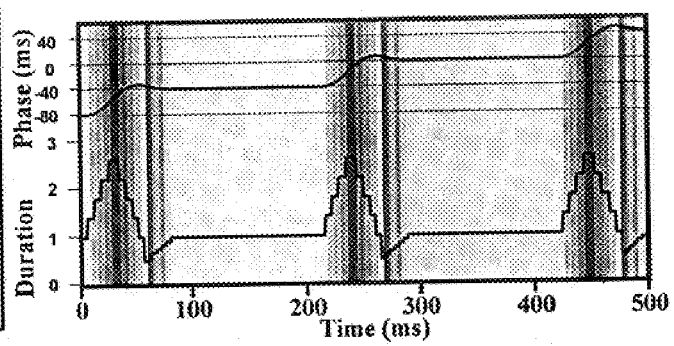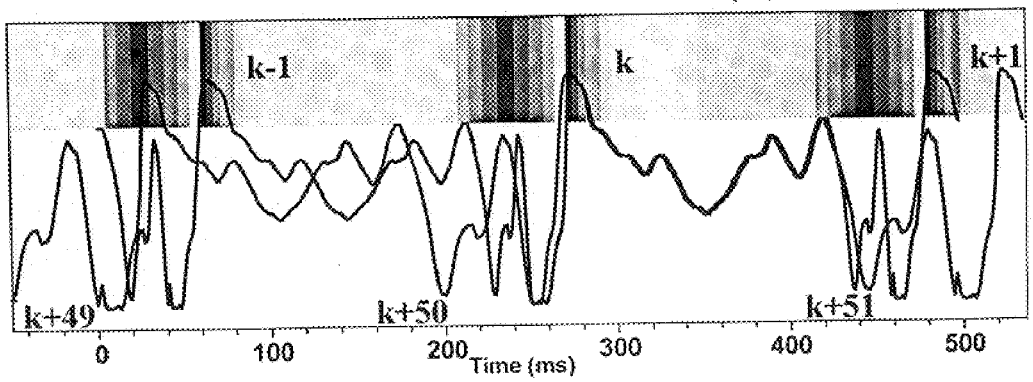

A. Sinus Rhythm

B. LAD Pacing

C. Ventricular Tachycardia

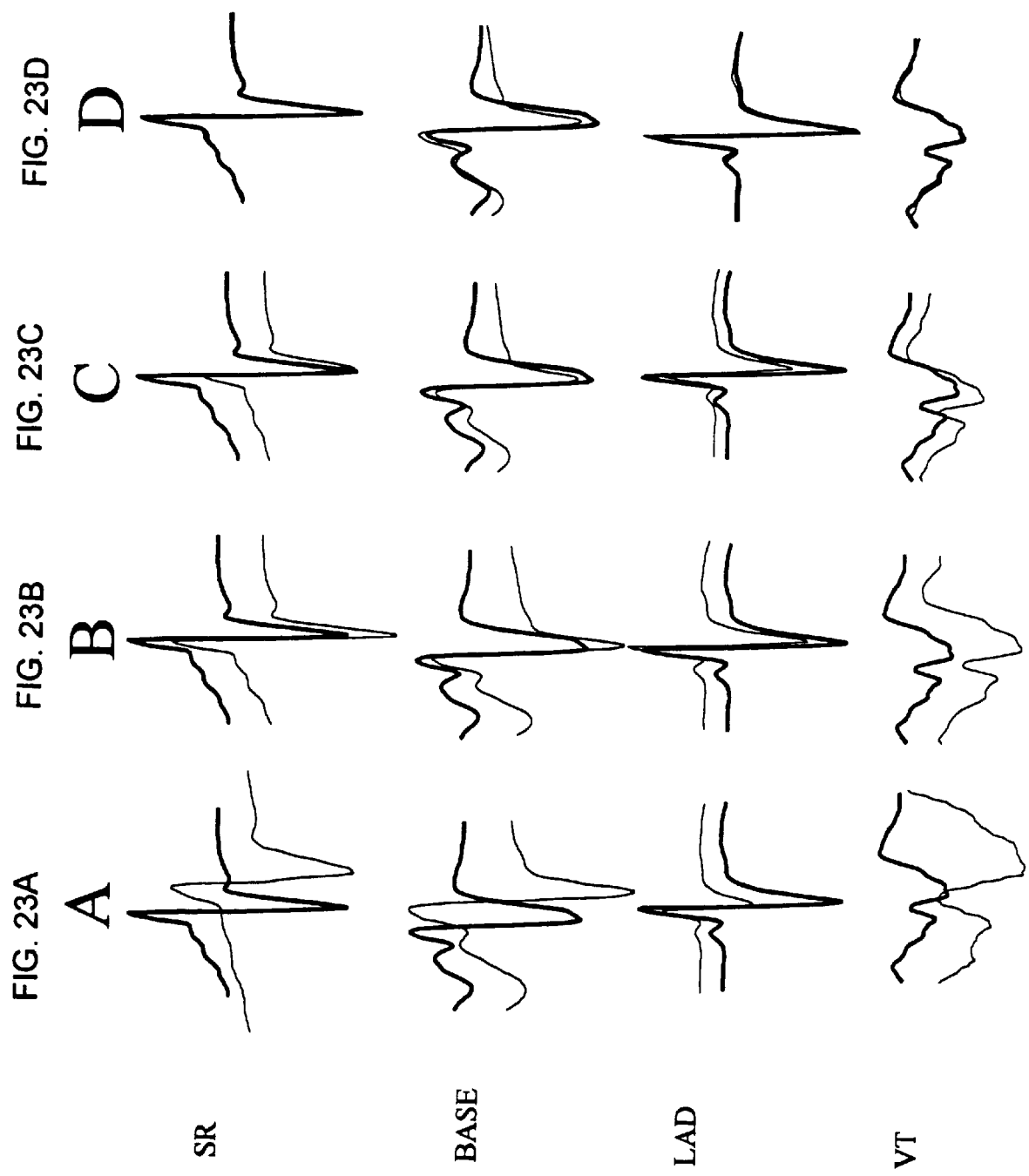

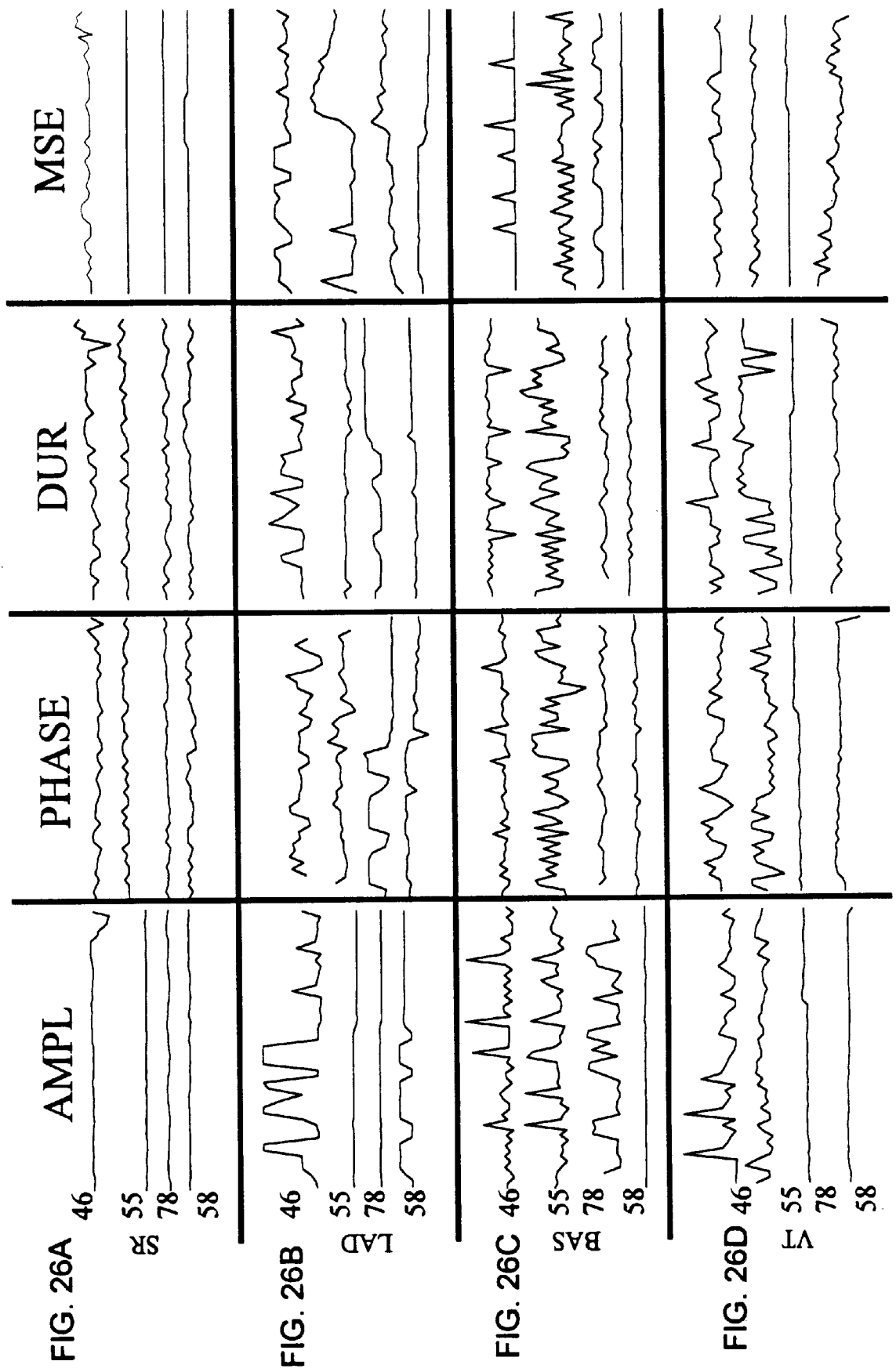

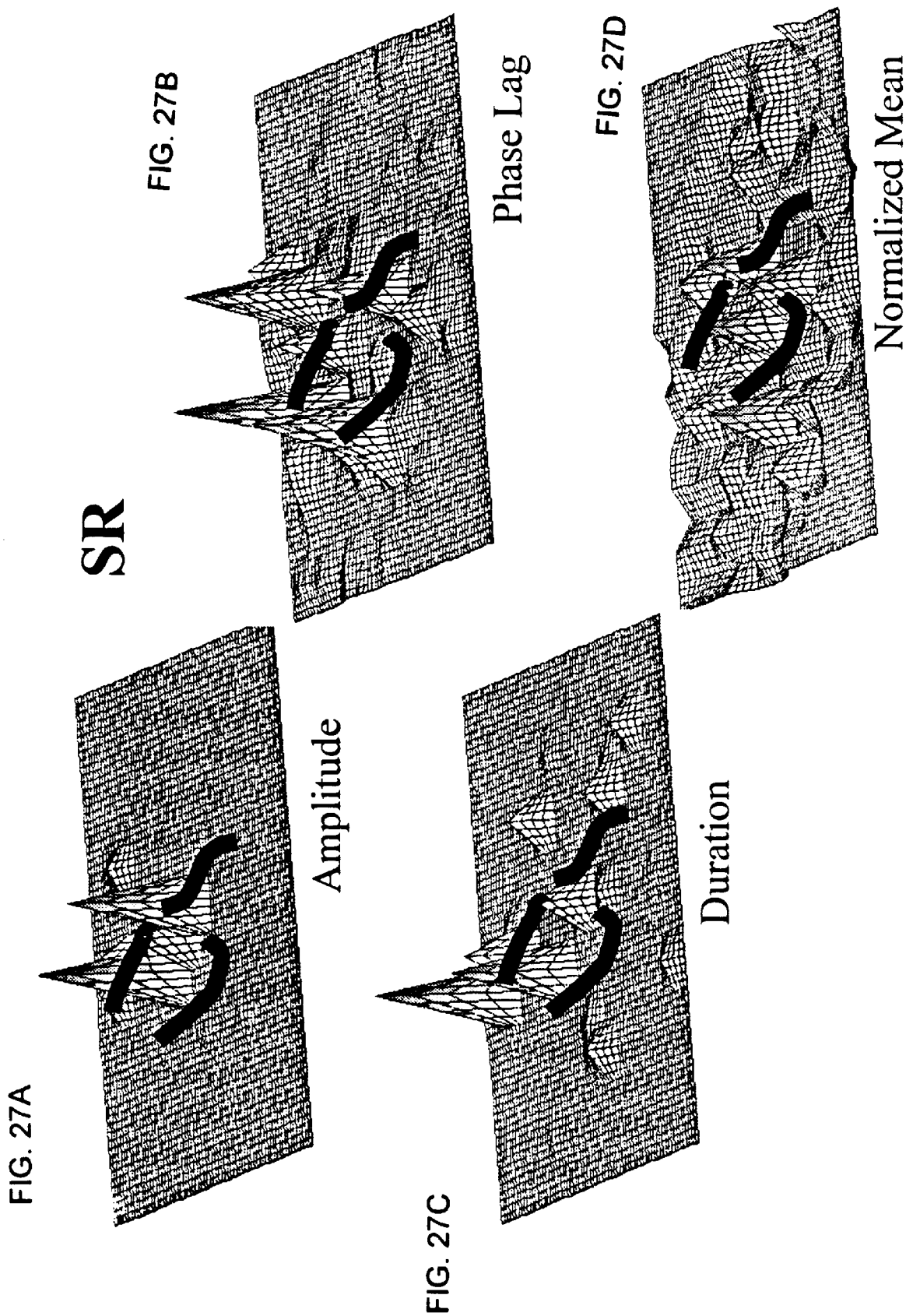
FIG. 27A Amplitude
FIG. 27B Phase Lag
FIG. 27C Duration
FIG. 27D Normalized Mean
SR

PACE (LAD)

Amplitude

Phase Lag

Duration

Normalized Mean

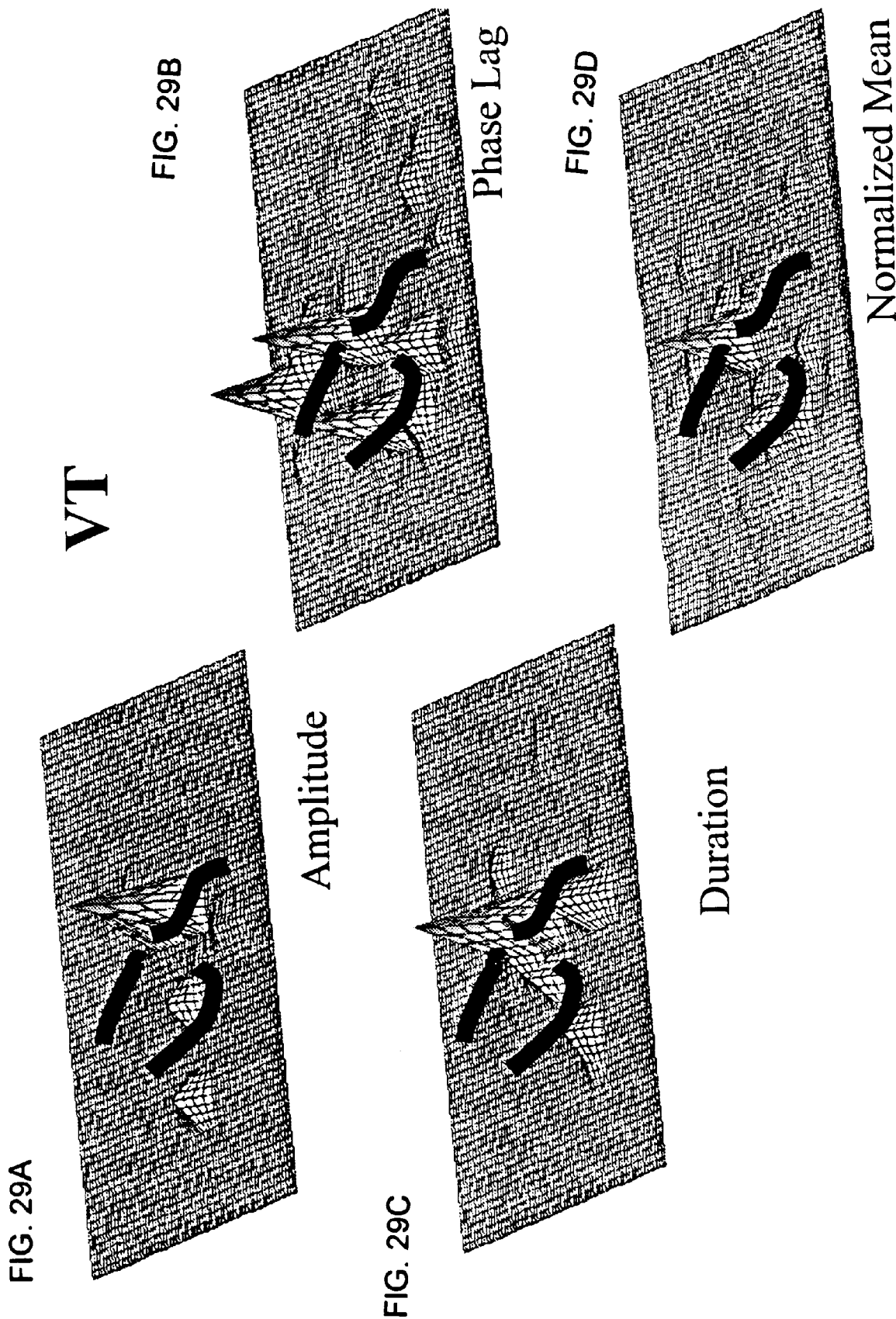
FIG. 29A Amplitude
FIG. 29B Phase Lag
FIG. 29C Duration
FIG. 29D Normalized Mean
VT

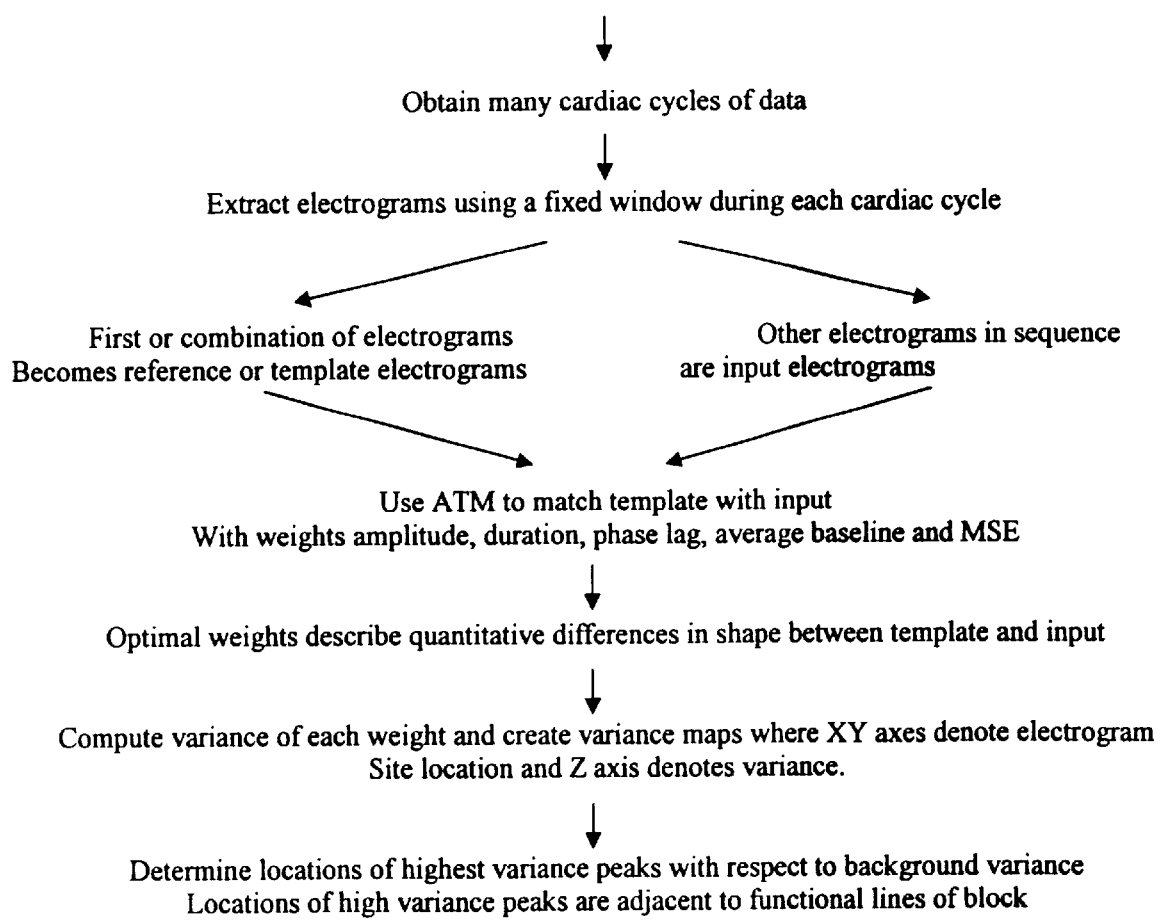

FIG. 31

ATM
(linear adaptive template matching)

Obtain many cardiac cycles of data

Extract electrograms using a fixed window during each cardiac cycle

First or combination of electrograms
Becomes reference or template electrograms

Other electrograms in sequence
are input electrograms

Use ATM to match template with input
With weights amplitude, duration, phase lag, average baseline and MSE Optimal weights describe quantitative differences in shape between template and input Compute variance of each weight and create variance maps where XY axes denote electrogram
Site location and Z axis denotes variance.

Determine locations of highest variance peaks with respect to background variance
Locations of high variance peaks are adjacent to functional lines of block

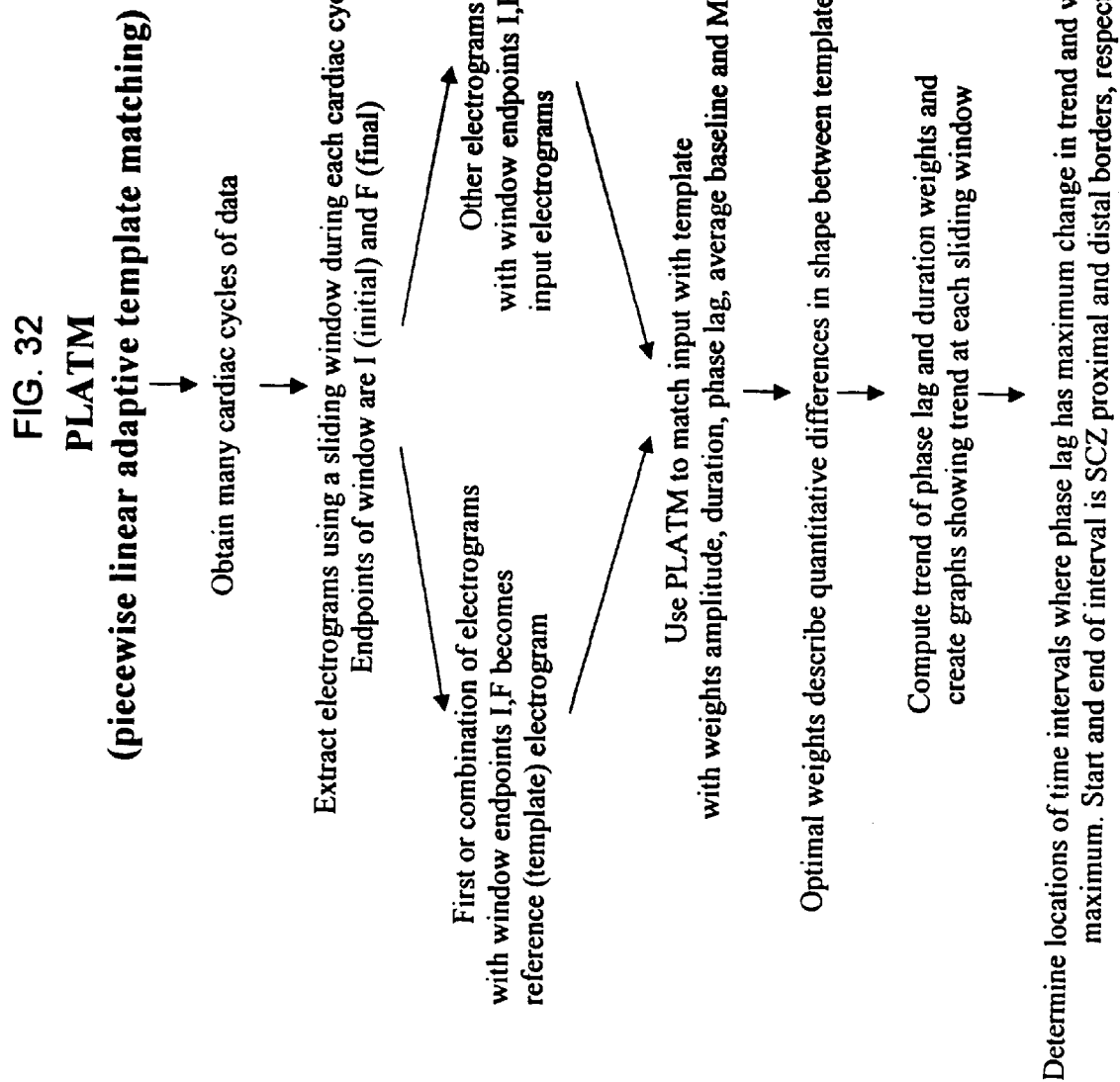

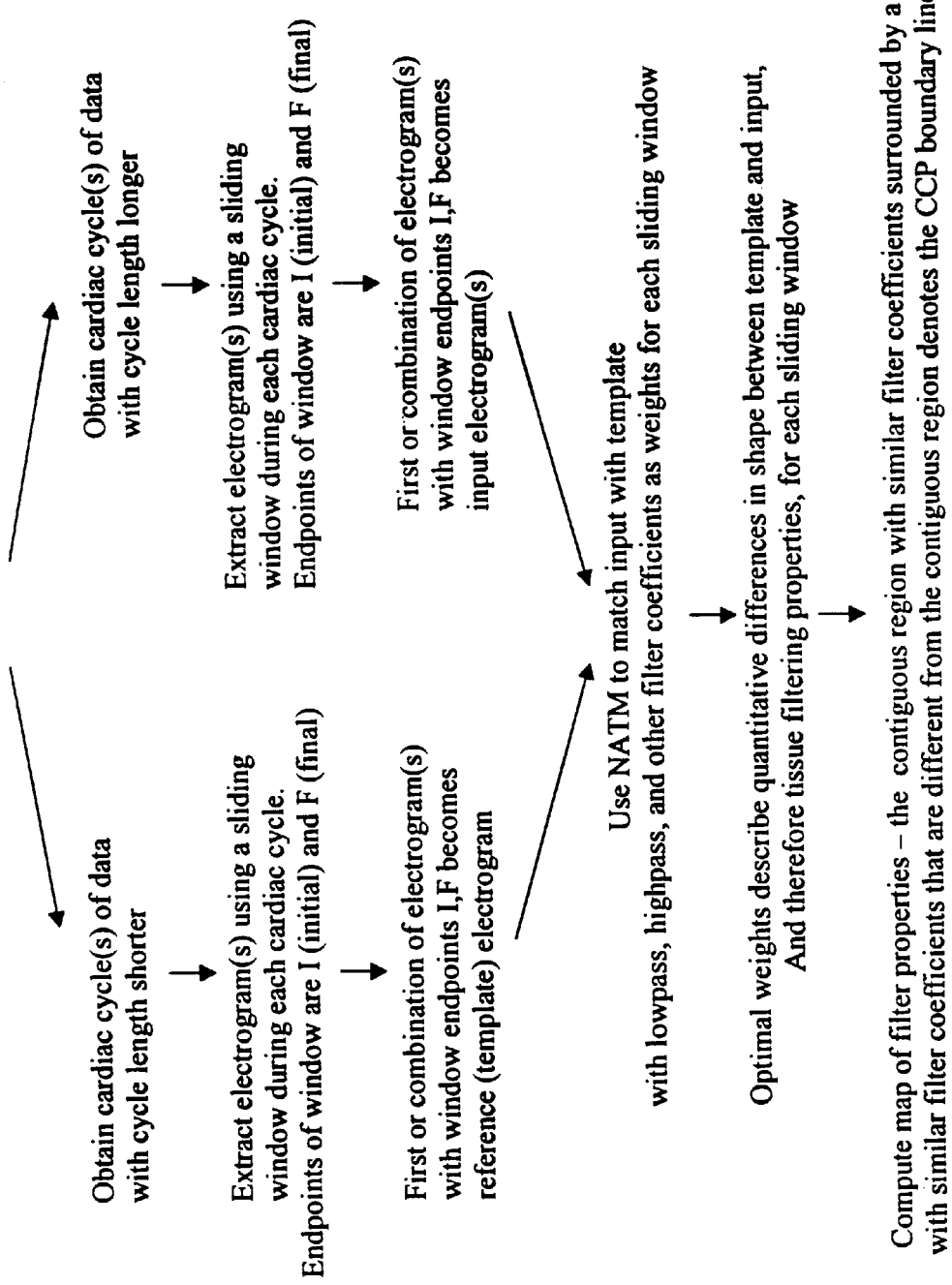

Device

FIG. 37A
FLOW OF PROCEDURE

| Subsystem | Instruction | Algorithm |
|---|---|---|
| 1. | Position catheter<br>Hold Position | |
| 2.<br>3. | Obtain Signals, multiplex, and store<br>Determine conduction velocity | CV |
| 3. | Determine if site is at block line<br>(i.e., is variance higher than surrounds<br>based on a threshold) | ATM |
| 3. | Determine activation time differences<br>from Catheter to slow conduction zone<br>Use model to convert times to distances | PLATM |
| 3. | Obtain electrograms at short and long<br>cycle lengths<br>Compute filter coefficients and determine<br>Time of activation of CCP | NATM |
| 3. | Compute distance from catheter tip to CCP<br>Determine difference in activation<br>Times that is a maximum divided by<br>Distance is conduction velocity. | CM |

FIG. 37B

FLOW OF PROCEDURE – CONTINUED

| Subsystem | Instruction | Algorithm |
|---|---|---|
| 4. | Compute new map based on information at site<br>Display information on screen<br>Based on FDL algorithms quantitative information, arrow is shown on screen.<br>Tail of arrow is catheter tip location.<br>Direction and magnitude in which catheter tip is to traverse are given by head of arrow. | |
| 4. | Strategies:<br>A. Follow circuit around a functional line of block until arrive at slow conduction zone.<br>(less location update error but more time consuming)<br>B. Cut across a functional line of block until arrive at slow conduction zone.<br>(more location update error but less time consuming) | |

3. DETAILS OF DISPLAY/GUIDANCE SUBSYSTEM

METHODS AND SYSTEMS FOR LOCALIZING REENTRANT CIRCUITS FROM ELECTROGRAM FEATURES

The invention disclosed herein was made from Government support under Grant R37 HL-31393 and Project Grant HL-30557 from the Heart, Lung and Blood Institutes, National Institutes of Health, and a Research Grant from the Whitaker Foundation. Accordingly, the U.S. Government has certain rights in this invention.

Throughout this invention, various publications may be referenced by Arabic numerals in brackets. Disclosures of these publications in their entireties are hereby incorporated by reference into this application to more fully describe the state of the art to which this invention pertains. Full citations for these publications may be found at the end of the specification.

BACKGROUND OF THE INVENTION

A great deal of information is present in extracellular electrogram morphology about the physiology of conduction of the cardiac impulse (1–4). For this reason, the characteristics of electrograms in reentrant circuits are of interest and have been investigated because they might provide information on mechanisms of slow conduction and block that cause reentry. Particular attention has been paid to the occurrence, location and causes of low amplitude or long duration potentials, double potentials and fractionated electrograms (5–13). In addition, it has been reasoned that if electrogram characteristics in reentrant circuits are specific they might provide an easy and rapid means for locating those circuits without complete activation mapping (12–14). This might facilitate ablation of such circuits with surgical or catheter techniques (12–15). However, specific electrogram characteristics in reentrant circuits have not yet been identified.

The analysis of electrogram morphology in reentrant circuits has only been done for individual complexes. It has not been determined whether there are special and specific dynamic electrogram characteristics, that is, beat-to-beat changes in electrogram shape during the course of tachycardia. We have shown that large dynamic changes in electrogram morphology as quantified by an adaptive template matching technique (16) occur specifically at functional lines of conduction block that bound the central common pathway of figure of eight reentrant circuits (17), in a canine model of ventricular tachycardia. This characteristic provides information about possible mechanisms for block, as well as suggesting that this methodology might be applied to the localization of some ventricular reentrant circuits causing clinical tachycardia. A preliminary report has also been published in abstract form (18).

SUMMARY OF THE INVENTION

This invention provides a method comprising the steps of identifying and localizing reentrant circuits from electrogram features using feature detection and localization (FDL) algorithms.

This invention provides the above method further comprising the steps of:
a) using a contoured array of electrodes arranged in concentric circular patterns to obtain signals from the hearts surface to determine the direction and velocity of the activating wavefront at the catheter location;
b) obtaining and preprocessing analog electrogram signals and multiplexing and storing the signals, in analog or digital form;
c) creating real-time maps and generating other textual information that are displayed on a computer screen, based on reentrant circuit features algorithms.

This invention provides the above method for quantifying dynamic, beat-to-beat changes in electrogram morphology.

As used herein, "dynamic, beat-to-beat changes" means the differences in electrogram shape which occur over the course of two or more cardiac cycles.

This invention provides the above method, wherein signal segments are adaptively matched for best overlap.

This invention provides the above method for quantifying the linear parameter of electrogram shape. One embodiment of the linear parameter is scale. One embodiment of the scale is amplitude. Another embodiment of the scale is duration. Another embodiment of the linear parameter is shift. One embodiment of the shift is phase lag. Another embodiment of the shift is the average baseline.

This invention provides the above method for quantifying the piecewise linear parameter of electrogram shape. In one embodiment the piecewise linear parameter is scale. In one embodiment the scale is amplitude. In another embodiment the scale is duration. In another embodiment the piecewise linear parameter is shift. In one embodiment of the above method, the shift is average baseline. In another embodiment of the above method, the shift is phaselag.

This invention provides a method of quantifying non-linear parameters of electrogram shape. In one embodiment the non-linear parameters are the low pass filter coefficients. In another embodiment the non-linear parameters are the high pass filter coefficients. In another embodiment the non-linear parameters are the notch pass filter coefficients. In another embodiment the non-linear parameters are the band-pass pass filter coefficients. In another embodiment the non-linear parameters are the exponential or other nonlinear coefficients.

This invention provides the above method which uses the mean square error criterion or other criteria for adaptation of weights. In one embodiment, the mean square error measures cycle-to-cycle changes in intrinsic electrogram shape.

This invention provides the above method wherein each electrogram on each cardiac cycle is compared to a reference electrogram or template electrogram. In one embodiment, the reference or template electrogram is obtained from a representative cycle. In another embodiment, the reference or template electrogram is obtained from an average of multiple cycles. In another embodiment, the above method is used to obtain information about changes which occur in electrogram morphology over multiple cardiac cycles from one cardiac cycle to the next.

In one embodiment, the above method uses the differential steepest descent method or other adaptive method to compute the weight update.

In one embodiment, the magnitude and direction for weight adjustment are determined by calculating a derivative or other function of the error based on finite difference changes or other changes in the weighting. In one embodiment, a method is used to minimize the misadjustment of the weight update. In one embodiment, the convergence coefficient is optimized in order to minimize the misadjustment of the weight update. In one embodiment, the convergence coefficient is incremented up or down in order to minimize the mean square error or other error for function during weight update.

In one embodiment, the length of segment is maximized to minimize the misadjustment of the weight update. The maximum length can range of 50 to 1000 milliseconds.

This invention provides the above method wherein the finite difference is optimized to minimize the misadjustment of the weight update. In one embodiment, the finite difference is incremented to minimize the mean square error or other error function during weight update.

In one embodiment of the above method, functional lines of block in reentrant circuits are located by analyzing ATM algorithms. In one embodiment, the data is obtained during sustained monomorphic ventricular tachycardia.

As used herein, "ventricular tachycardia" means an abnormal heart rhythm in which the heart beats more rapidly than normal, which can be caused by a reentrant circuit.

In another embodiment of the above method, functional lines of block in reentrant circuits can be located by analyzing ATM variances or other weight variabilities from data obtained during unsustained monomorphic ventricular tachycardia.

In another embodiment of the above method, functional lines of block in reentrant circuits can be located by analyzing ATM variances or other weight variabilities from data obtained during polymorphic ventricular tachycardia.

In another embodiment of the above method, functional lines of block in reentrant circuits can be located by analyzing ATM variances or other weight variabilities from data obtained during sinus rhythm.

As used herein, "sinus rhythm" means the normal rhythm of the heart in which the regular beating of the heart initiates in a specialized heart cell in a region of the heart called the sinoatrial node.

In another embodiment of the above method, functional lines of block in reentrant circuits can be located by analyzing ATM variances or other weight variabilities from data obtained during ventricular pacing during sinus rhythm.

In another embodiment of the above method, functional lines of block in reentrant circuits can be located by analyzing ATM variances or other weight variabilities from data obtained during pacing during ventricular tachycardia.

In one embodiment of the above methods, the analysis is performed by computer processing.

This invention provides the above method wherein the regions of greatest variance of ATM parameters are adjacent to the location of functional lines of block that formed the boundaries of the central common pathway in reentrant circuits. In one embodiment, an average of variances for sites with low variance is used as a threshold.

In one embodiment, the above method is used to locate reentrant circuits for localized drug intervention, surgical incision or catheter ablation in a subject. In one embodiment, the subject is one with ventricular tachycardia.

In one embodiment of the above method, functional reentrant circuits and functional lines of block that bound the central common pathway can be located for catheter abalation of ventricular tachycardia without the necessity for recording from a large number of sites and without constructing activation maps.

In one embodiment, the region of greatest increase of the PLATM duration parameter when tachycardia cycle length increases resides at the location where slow conduction occurs in the central common pathway of a reentrant circuit. In another embodiment, the region of greatest decrease of PLATM duration parameter when tachycardia cycle length decreases resides at the location where slow conduction occurs in the central common pathway of a reentrant circuit.

In one embodiment, the method updates the location of an ablation catheter based on far-field electrogram deflections.

In one embodiment of the above method, the PLATM phase shift parameter is used to determine the time of activation of the zone of slow conduction with respect to the local activation time at the position of the catheter.

In one embodiment a model is used to convert the direction and time into a distance from the current position of the catheter to the zone of slow conduction.

In one embodiment, the PLATM duration parameter is used to determine the time of activation of the zone of slow conduction with respect to the current position of the catheter. In one embodiment, a model is used to convert the direction and time into a distance from the current position of the catheter to the zone of slow conduction.

In one embodiment of the above method, the catheter tip location can be directed toward the location of the optimal site to ablate the heart based on the distance from the catheter tip to the slow conduction zone (SCZ) proximal and distal borders.

In another embodiment, the slow conduction zone can be located by analyzing ATM variances or other weight variabilities from data obtained during unsustained monomorphic ventricular tachycardia.

In another embodiment, functional lines of block in reentrant circuits can be located by analyzing ATM variances or other weight variabilities from data obtained during polymorphic ventricular tachycardia.

In another embodiment, functional lines of block in reentrant circuits can be located by analyzing ATM variances or other weight variabilities from data obtained during sinus rhythm.

In another embodiment, functional lines of block in reentrant circuits can be located by analyzing ATM variances or other weight variabilities from data obtained during ventricular pacing during sinus rhythm.

In another embodiment, functional lines of block in reentrant circuits can be located by analyzing ATM variances or other weight variabilities from data obtained during pacing during ventricular tachycardia.

In another embodiment, the analysis is performed by computer processing.

The NATM algorithm will be used to determine the location of the entrance and exit boundaries of the CCP and therefore the lengths of the block lines bounding the CCP. The principle is as follows. As tachycardia cycle length changes, the electrogram shapes will change slightly depending on the filtering characteristics of the tissue. Previous work done in our laboratory has shown that these characteristics differ within the CCP versus outside the CCP. The properties of gap junctions (connecting channels between heart cells) differ within versus outside the CCP, and these differing properties will cause the tissue filtering characteristics to change in each area. The NATM parameters (filter coefficients such as time constants for low, high, and band pass filtering, notch filtering and other filtering) will differ within versus outside the CCP and these parameters are measurable when there is a change in cycle length. By using NATM in a piecewise linear mode to quantify far-field electrogram deflections, the time difference from local activation at the CCP entrance and exit boundaries can be ascertained from a single site. Based on a mathematical model, this time difference is converted into a physical distance that will provide the distance from the catheter tip to the CCP entrance and exit borders, and therefore the length of the block lines bounding the CCP.

This invention provides the above methods wherein the Nonlinear Adaptive Template Matching (NATM) algorithm filter coefficients are used to distinguish activation occurring inside of the CCP from activation occurring outside of the CCP.

In one embodiment of the above method, waveforms are compared at different cycle lengths to determine changes in NATM filter coefficients.

The invention also provides the above method which updates the location of an ablation catheter based on electrogram far-field directions.

In one embodiment, the catheter tip location can be directed toward the location of the optimal site to ablate the heart based on the distance from the catheter tip to the CCP entrance and exit.

In one embodiment, NATM filter coefficients change when cycle length changes and can be used to determine the time of activation of the borders at the entrance and at the exit of the CCP with regard to local activation time at the portion of the catheter.

In one embodiment of the above method, NATM filter coefficients change when cycle length changes and can be used to detect the border at the entrance and at the exit of the CCP.

In one embodiment of the above method, a model can be used to determine the distance from the local site to the entrance and to the exit of the CCP.

In one embodiment of the above method, the length of the CCP and the length of the bounding block lines can be determined based on the distances from the catheter tip to the CCP entrance and exit.

In one embodiment of the above method, the NATM filter coefficients can be determined at sites of distant electrical activity by quantification of electrogram far-field deflections.

In one embodiment of the above method, the catheter tip location can be directed toward the location of the optimal site to ablate the heart based on the distance from the catheter tip to the CCP entrance and exit.

This invention also provides the above method, wherein the length of the CCP and the length of the bounding block lines can be determined by analyzing ATM variances or other weight variabilities from data obtained during sustained monomorphic ventricular tachycardia.

In one embodiment, the length of the CCP and the length of the bounding block lines can be determined by analyzing ATM variances or other weight variabilities from data obtained during unsustained monomorphic ventricular tachycardia. In another embodiment, the length of the CCP and the length of the bounding block lines can be determined by analyzing ATM variances or other weight variabilities from data obtained during polymorphic ventricular tachycardia. In another embodiment, the length of the CCP and the length of the bounding block lines can be determined by analyzing ATM variances or other weight variabilities from data obtained during sinus rhythm. In another embodiment, the length of the CCP and the length of the bounding block lines can be determined by analyzing ATM variances or other weight variabilities from data obtained during ventricular pacing during sinus rhythm. In another embodiment, the length of the CCP and the length of the bounding block lines can be determined by analyzing ATM variances or other weight variabilities from data obtained during pacing during ventricular tachycardia.

The conduction velocity (CV) algorithm is used to determine the speed and direction of the activating wavefront at the location of the catheter tip. Based on the activation times at the concentric rings electrodes, the speed and direction of the wavefront is computed based on the maximum, average, median, quartile, or other statistical time difference in activation of any two or more electrodes.

This invention provides the above method wherein a concentric circular multielectrode ring and conduction velocity algorithms are used to determine wavefront speed and direction at the location of the catheter tip.

In one embodiment of the above method, the direction of the wavefront is calculated based on the maximum or average maximum difference in the activation times of any two or more electrodes.

In one embodiment of the above method, the direction of the block lines with respect to the catheter tip will lie perpendicular to the direction of the wavefront when the catheter resides within the CCP at the SCZ.

In one embodiment of the above method, the conduction velocity of the activating wavefront is determined by dividing the maximum or average maximum difference in the activation times of any two or more electrodes into the distance between those same electrodes.

As used herein, "maximum difference in the activation time" means for a given set of activation times at 2 or more sites occurring during cardiac cycle, two sites or average of multiple sites with activating times which are the most disparate.

The center of mass (CM) algorithm will be used to determine the location of the narrowest width of the CCP based on ATM weight variability peaks. Once the variance peaks are obtained using the ATM algorithm, the position of the narrowest width of the CCP can be approximated as the center of mass of the highest variance peaks (highest 4–400 of 5–500 total sites). In another embodiment, any number of peaks from 5–500 may be used for CM calculations and they need not include only the highest variance peaks. Our observations show that the narrowest width of the CCP resides within the SCZ of the CCP. Therefore, this measurement is both a pointer to the position of the SCZ, and also determines the position of the narrowest width of the CCP that resides within the SCZ. In human studies, it has been shown that the SCZ is the best place to ablate the heart to stop tachycardia. By ablating not only within the SCZ but at the narrowest CCP width, the length of the ablation lesion needed to interrupt the reentrant circuit and stop tachycardia will be minimized. This minimizes the chance that the heart will be harmed by the procedure during creation of the ablation lesion.

This invention provides the above method wherein the center of the narrowest width of the CCP of reentrant circuits is determined using 5–500 ATM weight variability peaks.

In one embodiment of the above method, the center of mass (CM) of the highest 5–400 variance peaks is determined to approximate the center of the narrowest CCP width location.

In one embodiment of the above method, the CM of an average of all 5–500 variance peaks from highest to lowest is determined to approximate the center of the narrowest CCP width location.

This invention provides the above method, wherein ablation of the central common pathway between lines of functional block at the zone of slow conduction prevents tachycardia.

In one embodiment of the above invention, ablation of the central common pathway between lines of functional block at the zone of slow conduction prevents tachycardia.

This invention provides the above method for ablating the heart to stop ventricular tachycardia when the lines of block around which the activating wavefront traverses are anatomical, partly anatomical and partly functional, or wholly functional.

This invention provides the above method for ablating the heart to stop ventricular tachycardia when the pattern of reentry is intramural or transmural.

This invention provides the above method for pinpointing sites or specific areas for drug delivery.

This invention provides the above method for detecting and localizing pathologic conditions in but not limited to the heart, brain, lung, gastrointestinal system and musculoskeletal systems.

This invention provides a system comprising a means for localizing reentrant circuits from electrogram features using features detection and localization (FDL) algorithms.

This invention provides the above system comprising a device which comprises:

a) A multipolar ring catheter which uses a contoured array of electrodes arranged in concentric circular patterns to obtain signals from the heart's surface for the purpose of determining the speed and direction of the activating wavefront at the catheter location;

b) a data acquisition subsystem used to obtain and pre-process analog electrogram signals, and to multiplex and store the signals in real time, in analog or digital form;

c) a processing unit comprising software and hardware for multiple electrodes, and features detection and localization algorithms; and d) a display/guidance subsystem which creates a real-time map that is displayed on a computer screen, based on features detection and localization algorithms.

This invention provides the above system wherein the multipolar catheter ring comprises electrodes attached to thin, shielded, insulated wires at the catheter tip for recording electrogram signals and for ablating the heart from any of the electrodes.

This invention provides the above system wherein the multipolar catheter ring comprises a configuration of electrodes in a circular pattern at the catheter tip for the purpose of recording electrogram signals and also ablating the heart with radiofrequency or other energy.

This invention provides the above system wherein the multipolar catheter ring comprises a conical-shaped or similarly-shaped electrode array with fan-like or other folding action, that is initially compactly folded when traveling within the confines of a human artery, but which opens into a conical-shape when positioned within a ventricular cavity of the heart so as to fit the contour of the heart.

This invention provides the above system, wherein the multipolar catheter ring comprises a thin, tough, flexible catheter shell that contains the wires used to record electrograms and to ablate the heart.

This invention provides the above system, wherein the multipolar catheter ring comprises a terminal mount that is used to rapidly connect/disconnect the catheter at its proximal end to the data acquisition subsystem.

This invention provides the above system, wherein the data acquisition subsystem comprises circuitry to amplify the signals to reduce noise pickup.

This invention provides the above system, wherein the data acquisition subsystem comprises circuitry used to low pass filter the signals to remove high frequency noise and to prevent aliasing during the digitization process.

This invention provides the above system, wherein the data acquisition subsystem comprises circuitry used to high pass filter the signals to remove motion artifacts and to prevent the buildup of bias voltage.

This invention provides the above system, wherein the data acquisition subsystem comprises circuitry to multiplex and store the signals, in analog or digital form.

This invention provides the above system, wherein the data acquisition subsystem comprises the use of the difference or other function integrated circuit to determine the speed and direction of the activating wavefront with respect to the multipolar ring catheter.

This invention provides the above system, wherein the data acquisition subsystem comprises the use of a maximum or maximum averaging function integrated circuit to determine which pair or set of electrodes of the multipolar ring catheter lies parallel to the direction of propagation of the activating wavefront.

This invention provides the above system, wherein the processing unit comprises software and hardware for multipole electrodes and features detection and localization algorithms. In one embodiment, the algorithms are hardwired using analog circuitry. In another embodiment, the algorithms are hardwired using integrated circuits for features detection and localization serial or parallel processing. In another embodiment, the algorithms are downloaded to programmable logic array (PLA) integrated circuits or similar device for serial or parallel processing. In a further embodiment, the algorithms are written in software code for serial or parallel processing using a microprocessor or parallel processing using multiple microprocessors.

This invention provides the above system, wherein the display/guidance subsystem displays the conduction velocity and directional information determined based on electrogram signals obtained from the multipolar electrode.

This invention provides the above system, wherein the direction of the slow conduction zone, and the distance to the proximal and distal edges of the slow conduction zone with respect to catheter location is determined based on measurements made using the PLATM algorithm.

This invention provides the above system, wherein the location of block lines is determined based on measurements made using the ATM algorithm.

This invention provides the above system, wherein the location of the entrance and exit to the central common pathway and the length of the block lines bounding the central common pathway is determined based on measurements made using the NATM algorithm.

This invention provides the above system for locating the narrowed width of the central common pathway based on the center of mass algorithm.

This invention provides the above system comprising a system of symbols such as shaded and textured shapes to denote features of the reentrant circuit on the real-time display map.

This invention provides the above system comprising a system of symbols such as arrows and angles used to denote distance and directional information pertaining to the location of reentrant circuit features with respect to the location of the catheter on the real-time display map.

BRIEF DESCRIPTION OF THE FIGURES

FIGS. 2A–2H Panels A–D show an example of adaptive template matching (ATM) of an input signal (thin trace) to the template (thick trace) when the intrinsic shapes of the signals are similar (electrogram at site 58 in FIG. 1). Panel A is prior to matching with arbitrary initial weighting of the input signal. Panel B is after 5 iterations of weight updates, Panel C after 25 iterations and Panel D after 500 iterations. Panels E–H show ATM of an input signal (thin trace) and a template (thick trace) when the intrinsic shapes are different (electrogram at site 55 in FIG. 1). Panel E is prior to matching, with arbitrary initial weighting of the input signal, Panel F is after 5 iterations, Panel G is after 25 iterations and Panel H is after 500 iterations. The parameters of amplitude (a), average baseline (b), phase lag (p), and duration (d) used for matching are shown in each panel. The value d*100 msec gives the time duration of the input signal used for matching with the template. For example, in Panel A (initial, arbitrary weighting), the time duration of the input signal used for matching was 0.6*100 msec=60 msec, which was then resampled at 0.6 msec intervals and expanded (i.e., 100 data points sampled at 0.6 msec intervals were used to match the 100 data point template sampled at 1.0 msec intervals).

FIGS. 6A–F Changes in lines of block during representative episodes of tachycardia. The outline of the electrode arrays are shown. The solid thick black lines indicate the segments of the functional lines of block that were present throughout the episode. The dashed black lines indicate segments of the original lines of block that disappeared during the last several cycles. The circles indicate new segments of lines of block that appeared during the last cycles. Arrows indicate the pattern of propagation of the reentrant wavefront. Panel A shows location of CCP for Tachycardia Episode 2A. Panel B shows location of CCP for Tachycardia Episode 3. Panel C shows location of CCP for Tachycardia Episode 4A. Panel D shows location of CCP for Tachycardia Episode 7. Panel E shows location of CCP for Tachycardia Episode 9. Panel F shows location of CCP for Tachycardia Episode 10.

FIGS. 9A–9D Beat-to-beat changes in electrogram parameters used for ATM analysis from the 4 recording sites during the sustained tachycardia shown in FIG. 4. The recording sites are shown and labeled in FIG. 4B. The abscissa is cycle number beginning one cycle after the template cycle. The ordinate is change in the parameter relative to the template (traces are offset). Panel A is amplitude, Panel B is phase lag, Panel C is duration and Panel D is MSE (intrinsic electrogram shape).

FIGS. 13A–13D The activation maps for cycles at the start and end of quiescent periods denoted by vertical lines in FIG. 12A (episode 1A). Thick black lines denote functional lines of block and thinner lines denote isochrones with 10 msec spacing. Arrows show the direction of propagation of the activating wavefront. The CCP is in the center of the map and the activating impulse proceeds through the CCP toward the LAD margin where it bifurcates. The small numbered text in Panel A denotes activation times at local sites and the larger text denotes isochronal numbers. Sites of interest are circled in FIGS. 13A–B and the site numbers are given in 13B. Panel A shows the activation map for the cycle at the start of the first quiescent period. The small numbered text provides activation times at the local sites and the larger text denotes isochromal numbers. Sites of interest are numbered. Panel B shows the activation map for the cycle at the start of the first quiescent period/start of the second quiescent period. The site numbers of interest are shown by circles. Panel C shows the activation map for the cycle at the end of the second quiescent period/start of the third quiescent period. Panel D shows the activation pap at the end of the third quiescent period.

FIGS. 14A–14D Electrograms from the activation maps of FIG. 13B are displayed and the electrogram numbers are denoted parenthetically between traces. The vertical lines are the activation marks and the difference in activation time between adjacent sites are printed to the right of the first set of marks. The sum of the differences in activation time from sites 61–52 is the approximate total time for activation through the CCP (number in total given at bottom of each panel). The numbers in parentheses between cycles are the local CL. Panel A shows the electrograms for the cycle at the start of the first quiescent period. The site numbers of interest are shown by circles. Panel B shows the electrograms for the cycle at the start of the first quiescent period/start of the second quiescent period. Panel C shows the electrograms for the cycle at the end of the second quiescent period/start of the third quiescent period. Panel D shows the electrograms for the cycle at the end of the third quiescent period.

FIGS. 21A–21C Model of CV changes in the SCZ/RCZ and effect on far-field electrogram deflections. Panel A shows a representative circuit and arcs representing the SCZ, RCZ, and NCZ. CL is initially 208 msec and prolongs to 247 msec. Panel B shows the modeled phase and duration parameters of each colored region based on Table 4. In Panel C the effect of the model parameters on the shape of an electrogram is shown.

FIGS. 23A–23D Examples of how the weighted input signal (thin trace) converges for best overlap with the template during ATM are shown for electrograms obtained from experiment 2. Initially (Panel A), the input signal has different characteristics from the template. After 5 (Panel B), 25 (Panel C) and 500 (Panel D) iterations of the weighting algorithm, the overlap of the input with the template electrogram progressively improves. At iteration 500 convergence is considered to be complete. To the extent that the intrinsic shapes of the template and input are different, the overlap of the signals upon convergence will be incomplete.

FIGS. 26A–26D ATM weighting over 50 cardiac cycles during experiment 2 for sinus rhythm (Panel A), pacing from the LAD and base (Panel B and C), and ventricular tachycardia (Panel D). The panels show the variation of ATM amplitude, phase shift, duration, and MSE weights over 50 consecutive cardiac cycles. Traces are shown for sites 46, 55, 78, and 58 which are circled in FIG. 3 and are respectively further away from the position of any functional lines of block. Generally, electrogram shape is most variable during ventricular tachycardia, less variable during pacing, and the least variable during sinus rhythm. Variability also decreases as the distance from the site to any functional line of block increases.

FIGS. 27A–27D ATM weight variability peak maps constructed from sinus rhythm data are given for experiment 2. In each of the panels the duration parameter variance is shown. In panels A–D are shown the ATM weight variability map for amplitude, phase lag, duration, and normalized mean variance, respectively. The locations of functional lines of block during reentry, determined by activation mapping, are denoted by thick black lines. The largest variance peaks often reside adjacent to functional lines of block; however, there are peaks away from block lines particularly in Panels B–D.

FIGS. 29A–29D ATM weight variability peak maps constructed from reentrant ventricular tachycardia data are given for experiment 2 and described in FIG. 27. The largest variance peaks often reside adjacent to functional lines of block. The panels show the ATM weight variability doe amplitude (panel A), phase lag (panel B), duration (panel C), and normalized mean variance (panel D).

FIG. 31 ATM—flow chart of the adaptive template matching (ATM) algorithm. The procedure to obtain and process the data to determine locations of functional lines of block using ATM algorithm is shown.

FIG. 32 PLATM—flow chart of the piecewise linear adaptive template matching (PLATM) algorithm. The procedure to obtain and process the data to determine the locations of the slow conduction zone (SCZ) proximal and distal edges with respect to the catheter tip using PLATM is shown.

FIG. 33 NATM—flow chart of the non-linear adaptive template matching (PLATM) algorithm. The procedure to obtain and process the data to determine the locations of the central common pathway (CCP) entrance and exit borders with respect to the catheter tip using NATM is shown.

FIGS. 37A–37B (and continued) Flow of the Procedure—the procedure to locate reentrant circuit features and update the catheter tip location toward the best site to ablate the heart are given. The type of instruction to be carried out is given at each step, along with the best site to ablate the heart are given, and for subsystem 3, the name of the algorithm used.

DETAILED DESCRIPTION OF THE INVENTION

Figure 1:
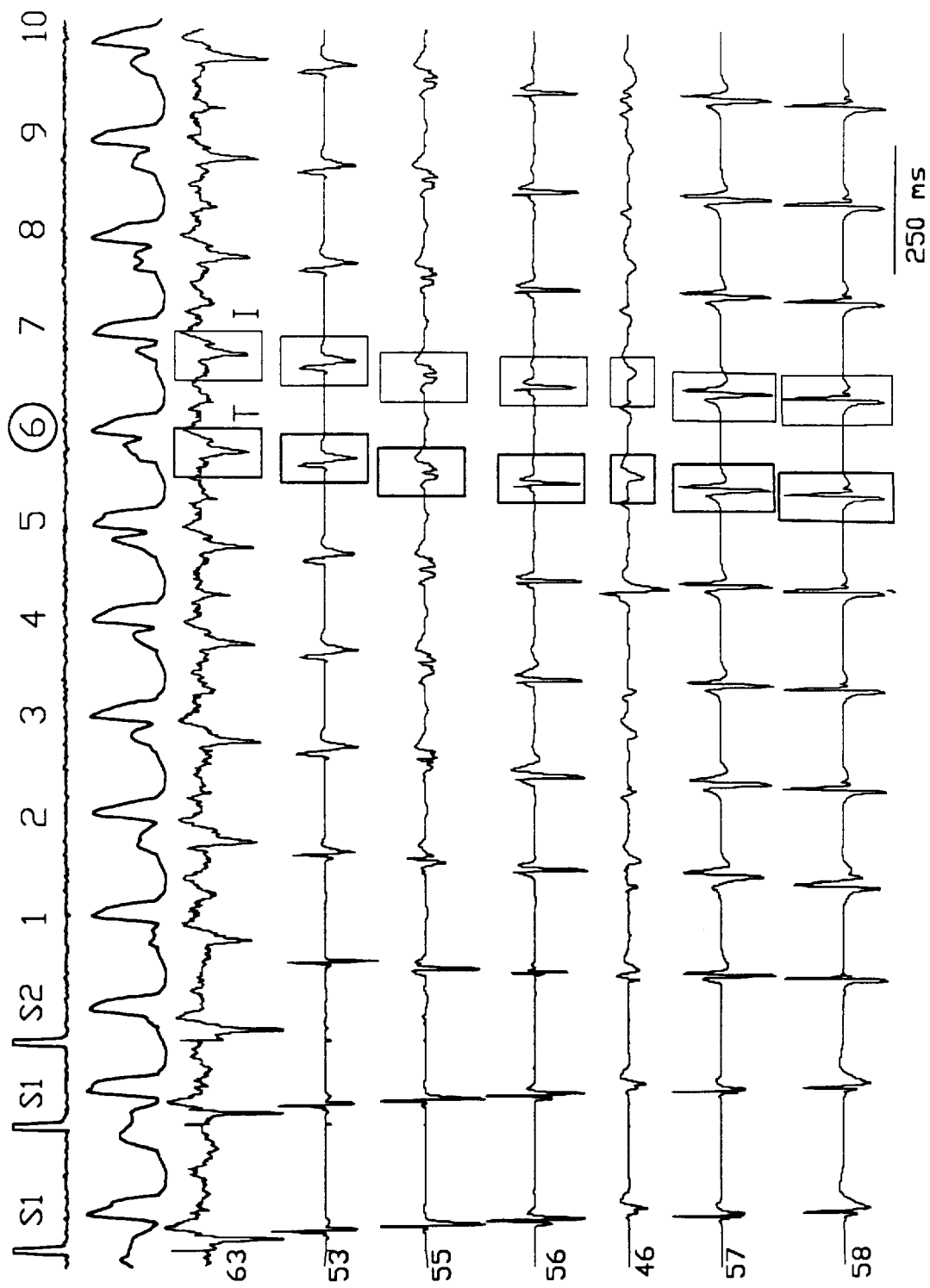
FIG. 1 Initiation of ventricular tachycardia by a premature stimulus (S2) during basic drive (S1). Stimulus pulse (top trace), ECG (second trace) and 7 selected electrograms from the mapping electrode array are shown. The template (T) used for adaptive template matching of electrograms is QRS number 6. Template electrograms are enclosed in rectangles with thick borders. The first input electrograms (I) are enclosed in rectangles with thin borders.
Figure 3B:
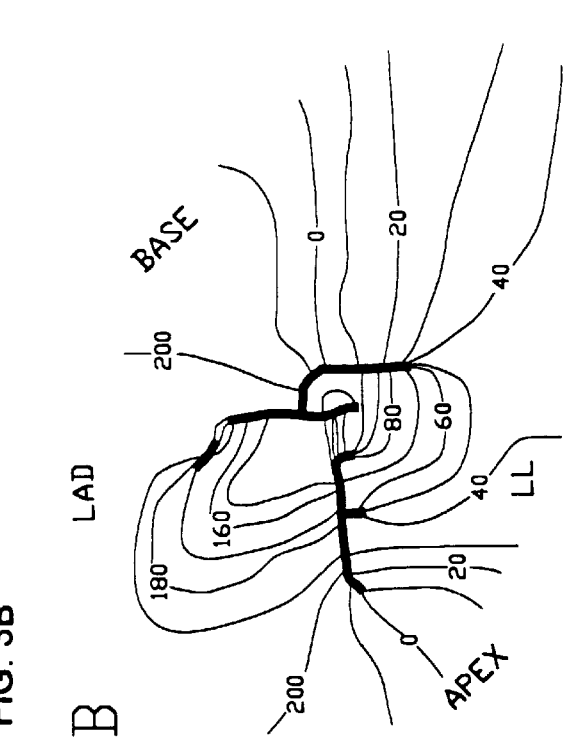
FIGS. 3A–3D Activation maps of the reentrant circuit causing the tachycardia illustrated in FIG. 1. In each panel is a representation of the 196 bipolar electrode array. The margins of the array at the LAD, base, lateral left ventricle (LL) and apex are labeled. Panel A shows the activation pattern during cycle 15; Panel B during cycle 25; Panel C during cycle 35 and Panel D during cycle 45. The small numbers in Panel A are activation times at each of the recording sites. Activation times have been omitted from the other panels. Isochrones are drawn at 10 msec intervals and are labeled with the larger numbers. Thick black lines designate regions of conduction block. Arrows point out the direction of wavefront propagation.
Figure 3D:
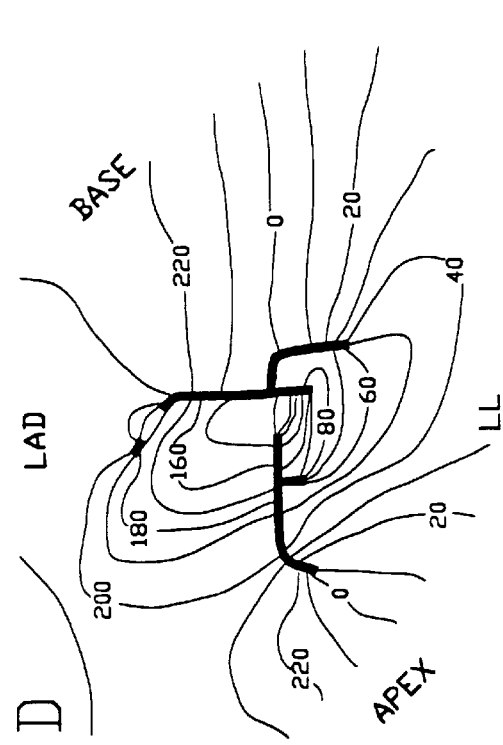
Figure 3A:
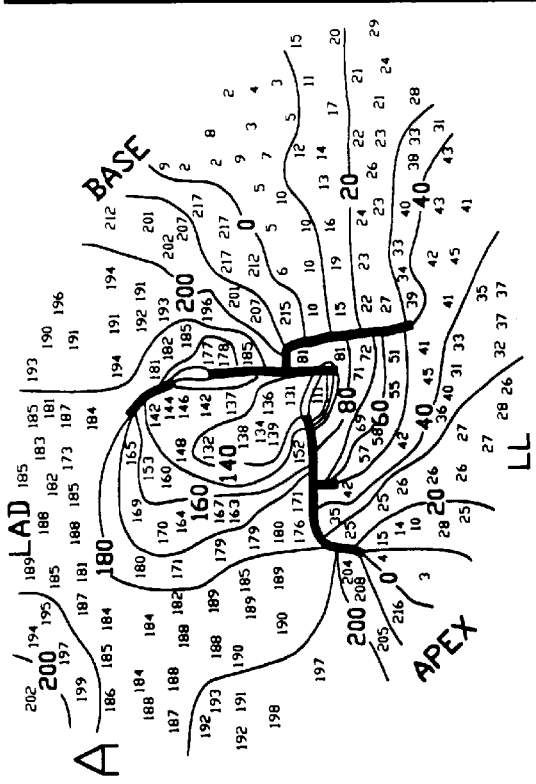
Figure 3C:
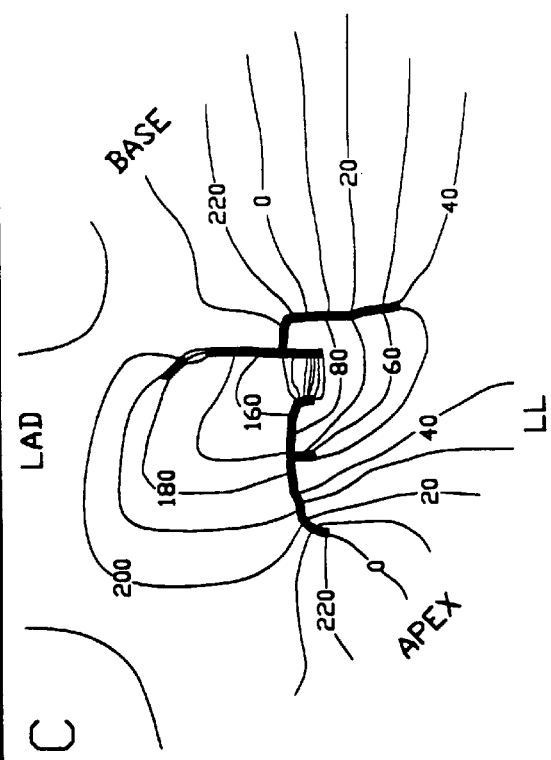

As used herein, the "ATM Algorithm" can be described briefly as a way to adaptively update multiple weights for optimal overlap of a template with an input signal using the estimated mean square error (MSE) criterion. The weight update equation for one weight is given by[20]:

$$w_{i+1}=w_i+\mu\Sigma_{k=1}^{N}[\epsilon_k(y_k^+-y_k^-)] \text{ for i=1 to P} \tag{A1.1}$$

where convergence to the minimum MSE, which provides best overlap of the signals, is approximated to be complete at P=500 iterations, the estimated signal $y_k$ is formed by weighting the input signal $x_k$ by $w_i$ during iteration i, $y_k^+-y_k^-$ is an estimate of the derivative of $y_k$ using finite weight differences $w_i+\Delta w_i$, and $w_i-\Delta w_i$ for weighting $x_k$ to form, respectively, $y_k^+$ and $y_k^-$, $\mu$ is a coefficient of convergence, the residual error $\epsilon_k$ is the difference $d_k-y_k$ between the template $d_k$ and the estimated signal $y_k$, and N is the total number of discrete sample points used for template matching. Equation A1.1 was used to separately compute the weight update for the ATM weights of scale (amplitude and duration) and shift (phase lag and average baseline). The MSE, in addition to being the criterion for adaptive weight update, also provided a measure of the similarity in shape between the template electrogram and the weighted input electrogram following convergence of the weights. The MSE can be approximated as[20]:

$$MSE \approx 1/N\Sigma_{k=1}^{N}[\epsilon_k] \text{ for k=1 to N} \tag{A1.2}$$

The coefficient of convergence (in Equation A1.1 was first estimated for each electrogram channel according to the estimated energy of the signal in accordance with the principles of adaptive signal processing [20]. The mean MSE over all cardiac cycles was then computed using this approximation. However, the precise magnitude of the convergence coefficients effects convergence of the weights. If the coefficients are too small then the ATM weights will never reach the values necessary for optimal overlap of template with input electrograms whereas if they are too large the ATM weights will overshoot the optimal values. An intermediate value of convergence coefficient magnitudes will generate the optimal ATM weighting for best overlap of the template with the input electrogram, and these intermediate values were computed as follows. All four estimated convergence coefficients were scaled by 0.98 times their initial values, and the mean MSE over all cardiac cycles was recomputed. If the mean MSE decreased then the convergence coefficients were scaled again to 0.96 times their original value, whereas if the mean MSE increased they were scaled to 1.02 times their original value. This process was continued until the scale of the convergence coefficients produced the minimum mean MSE over all cardiac cycles. This was done separately for all electrograms and all episodes of tachycardia.

This invention provides a method comprising the steps of identifying and localizing reentrant circuits from electrogram features using feature detection and localization (FDL) algorithms.

As used herein, "identify" means to determine what type pf reentrant circuit feature algorithm such as, central common pathway, slow conduction zone, functional lines of block, pivot point, or central common pathway entrance and exit boundaries.

As used herein, "localize" means to determine the position of reentrant circuit features on the surface of the heart.

As used herein, "reentrant circuit" means an abnormal rhythm of the heart in which the electrical activation wavefront that causes contraction of the heart moves in a circular pattern around an obstacle where conduction occurs slowly or not at all. This type of rhythm causes the heart to beat rapidly and inefficiently.

As used herein, "electrogram" means the electrical signal obtained from the surface of the heart. Each time the conducting wavefront that causes the heart to contract passes beneath the electrode used to acquire the electrogram, a deflection is produced in the signal.

As used herein, "electrogram features" means the characteristics of the shape of the electrogram signal including the heights, angles, and positions of both peaks and plateaus.

As used herein, "adaptive template matching," abbreviated as ATM, uses a template or prototypical electrogram to match with an exemplar or input electrogram by updating parameter weights of the input electrogram so that its shape is conformed as much possible as to that of the template. The weight update process is based on an error criterion and is called adaptation.

This invention provides the above method farther comprising the steps of:

a) using a contoured array of electrodes arranged in concentric circular patterns to obtain signals from the hearts surface to determine the direction and velocity of the activating wavefront at the catheter location;

b) obtaining and preprocessing analog electrogram signals, and multiplexing and storing the signals, in analog or digital form.

c) creating real-time maps and generating other textual information that are displayed on a computer screen, based on reentrant circuit features algorithms.

This invention provides the above method for quantifying dynamic, beat-to-beat changes in electrogram morphology.

As used herein, "dynamic, beat-to-beat changes" means the differences in electrogram shape which occur over the course of two or more cardiac cycles.

As used herein, "electrogram morphology" means the quantitative characteristics of the shape of the electrogram.

This invention provides the above method, wherein signal segments are adaptively matched for best overlap.

As used herein, "signal segment" means a continuous portion of the signal which is bounded by a starting point and an ending point.

As used herein, "adaptively matched" means use of an error criterion for adjustment of weights that change the shape of the input signals so that it better overlaps the shape of the template signal.

As used herein, "best overlap" means the input signal weighting that produces the closest fit overlap with the template.

This invention provides the above method for quantifying the linear parameter of electrogram shape. One embodiment of the linear parameter is scale. One embodiment of the scale is amplitude. Another embodiment of the scale is duration. Another embodiment of the linear parameter is shift. One embodiment of the shift is phase lag. Another embodiment of the shift is the average baseline.

As used herein, "linear parameter of electrogram shape" means a parameter that changes in constant proportion to changes in weighting.

As used herein, "scale" means the size of the signal in two or more dimensions. The vertical dimension of scale is the signal amplitude. The horizontal dimension of scale is the time base, i.e., duration.

As used herein, "amplitude" is expressed as the ratio of the input electrogram amplitude to the template amplitude and is unitless. Although amplitude is often defined as the maximum baseline to peak excursion of the signal in the vertical direction, as used here, it is considered to be the average height of the signal over its entire length.

As used herein, "duration" is a unitless coefficient which defines the input signal window length and scales it with respect to the window size as the template. For example, if the template window is 100 msec sampled at msec intervals, and the duration parameter is 1.2, it means by definition that the input signal window length is 120 msec, which is then resampled by linear interpolation every 1.2 msec.

As used herein, "shift" means the position of the signal along the vertical axis and along the horizontal axis. Along the vertical axis the shift is termed the average baseline and along the horizontal axis the shift is termed the phase lag.

As used herein, "phaselag" means the shift of the signal along the horizonal axis.

As used herein, "average baseline" means the shift of the signal along the vertical axis.

This invention provides the above method for quantifying the piecewise linear parameter of electrogram shape. In one embodiment the piecewise linear parameter is scale. In one embodiment the scale is amplitude. In one embodiment the scale is duration. In another embodiment the piecewise linear parameter is shift. In one embodiment of the above method, the shift is average baseline. In another embodiment of the above method, the shift is phaselag.

As used herein, "piecewise linear parameter of electrogram shape" means a measure of the shape of the electrogram that is determined over a short interval of the signal called a sliding window. A window is the interval, defined by its beginning and ending point, over which the signal is quantified.

As used herein "sliding window" means to move both end points of the windowed interval to another portion of the signal and then to quantify the signal over the new interval.

As used herein, "windowed interval" means a segment of a signal whose endpoints are mathematically defined by means of a window.

This invention provides a method of quantifying non-linear parameters of electrogram shape. In one embodiment the non-linear parameters are the low pass filter coefficients. In another embodiment the non-linear parameters are the high pass filter coefficients. In another embodiment the non-linear parameters are the notch pass filter coefficients. In another embodiment the non-linear parameters are the bandpass pass filter coefficients. In another embodiment the non-linear parameters are the exponential or other nonlinear coefficients.

As used herein, "non-linear parameters of electrogram shape" means measurement of the shape of the signal based on properties that are not constantly proportional over different portions of the signal.

As used herein, "low pass filter coefficient" means properties or values that determine the high frequency components of the signal are removed by the low pass filter.

As used herein, "high pass filter coefficient" means properties or values that determine the low frequency components of the signal are removed by the high pass filter.

As used herein, "notch pass filter coefficient" means properties or values that determine the middle frequency components of the signal are removed by the notch pass filter.

As used herein, "bandpass pass filter coefficient" means properties or values that determine the low and high frequency components of the signal are removed by the bandpass filter.

As used herein, "exponential or other nonlinear coefficients" means properties or values that determine the combined low and high frequency components of the signal are removed by the exponential or other nonlinear coefficients filter.

This invention provides the above method which uses the mean square error criterion or other criteria for adaptation of weights. In one embodiment, the mean square error measures cycle-to-cycle changes in intrinsic electrogram shape.

As used herein, "mean square error criterion" means the sum of squares difference between template and input which is the criterion used to adapt ATM weights for best overlap of the two signals. When the weights are optimal it is also a measure of changes in intrinsic shape between the two signals that occur from cycle to cycle.

As used herein "other criteria" includes but is not limited to the square root or absolute value mean square root of absolute value, the absolute value, mean absolute values, cubic error, mean cubic error, or other error function.

As used herein, "adaptation of weights" means based on an error criterion or criteria, to adjust the weights used to conform the input signal for best overlap with the template.

As used herein, "cycle-to-cycle changes in intrinsic electrogram shape" means the changes in electrogram intrinsic shape that occur over multiple cardiac cycles.

This invention provides the above method wherein each electrogram on each cardiac cycle is compared to a reference electrogram or template electrogram. In one embodiment, the reference or template electrogram is obtained from a representative cycle. In another embodiment, the reference or template electrogram is obtained from an average of multiple cycles. In another embodiment, the above method is used to obtain information about changes which occur in electrogram morphology over multiple cardiac cycles from one cardiac cycle to the next.

As used herein, "cardiac cycle" means the time for the heart to undergo one period of electrical depolarization of the heart cells, causing contraction of the heart.

As used herein, "reference electrogram" means the differences in angular, amplitude, and slope properties and relationships of signal peaks and plateaus from cycle-to-cycle and/or site-to-site.

As used herein, "template electrogram" means any cardiac cycle subsequent to the one being studied.

As used herein, "representative cycle" means a cycle in which the electrogram is very similar to electrograms of subsequent cardiac cycles.

As used herein, "average of multiple cycles" means the statistical mean, median, mode or other statistical parameters used to determine an intermediate electrogram from two or more electrogram shapes obtained from two or more cardiac cycles.

As used herein, "information about changes in electrogram morphology" includes but is not limited to the quantitative differences in electrogram shape which occur over two or more cardiac cycles.

In one embodiment, the above method uses the differential steepest descent method or other adaptive method to compute the weight update.

As used herein, "differential steepest descent method" means a technique well known in the literature for weight update in which the direction and magnitude of the weight update depends on the slope of the MSE performance curve.

As used herein, "other adaptive methods" includes but is not limited to Newton's Method, and other gradient methods as well as other adaptive methods such as the lattice method.

As used herein, "weight update" means to adjust the weights so that the MSE or other error function is minimized. When the MSE is minimized, the weights are the optimal weights.

In one embodiment, the magnitude and direction for weight adjustment are determined by calculating a derivative or other function of the error based on finite difference changes or other changes in the weighting. In one embodiment, this method is used to minimize the misadjustment of the weight update. In one embodiment, the convergence coefficient is optimized in order to minimize the misadjustment of the weight update. In one embodiment, the convergence coefficient is incremented up or down in order to minimize the mean square error or other error for function during weight update.

As used herein, "magnitude for weight adjustment" means the sign (positive or negative) of the increment used to update the weight as it is being guided toward its optimal weighting.

As used herein, "derivative or other function of the error based on finite difference changes or other changes in the weighting" means the difference in the error computed with a given weight versus the error computed when the weight is incremented, divided by the magnitude of the weight increment.

As used herein, "other function" includes but is not limited to partial derivatives, second derivative, other derivative, weighted derivative, highpass filter and bandpass filter.

As used herein "finite difference changes in weighting" mean weights are incremented by minute fractions of the actual value of the weight.

As used herein, "other changes in the weighting" include but are not limited to differences in the weighting when the weight increment is not fixed but rather is dependent on the error function.

As used herein, "minimize the misadjustment of the weight update" means the combination of window size, finite difference increments, and convergence coefficient magnitude that guides the weight update towards the optimal weighting with best accuracy and efficiency.

As used herein, "convergence coefficient" means a coefficient which partially determines the size of the weight update.

As used herein, "convergence coefficient is optimized" means to adjust the coefficient magnitude so that the size of the finite difference weight increments, in tandem with the window length, maximize the accuracy and efficiency of the weight update.

As used herein, "incremented up or down" means the sign of the weight increment is positive or negative, respectively.

As used herein, "minimize the mean square error" means to decrease the mean square error of the match between the template input signals to its lowest possible value.

As used herein, "other error" includes but is not limited to absolute value, mean absolute value, square root of absolute value, mean square root of absolute value, or other ordered error function.

In one embodiment, the length of segment is maximized to minimize the misadjustment of the weight update. The maximum length can range of 50 to 1000 milliseconds.

As used herein, "length of segment" also means "number of successive data samples." As used herein, "length of segment" means the number of successive data points contained in the matching window.

This invention provides the above method wherein the finite difference is optimized to minimize the misadjustment of the weight update. In one embodiment, the finite difference is incremented to minimize the mean square error or other error function during weight update.

As used herein, "finite difference" means two minute increments, one positive and one negative, are separately added to the weight to form two new weight values, one slightly more negative and one slightly more positive than the original weight.

As used herein, "optimizing the finite difference" means to adjust the finite difference for maximum accuracy and efficiency of the weight update based on the mean square error or other error function.

As used herein, "incremented to minimize the mean square error or other error function during weight update" means to adjust the weight using increments until the mean square error or other error function is at the lowest possible value, for a given template and input signal.

In one embodiment of the above method, functional lines of block in reentrant circuits are located by analyzing ATM algorithms. In one embodiment, the data is obtained during sustained monomorphic ventricular tachycardia.

As used herein, "functional lines of block" means a boundary separating adjacent electrode sites with activation time differences greater than 40 msec and in which the activating wavefronts on opposite sides of the line are moving in different directions.

As used herein, "reentrant circuit" means the pathway in which the activating wavefront propagates during reentry.

As used herein, "sustained monomorphic ventricular tachycardia" means a tachycardia which is maintained more than 30 seconds after onset, or one that must be terminated by electrical stimulation prior to 30 seconds after onset due to hemodynamic instability.

As used herein, "ventricular tachycardia" means an abnormal heart rhythm in which the heart beats more rapidly than normal, which can be caused by a reentrant circuit.

In another embodiment of the above method, functional lines of block in reentrant circuits can be located by analyzing ATM variances or other weight variabilities from data obtained during unsustained monomorphic ventricular tachycardia.

As used herein, "other ATM weight variabilities" include but are not limited to range function, quartile function, extremum function, trend or other variability.

As used herein, "unsustained monomorphic ventricular tachycardia" means monomorphic ventricular tachycardia which lasts less than 30 seconds from onset to termination.

In another embodiment of the above method, functional lines of block in reentrant circuits can be located by analyzing ATM variances or other weight variabilities from data obtained during polymorphic ventricular tachycardia.

As used herein, "polymorphic ventricular tachycardia" means ventricular tachycardia in which the shape of the electrocardiogram is highly variable from one cardiac cycle to the next, which is usually accompanied by simultaneous changes in the location and type of reentrant circuit features.

In another embodiment of the above method, functional lines of block in reentrant circuits can be located by analyzing ATM variances or other weight variabilities from data obtained during sinus rhythm.

As used herein, "sinus rhythm" means the normal rhythm of the heart in which the regular beating of the heart initiates in a specialized heart cell in a region of the heart called the sinoatrial node.

In another embodiment of the above method, functional lines of block in reentrant circuits can be located by analyzing ATM variances or other weight variabilities from data obtained during ventricular pacing.

As used herein, "ventricular pacing" means to electrically stimulate the ventrical at one or multiple sites at regular intervals when the heart is in sinus rhythm.

In another embodiment of the above method, functional lines of block in reentrant circuits can be located by analyzing ATM variances or other weight variabilities from data obtained during pacing during ventricular tachycardia.

In one embodiment of the above methods, the analysis is performed by computer processing.

As used herein, "computer processing" means to encode and use the ATM algorithms via a digital computer.

As used herein, "analyzing ATM weight variabilities" means determining the relationships of the ATM weight variabilities for all ATM parameters at each site on the heart where electrogram signals are obtained.

This invention provides the above method wherein the regions of greatest variance of ATM parameters are adjacent to the location of functional lines of block that formed the boundaries of the central common pathway in reentrant circuits. In one embodiment, an average of variances for sites with low variance is used as a threshold.

As used herein, "regions of greatest variance of ATM parameters" means those portions of the heart which exhibit a large ATM weight variability relative to surrounding areas of the heart.

As used herein, "adjacent to the location" means the site or sites neighboring the site in question on the surface of the heart.

As used herein, "formed" means the shape of the signal following quantitative manipulations of the original shape of the signal.

As used herein, "central common pathway," abbreviated as CCP means a portion of a reentrant circuit with "figure-of-eight" pattern that is common to both reentrant loops and which is protected by two bounding lines of block, one on either side, with an entrance and exit to the region through which the activating wavefront can pass.

As used herein, "figure of eight reentry" means a type of abnormal cardiac rhythm in which the activating wavefront circles and then reenters the region that it activated previously, having two loops or wavefronts.

As used herein, "boundaries of the central common pathway" means the four edges of the CCP; they are the two sides which consist of the bounding functional lines of block, the entrance to the CCP, and the exit from the CCP.

In one embodiment, the above method is used to locate reentrant circuits for localized drug intervention, surgical incision or catheter ablation in a subject. In one embodiment, the subject is one with ventricular tachycardia.

As used herein, "locate reentrant circuits" means to determine the position and boundaries of specific features of reentrant circuits such as the CCP, the pivot points around which the wavefront turns, and the SCZ within the CCP.

As used herein, "localized drug intervention" means to introduce antiarrhythmic agents at a specified area of the reentrant circuit.

As used herein, "surgical incision" means to create a lesion in a portion of the heart by using a surgical knife or other surgical instrument, thereby interrupting electrical conduction of the activating wavefront across the lesion area.

As used herein, "catheter ablation" is the creation of a lesion of the surface of the heart using radiofrequency or other energy source emitted from the end or tip of a tubular device called a catheter that is positioned through a large artery into the ventricular chamber of the heart.

As used herein, "subject" is an animal. In one embodiment, the subject is a human. In the preferred embodiment, the human is a patient undergoing electrophysiologic testing to determine the site where the heart should be ablated, and undergoing ablation procedure to stop reentrant ventricular tachycardia.

As used herein, "ventricular tachycardia" means an abnormal cardiac rhythm in which the heart beats rapidly and blood is pumped inefficiently which can be caused by a reentrant circuit.

In one embodiment of the above method, functional reentrant circuits and functional lines of block that bound the central common pathway can be located for catheter abalation of ventricular tachycardia without the necessity for recording from a large number of sites and without constructing activation maps.

As used herein, "functional reentrant circuits" means a reentrant circuit in which the activating wavefront travels in a loop around an area of tissue where no conduction occurs during the tachycardia but where conduction will occur during the normal rhythm of the heart (sinus rhythm).

As used herein, "recording" means to permanently store data such as the electrogram signals on a magnetic or other medium where it is easily retrievable for later analysis.

As used herein, "large number of sites" means typically, 50–1000 locations where electrogram signals are acquired simultaneously from the surface of the heart.

As used herein, "activation maps" means visual displays of the pathways of electrical conduction on the heart's surface which are generated by quantifying the deflections of the electrogram signals obtained simultaneously from many sites on the heart's surface.

As used herein, "constructing activation maps" means to generate an activation map based on the marking of a fiduciary point, usually the point of largest slope of the electrogram deflections, each cardiac cycle. These times are then displayed as a computerized grid and isochrones of similar activation times are drawn based on the activation times.

In one embodiment, the region of greatest increase of the PLATM duration parameter when tachycardia cycle length increases resides at the location where slow conduction occurs in the central common pathway of a reentrant circuit. In another embodiment, the region of greatest decrease of PLATM duration parameter when tachycardia cycle length decreases resides at the location where slow conduction occurs in the central common pathway of a reentrant circuit.

As used herein, "region of greatest increase" means the portion of the heart where one or more of the ATM parameters increases the most with respect to all sites where electrogram records were obtained.

As used herein, "region of greatest interest" means the area of the heart where the reentrant circuit occurs, and specifically that part of the reentrant circuit which is the best site to ablate to interrupt the circuit and permanently stop ventricular tachycardia.

As used herein, "ATM duration parameter" means the signal time base property that is a measurable quantity that can be scaled to contract or expand the signal, measured over a short sliding window interval.

As used herein, "slow conduction" means travel of the activating wavefront at a lower speed than normal from one heart cell to the next.

In one embodiment, the method updates the location of an ablation catheter based on far-field electrogram deflections.

As used herein, "updates" means the magnitude of any given weight following one algorithmic iteration to compute the incremental weight change that adjusts the weight toward the optimal value.

As used herein, "location of an ablation catheter" means the position of the tip of the ablation catheter in the ventricular chamber of the heart.

As used herein, "far-field electrogram deflections" means the deflections of the electrogram signal that are caused by electrical activity (i.e., the activating wavefront) when it is distant (greater than 2 millimeters) from the location of the electrode from which the electrogram is obtained.

This invention provides the above method wherein other changes in PLATM parameters including duration, phase lag, amplitude, average baseline, or other parameters when tachycardia cycle length changes resides at the location where slow conduction occurs in the central common pathway of a reentrant circuit.

In one embodiment of the above method, the PLATM phase shift parameter is used to determine the time of activation of the zone of slow conduction with respect to the local activation time at the position of the catheter.

As used herein, "PLATM phase shift parameter" means the property of the signal, measure over a short sliding window, of the position of the signal deflections along the horizontal axis with respect to an arbitrary fiduciary time.

As used herein, "time of activation of the zone of slow conduction" means the interval during which the area of the heart within the central common pathway where slow conduction occurs, activates. The proximal border of the SCZ activates first, and the distal border activates last.

As used herein, "current position of the catheter" means the present location of the tip of the catheter from which electrogram signals are acquired and from which energy is imparted to ablate the heart.

In one embodiment a model is used to convert the direction and time into a distance from the current position of the catheter to the zone of slow conduction.

As used herein, "model" means a mathematical construct that simulates physiological conditions so that estimates can be made about how certain physiological parameters will change.

As used herein, "convert" means to change the form from one type to another.

As used herein, "direction" means the angle of a given entity such as a wavefront with respect to an arbitrary fiducial angle.

As used herein, "time" means the period of waiting required, or the interval required, for an event to occur.

As used herein, "distance from the current position of the catheter to the zone of slow conduction" means the time difference in activation between the two locations, or the physical difference between the two locations.

In one embodiment, the PLATM duration parameter is used to determine the time of activation of the zone of slow conduction with respect to the current position of the catheter. In one embodiment, a model is used to convert the direction and time into a distance from the current position of the catheter to the zone of slow conduction.

As used herein, "PLATM duration parameter" means the signal time base property, which is a measurable quantity that can be scaled to contract or expand the signal, measured over a large fixed window interval.

In one embodiment of the above method, the catheter tip location can be directed toward the location of the optimal site to ablate the heart based on the distance from the catheter tip to the slow conduction zone (SCZ) proximal and distal borders.

In another embodiment, the slow conduction zone can be located by analyzing ATM weight variabilities from data obtained during unsustained monomorphic ventricular tachycardia.

In another embodiment, functional lines of block in reentrant circuits can be located by analyzing ATM variances or other weight variabilities from data obtained during polymorphic ventricular tachycardia.

In another embodiment, functional lines of block in reentrant circuits can be located by analyzing ATM variances or other weight variabilities from data obtained during sinus rhythm.

In another embodiment, functional lines of block in reentrant circuits can be located by analyzing ATM variances or other weight variabilities from data obtained during ventricular pacing.

In another embodiment, functional lines of block in reentrant circuits can be located by analyzing ATM variances or other weight variabilities from data obtained during pacing during ventricular tachycardia.

In another embodiment, the analysis is performed by computer processing.

The NATM algorithm will be used to determine the location of the entrance and exit boundaries of the CCP and therefore the lengths of the block lines bounding the CCP. The principle is as follows. As tachycardia cycle length changes, the electrogram shapes will change slightly depending on the filtering characteristics of the tissue. Previous work done in our laboratory has shown that these characteristics differ within the CCP versus outside the CCP. The properties of gap junctions (connecting channels between heart cells) differ within versus outside the CCP, and these differing properties will cause the tissue filtering characteristics to change in each area. The NATM parameters (filter coefficients such as time constants for low, high band pass filtering, notch filtering and other filtering) will differ within versus outside the CCP and these parameters are measurable when there is a change in cycle length. By using NATM in a piecewise linear mode to quantify far-field electrogram deflections, the time difference from local activation at the CCP entrance and exit boundaries can be ascertained from a single site. Based on a mathematical model, this time difference is converted into a physical distance that will provide the distance from the catheter tip to the CCP entrance and exit borders, and therefore the length of the block lines bounding the CCP.

This invention provides the above methods wherein the Nonlinear Adaptive Template Matching (NATM) algorithm filter coefficients are used to distinguish activation occurring inside of the CCP from activation occurring outside of the CCP.

As used herein, "NATM filter coefficients" means parameter values that describe the properties of high, low, bandpass, notch or other filters.

As used herein, "distinguish activation occurring inside of the CCP from activation occurring outside of the CCP" means to determine whether or not activation is occurring within the area bounded by two block lines and the entrance and exit to the CCP, by means of NATM filter coefficients.

In one embodiment of the above method, waveforms are compared at different cycle lengths to determine changes in NATM filter coefficients.

As used herein, "waveforms" means the segments of the electrogram signals that are being quantified.

In an embodiment of the above method, this invention also provide a method to update the location of an ablation catheter based on electrogram far-field directions.

In one embodiment, the catheter tip location can be directed toward the location of the optimal site to ablate the heart based on the distance from the catheter tip to the CCP entrance and exit.

In one embodiment, NATM filter coefficients change when cycle length changes and can be used to determine the time of activation of the borders at the entrance and at the exit of the CCP with regard to local activation time at the portion of the catheter.

In one embodiment of the above method, NATM filter coefficients change when cycle length changes and can be used to detect the border at the entrance and at the exit of the CCP.

As used herein, "NATM filter coefficients change when cycle length changes" means as the period for the activating wavefront to travel once around the reentrant circuit changes, the extent to which the waveforms are filtered by the tissue medium in which they travel changes, which will cause the NATM filter coefficients to change accordingly.

As used herein, "detect the border at the entrance and at the exit of the CCP" means to determine the time at which the activating wavefront crosses the borders at the entrance and at the exit of the CCP with respect to the time of activation at the catheter tip.

In one embodiment of the above method, a model can be used to determine the distance from the local site to the entrance and to the exit of the CCP.

As used herein, "distance from the local site to the entrance of the CCP" means the magnitude and angle of a vector or series of vectors over which the catheter tip would travel on the surface of the heart to arrive at the CCP entrance.

As used herein, "distance from the local site to the exit of the CCP" means the magnitude and angle of a vector or series of vectors over which the catheter tip would travel on the surface of the heart to arrive at the CCP exit.

In one embodiment of the above method, the length of the CCP and the length of the bounding block lines can be determined based on the distances from the catheter tip to the CCP entrance and exit.

As used herein, "length of the CCP" means the distance from the border at which the activating wavefront enters the CCP to the border at which it exits the CCP.

As used herein, "length of the bounding block lines" means the distance from the end of the block line around which the activating wavefront pivots to enter the CCP to its other end around which the activating wavefront pivots after it exits the CCP.

In one embodiment of the above method, the NATM filter coefficients can be determined at sites of distant electrical activity by quantification of electrogram far-field deflections.

As used herein, "sites of distant electrical activity" means areas of the heart greater than 2 mm away from the catheter tip over which the activating wavefront crosses.

As used herein, "quantification of electrogram far-field deflections" means to use RCF algorithms to analyze the deflections in the electrogram acquired at the local site that are due to far-field electrical activity.

In one embodiment of the above method, the catheter tip location can be directed toward the location of the optimal site to ablate the heart based on the distance from the catheter tip to the CCP entrance and exit.

As used herein, "location of the optimal site to ablate the heart" means the narrowest width of the CCP which resides within the SCZ of the CCP.

In an embodiment, the length of the CCP and the length of the bounding block lines can be determined by analyzing ATM variances or other weight variabilities from data obtained during sustained monomorphic ventricular tachycardia.

In one embodiment, the length of the CCP and the length of the bounding block lines can be determined by analyzing ATM variances or other weight variabilities from data obtained during unsustained monomorphic ventricular tachycardia. In another embodiment, the length of the CCP and the length of the bounding block lines can be determined by analyzing ATM variances or other weight variabilities from data obtained during polymorphic ventricular tachycardia. In another embodiment, the length of the CCP and the length of the bounding block lines can be determined by analyzing ATM variances or other weight variabilities from data obtained during sinus rhythm. In another embodiment, the length of the CCP and the length of the bounding block lines can be determined by analyzing ATM variances or other weight variabilities from data obtained during ventricular pacing. In another embodiment, the length of the CCP and the length of the bounding block lines can be determined by analyzing ATM variances or other weight variabilities from data obtained during pacing during ventricular tachycardia.

The conduction velocity (CV) algorithm is used to determine the speed and direction of the activating wavefront at the location of the catheter tip. Based on the activation times at the concentric rings electrodes, the speed and direction of the wavefront is computed based on the maximum, average, median, quartile, or other statistical time difference in activation of any two or more electrodes.

This invention provides the above method wherein a concentric circular multielectrode ring and conduction velocity algorithms are used to determine wavefront speed and direction at the location of the catheter tip.

As used herein, "concentric circular multielectrode ring" means the arrangement of electrode in a series of concentric rings, i.e, in each ring there are several electrodes which are positioned equidistant from each neighboring electrode.

As used herein, "wavefront speed" means the time required for the wavefront to travel between two points on the heart.

As used herein, "wavefront direction" means the angle with respect to an arbitrary fiducial angle that the wavefront travels.

In one embodiment of the above method, the direction of the wavefront is calculated based on the maximum difference in the activation times of any two or more electrodes.

As used herein, "maximum difference in the activation times of any two or more electrodes" means the time difference in activation between two electrodes, or the average time difference in activation between greater than two electrodes that is greater than the difference in activation time at any one.

In one embodiment of the above method, the direction of the block lines with respect to the catheter tip will lie perpendicular to the direction of the wavefront when the catheter resides within the CCP at the SCZ.

In one embodiment of the above method, the conduction velocity of the activating wavefront is determined by dividing the maximum difference in the activation times of any two or more electrodes into the distance between those same electrodes.

As used herein, "conduction velocity of the activating wavefront" means the speed and direction with which the activating wavefront travels.

As used herein, "maximum difference in the activation time" means for a given set of activation times at 2 or more sites occurring during cardiac cycle, the sites or combination of multiple sites with activating times which are the most disparate.

The center of mass (CM) algorithm will be used to determine the location of the narrowest width of the CCP based on ATM weight variability peaks. Once the variance peaks are obtained using the ATM algorithm, the position of the narrowest width of the CCP can be approximated as the center of mass of the highest variance peaks (highest 4–400 of 5–500 total sites). In another embodiment, any number of peaks from 5–500 may be used for CM calculations and they need not include only the highest variance peaks. Our observations show that the narrowest width of the CCP resides within the SCZ of the CCP. Therefore, this measurement is both a pointer to the position of the SCZ, and also determines the position of the narrowest width of the CCP that resides within the SCZ. In human studies, it has been shown that the SCZ is the best place to ablate the heart to stop tachycardia. By ablating not only within the SCZ but at the narrowest CCP width, the length of the ablation lesion needed to interrupt the reentrant circuit and stop tachycardia will be minimized. This minimizes the chance that the heart will be harmed by the procedure during creation of the ablation lesion.

This invention provides the above method wherein the center of the narrowest width of the CCP of reentrant circuits is determined using 5–500 ATM weight variability peaks.

As used herein, "the center of the narrowest width of the CCP of reentrant circuits" means the midpoint on a line drawn from tone bounding line of the block to the other where the distance between the lines of block is at a minimum. This also means "center of the narrowest CCP width location."

As used herein, "ATM weight variability peaks" means the ATM weight variability for a given ATM parameter at a given site.

As used herein, "5–500 ATM weight variability peaks" means 5–500 sites on the heart from which electrogram signals are acquired for ATM calculations.

In one embodiment of the above method, the center of mass (CM) of the highest 5–400 variance peaks is determined to approximate the center of the narrowest CCP width location.

As used herein, "center of mass (CM) of the highest 5–400 variance peaks" means the XY position on the heart which is the mean of the XY positions of all sites where ATM weight variability is higher than a threshold, weighted by the ATM weight variability at that site.

As used herein, "approximate" means the computed XY position is only an estimate of the true XY position of the center of the narrowest CCP width location.

In one embodiment of the above method, the CM of an average of all 5–500 variance peaks from highest to lowest is determined to approximate the center of the narrowest CCP width location.

As used herein, "the CM of an average of all 5–500 variance peaks from highest to lowest" means the XY position on the heart which is the mean of the XY positions of all sites where electrograms are acquired, weighted by the ATM weight variability at the site.

This invention provides the above method, wherein ablation of the central common pathway between lines of functional block at the zone of slow conduction prevents tachycardia.

As used herein, "ablation of the central common pathway between lines of functional block at the zone of slow conduction" means to impart radiofrequency or other energy to the heart with sufficient strength and duration to cause a lesion in the heart muscle that prevents conduction from occurring across the lesion boundary.

As used herein, "prevents" means that the amount is reduced as compared with the amount that would occur without said method. In the preferred embodiment, the amount is reduced 100%. It also means that tachycardia can no longer be induced in the clinical laboratory by artificial electrical stimulation nor will induction occur spontaneously.

In one embodiment of the above invention, ablation of the central common pathway between lines of functional block at the zone of slow conduction prevents tachycardia.

This invention provides the above method for ablating the heart to stop ventricular tachycardia when the lines of block around which the activating wavefront traverses are anatomical, partly anatomical and partly functional, or wholly functional.

This invention provides the above method for ablating the heart to stop ventricular tachycardia when the pattern of reentry is intramural or transmural.

This invention provides the above method for pinpointing sites or specific areas for drug delivery.

This invention provides the above method for detecting and localizing pathologic conditions in but not limited to the heart, brain, lung, gastrointestinal system and musculoskeletal systems.

This invention provides a system comprising a means for localizing reentrant circuits from electrogram features using features detection and localization algorithms.

This invention provides the above system comprising a device which comprises:

a) A multipolar ring catheter which uses a contoured array of electrodes arranged in concentric circular patterns to obtain signals from the heart's surface for the purpose of determining the direction and velocity of the activating wavefront at the catheter location;

b) a data acquisition subsystem used to obtain and preprocess analog electrogram signals, and to multiplex and store the signals in real time using a storage device, in analog or digital form;

c) a processing unit comprising software and hardware for multiple electrodes, and features detection and localization algorithms; and d) a display/guidance subsystem which creates a real-time map that is displayed on a computer screen, based on reentrant circuit features algorithms.

As used herein, "multipolar ring catheter" means an apparatus which can be slid through an artery positioned into a ventricular chamber of the heart and used to record signals via multiple electrodes, which are configured in a circle.

As used herein, "contoured array of electrodes" means a group of electrodes, arranged in a circular pattern, and embedded in a matrix which is shaped to conform to the shape of the heart, for the purpose of acquiring electrical signals from the heart's surface.

As used herein, "electrode" means a metal surface connected to a wire, which serves as a transducer to convert the electrochemical energy obtained from the heart cells in contact with the electrode into electrical energy which flows through the wire.

As used herein, "activating wavefront" means the electrical activity that causes heart cells to depolarize followed by mechanical contraction, which courses around the heart as one or more waves during each heartbeat.

As used herein, "wavefront propagation" means the movement of the activating wavefront across the surface of the heart by cell-to-cell conduction of electricity.

As used herein, "catheter location" means the position of the tip of the catheter on the surface of the heart.

As used herein, "catheter" means a device composed of a narrow, flexible tube capable of fitting within the confines of a human artery which contains. electrodes for recording electrogram signals and for ablating the heart.

As used herein, "data acquisition subsystem" means the apparatus used to obtain electrogram signals from the catheter, process them, and store them on a permanent media.

As used herein, "preprocess" means to amplify, filter, and otherwise adjust the electrogram signals prior to digitization.

As used herein, "analog electrogram signal" means the unbroken, continuous electrogram signal acquired from an electrode prior to digitization.

As used herein, "digital" means to determine the value of the analog electrogram signals at discrete intervals, for the purpose of storing these values in a digital computer.

As used herein, "real-time" means the immediate, or present, time and refers to a process or event that takes place immediately.

As used herein, "storage device" is an electromagnetic apparatus, which has the capacity to store large numbers of signals permanently on magnetic or other media with the capability to retrieve the signals at any time.

As used herein, "processing unit" means the hardware/software which operates on the data based on reentrant circuit feature algorithms.

As used herein, "algorithm" means a set of arithmetic and logical statements used to process a set of numbers.

As used herein, "display/guidance subsystem" means an apparatus for visually showing the information generated by the multipolar catheter and the ATM, PLATM, and NATM algorithms in a format useful to the clinician for rapid update catheter tip position on the surface of the ventricle toward the best location to ablate the heart.

As used herein, "real-time map" means to display an image containing information about the magnitude of a heart parameter and its location on the surface of the heart.

As used herein, "computer screen" means the cathode ray tube (CRT), liquid crystal display (LCD) or other apparatus for visualizing the information generated by the computer.

This invention provides the above system wherein the multipolar catheter ring comprises electrodes attached to thin, shielded, insulated wires at the catheter tip for recording electrogram signals and for ablating the heart from any of the electrodes.

As used herein, "thin" means wires of a thickness that when bundled together and wrapped in a flexible tube, can fit within the interior of the femoral or other arteries through which the catheter must travel to be localized within the ventricle.

As used herein, "shielded, insulated wires" means that a metal in the form of a wire that conducts electricity is coated with an insulating material that does not conduct electricity, and this insulating material is covered with a metal conductor coating which is connected to a ground.

As used herein, "ground" means a potential difference voltage level of zero volts.

As used herein, "catheter tip" means the distal end of the catheter, i.e., the end that is positioned within the ventricular cavity.

As used herein, "electrogram signals" means the electric waveform obtained from the surface of the heart with dependent variable being the potential difference voltage and the independent variable being time.

As used herein, "ablating the heart," means to impart energy such as radiofrequency to the heart, causing a lesion, for the purpose of interrupting the conduction of electricity at the site of the lesion.

This invention provides the above system wherein the multipolar catheter ring comprises a configuration of electrodes in a circular pattern at the catheter tip for the purpose of recording electrogram signals and also ablating the heart with radiofrequency or other energy.

As used herein, "configuration of electrodes in a circular pattern" means to position the electrodes, equispaced along the edges of a circle.

As used herein, "radiofrequency energy" means electrical energy in the form of sinusoidal waveforms in the range of 0.5 to several megahertz that is imparted to the heart's surface through an electrode to cause a lesion in the heart tissue.

As used herein, "other energy" includes but is not limited to DC energy, laser energy and cryothermal energy.

This invention provides the above system wherein the multipolar catheter ring comprises a conical-shaped or similarly-shaped electrode array with fan-like or other folding action, that is initially compactly folded when traveling within the confines of a human artery, but which opens into a conical-shape when positioned within a ventricular cavity of the heart so as to fit the contour of the heart.

As used herein, "conical-shaped" means having the shape of a cone, which may be cropped at the top and rounded at the sides.

As used herein, "similarly shaped" means having a contoured or rounded pattern that enables most or all of the multielectrodes to be in contact with the heart surface at one time.

As used herein, "fan-like folding action" means having a motion of a folding hand fan, which can be collapsed or expanded.

As used herein, "other folding action" includes but is not limited to sliding, racheting, or swiveling mechanism that transforms the multielectrode array from a compact form to an expanded, conical or similarly contoured form.

This invention provides the above system, wherein the multipolar catheter ring comprises a thin, tough, flexible catheter shell that contains the wires used to record electrograms and to ablate the heart.

As used herein, "thin, tough, flexible catheter shell" is a compact, tubular material used to contain the electrode wires.

As used herein, "record electrograms" means to store the electrogram signals on a permanent media so that they may be later retrieved for quantitative analysis.

This invention provides the above system, wherein the multipolar catheter ring comprises a terminal mount that is used to rapidly connect/disconnect the catheter at its proximal end to the data acquisition subsystem.

As used herein, "terminal mount" means the electrical contact that interfaces the catheter wires at their proximal end, with the input connector for the data acquisition subsystem.

As used herein, "proximal end" means the end of the catheter opposite to its tip, which never enters the patient, at which the catheter wires are terminated in an electrical connector.

This invention provides the above system, wherein the data acquisition subsystem comprises circuitry to amplify the signals to reduce noise pickup.

As used herein, "circuitry" means the configuration of electronic components needed to do a certain task.

As used herein, "amplify" means to enlarge the electrogram signal along its vertical axis.

As used herein, "reduce" means a lower amount as compared to a control situation.

As used herein, "noise pickup" means the addition of noise to the electrogram signal, which is unwanted.

This invention provides the above system, wherein the data acquisition subsystem comprises circuitry used to low pass filter the signals to prevent aliasing during the digitization process.

As used herein, "filter" means to remove certain frequency components of the signal.

As used herein, "low pass filter" means a filter that removes high frequency but not low frequency components from an electrogram signal.

As used herein, "frequency components" are sinusoidal signals which, when combined additively based on the principles of Fourier theory, can be used to form any given signal.

As used herein, "aliasing" means a spurious change in the shape of the electrogram signal, which occurs when it is digitized without being low pass filtered at a specified value.

As used herein, "digitization process" means the transformation of a signal from a continuous to discrete form.

This invention provides the above system, wherein the data acquisition subsystem comprises circuitry used to high pass filter the signals to prevent the buildup of bias voltage.

As used herein, "high pass filter" means a filter that removes low frequency but not high frequency components from an electrogram signal.

As used herein, "bias voltage" means an unwanted change in the average baseline level of the signal that may occur if the signal is not properly high pass filtered.

This invention provides the above system, wherein the data acquisition subsystem comprises circuitry to digitize the electrogram signals to enable them to be stored in a digital computer.

As used herein, "digital computer" means an electrical device that performs mathematical operations on digitized data.

This invention provides the above system, wherein the data acquisition subsystem comprises the use of the difference or other function integrated circuit to determine the direction and velocity of the activating wavefront with respect to the multipolar ring catheter.

As used herein, "difference function" means to calculate a new value based on the subtraction of one value from another.

As used herein, "other function" includes but is not limited to LaPlacian filter or bandpass filter.

As used herein, "integrated circuit" means an electric circuit embedded on a silicon substrate which is usually sealed and can be accessed via standard electrical pins. As used herein, "integrated circuit" means an electrical circuit that is contained within a small silicon substrate with pin contacts and covered by a protective coating. It also can mean an electronic circuit, normally constructed from several of many electronics parts, that has been embedded onto a single small silicon matrix.

This invention provides the above system, wherein the data acquisition subsystem comprises the use of a maximum or averaging function integrated circuit to determine which pair of electrodes of the multipolar ring catheter lies parallel to the direction of propagation of the activating wavefront.

As used herein, "maximum function" means to identify a value based on finding the largest of a set of values.

As used herein, "averaging function," means to calculate a new value based on taking the mean of a set of values.

As used herein, "direction of propagation of the activating wavefront" means the angle that the activating wavefront travels with respect to an arbitrary fiducial angle.

This invention provides the above system, wherein the processing unit comprises software and hardware for multipole electrodes and reentrant circuit features algorithms. In one embodiment, the algorithms are hardwired using integrated circuits for parallel processing. In another embodiment, the algorithms are downloaded to programmable logic array (PLA) integrated circuits or similar device for parallel processing. In a further embodiment, the algorithms are written in software code for serial processing using a microprocessor or parallel processing using multiple microprocessors.

As used herein, "software" means computer programs that are stored on a magnetic or other storage device which are retrieved by the computer microprocessor and stored temporarily in computer memory to perform mathematical or other operations.

As used herein, "hardware" includes but is not limited to electric circuits that are used to perform mathematical or other operations.

As used herein, "parallel processing" means to use an algorithm or algorithms simultaneously to calculate a set of numbers.

As used herein, "multipole electrode" means 2 or more electrodes embedded in a matrix material which are used in concert to obtain information from the heart.

As used herein, "programmable logic array (PLA)" means an integrated circuit that is designed to process a set of numbers based on an algorithm that is downloaded to the integrated circuitry.

As used herein, "downloaded" means to transfer an algorithm written in computer software to the transistor circuitry of the programmable logic array.

As used herein, "software code" means the computer programs and data which are stored in computer memory for temporary storage or on a storage device for permanent storage.

As used herein, "serial processing" means the calculation of a set of numbers sequentially.

As used herein, "microprocessor" means an integrated circuit with the capability to process data based on collections of computer algorithms known as computer programs.

As used herein, "multiple microprocessors" means to use more than one microprocessor in tandem, with the same computer algorithms working simultaneously on each microprocessor, so that a set of numbers can be calculated at the same time, one on each microprocessor.

This invention provides the above system, wherein the display/guidance subsystem displays the conduction velocity and directional information determined based on electrogram signals obtained from the multipolar electrode.

As used herein, "directional information" means any numerical data that provides the angle between two points on the surface of the heart.

As used herein, "conduction velocity" means the speed or rapidity in millimeters per millisecond with which the activating wavefront travels through a given area.

As used herein, "multipolar electrode" means the several individual metal electrodes that are used in the circular electrode array.

This invention provides the above system, wherein the direction of the slow conduction zone with respect to catheter location is determined based on measurements made using the PLATM algorithm.

As used herein, "slow conduction zone," means that portion of the central common pathway with abnormally slow conduction, which is usually coincident with the narrowest width of the central common pathway.

This invention provides the above system, wherein the location of block lines is determined based on measurements made using the ATM algorithm.

As used herein, "central common pathway" means the portion of a reentrant circuit, which is protected by two bounding block lines.

As used herein, "block lines" means the curvilinear areas on the surface of the heart where the activating wavefront conducts slowly or not at all.

This invention provides the above system, wherein the location of the entrance and exit to the central common pathway is determined based on measurements made using the NATM algorithm.

As used herein, "entrance to the central common pathway" means the boundary at which the activating wavefront first enters the central common pathway.

As used herein, "exit to the central common pathway," means the boundary at which the activating wavefront first leaves the central common pathway.

This invention provides the above system for locating the narrowed width of the central common pathway based on the center of mass algorithm.

As used herein, "center of mass algorithm" means a group of arithmetic and logical instructions which compute the mean XY position from a group of XY positions.

This invention provides the above system comprising a system of symbols such as shaded and textured shapes to denote features of the reentrant circuit on the real-time display map.

As used herein, "system of symbols" means a group of alphanumeric or other characters, each of which has a certain predefined meaning.

As used herein, "shaded or textured shapes" means patterns produced by lines, dots, and other marks to convey the surface area and boundaries of reentrant circuit features.

As used herein, "features of the reentrant circuit" means the components of a reentrant circuit including the central common pathway, block lines, slow conduction zone, narrowest width region, entrance and exit to the central common pathway, and pivot points.

As used herein, "pivot points" means the points at the ends of the block lines around which the activating wavefront pivots as it propagates from one side of the block line to the other.

This invention provides the above system comprising a system of symbols such as arrows and angles used to denote distance and directional information pertaining to the location of reentrant circuit features with respect to the location of the catheter on the real-time display map.

This invention provides the above system for ablating the heart to stop ventricular tachycardia when the pattern of reentry is that of a single loop or of multiple loops.

This invention provides the above system for ablating the heart to stop ventricular tachycardia when the lines of block around which the activating wavefront traverses are anatomical or partly anatomical and partly functional rather than wholly functional.

This invention provides the above system for ablating the heart to stop ventricular tachycardia when the pattern of reentry is intramural or transmural.

This invention provides the above system for pinpointing sites or specific areas for drug delivery.

This invention provides the above system to detect and localize pathologic conditions in the heart, brain, lung, gastrointestinal system and musculoskeletal systems.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Experimental #1

A. MATERIALS AND METHODS

1) Canine Model of Myocardial Infarction

Myocardial infarction was produced by ligating the left anterior descending coronary artery (LAD) near its origin in mongrel dogs (8). After four days, the dogs were anesthetized for the electrophysiologic study with pentobarbital sodium (20–30 mg/kg), the chest opened via a mid-sternal incision, and a multielectrode array sutured onto the anterolateral surface of the left ventricle. Catheters were placed in the femoral vein to administer fluids and in the femoral artery for measurement of blood pressure, and standard limb lead ECGs were recorded.

2) Signal Acquisition

Two different mapping electrode arrays, approximately 12×7 cm, were used in different experiments for recording electrograms from the epicardial border zone of the infarct (8). One consisted of 292 and the other 312 bipolar, 1 mm silver disc electrodes embedded in a latex material. The poles of each electrode pair in the 292 electrode array were spaced 2 mm apart and the distance between bipolar pairs was 5–10 mm. The poles of each electrode pair in the 312 array were spaced 3.2 mm apart and the distance between bipolar pairs was 4.8–6.4 mm. Both arrays also contained bipolar stimulating electrodes, at the basal and lateral margins and in the center. Stimulating electrodes were also sutured onto the right ventricle adjacent to the LAD.

For the experiments using the 292 electrode array, data was acquired from 196 electrodes simultaneously, selected by a switch box (19), with a 196 channel mapping system that has been described previously (8). Signals were amplified, multiplexed, bandpass filtered (10 Hz–1 KHz), and digitized (8 bit resolution at 2 KHz). Data was acquired from the 312 bipolar electrode array using a 320 channel mapping system with an analog bandpass filter of 15 Hz–500 Hz. The signals were digitized at 1 KHz and a voltage resolution of 16 bits. All digitized signals were recorded on an Ampex PR2230 wide band PCM tape recorder along with ECGs, blood pressure, stimulus pulse, and voice annotation on FM channels.

3) Experimental Protocol

Single or double premature stimuli (2 msec duration, 2–4 times diastolic threshold) were delivered during basic drive of the ventricles from each of the 4 stimulation sites to initiate ventricular tachycardia (8). Stimulation from the center of the recording array was used to determine the orientation of the myocardial fibers in the epicardial border zone (8,19). Only monomorphic ventricular tachycardias are included in this study.

4) Analytical Methods a) Activation Marking and Mapping:

Activation maps of reentrant circuits in the epicardial border zone were constructed from electrogram activation times. Our methods for determining activation times, drawing isochrones, designating regions of conduction block and constructing activation maps have been described in detail (8,19).

b) Adaptive Template Matching (ATM):

Dynamic, beat-to-beat changes in electrogram morphology during tachycardia were quantified by applying an adaptive template matching (ATM) approach. (20)

As used herein, the "ATM Algorithm" can be described briefly as a way to adaptively update multiple weights for optimal overlap of a template with an input signal using the estimated mean square error (MSE) criterion. The weight update equation for one weight is given by[20]:

$$w_{i+1} = w_i + \mu \Sigma_{k=1}^{N} [\epsilon_k (y_k^+ - y_k^-)] \text{ for i=1 to P} \quad (A1.1)$$

where convergence to the minimum MSE, which provides best overlap of the signals, is approximated to be complete at P=500 iterations, the estimated signal $y_k$ is formed by weighting the input signal $x_k$ by $w_i$ during iteration i, $y_k^+ - y_k^-$ is an estimate of the derivative of $y_k$ using finite weight differences $w_i + \Delta w_i$, and $w_i - \Delta w_i$ for weighting $x_k$ to form, respectively, $y_k^+$ and $y_k^-$, $\mu$ is a coefficient of convergence, the residual error $\epsilon_k$ is the difference $d_k - y_k$ between the template $d_k$ and the estimated signal $y_k$, and N is the total number of discrete sample points used for template matching. Equation A1.1 was used to separately compute the weight update for the ATM weights of scale (amplitude and duration) and shift (phase lag and average baseline). The MSE, in addition to being the criterion for adaptive weight update, also provided a measure of the similarity in shape between the template electrogram and the weighted input electrogram following convergence of the weights. The MSE can be approximated as[20]:

$$MSE \approx 1/N \Sigma_{k=1}^{N} [\epsilon_k] \text{ for k=1 to N} \quad (A1.2)$$

The coefficient of convergence (in Equation A1.1 was first estimated for each electrogram channel according to the estimated energy of the signal in accordance with the principles of adaptive signal processing [20]. The mean MSE over all cardiac cycles was then computed using this approximation. However, the precise magnitude of the convergence coefficients effects convergence of the weights. If the coefficients are too small then the ATM weights will never reach the values necessary for optimal overlap of template with input electrograms whereas if they are too large the ATM weights will overshoot the optimal values. An intermediate value of convergence coefficient magnitudes will generate the optimal ATM weighting for best overlap of the template with the input electrogram, and these intermediate values were computed as follows. All four estimated convergence coefficients were scaled by 0.98 times their initial values, and the mean MSE over all cardiac cycles was recomputed. If the mean MSE decreased then the convergence coefficients were scaled again to 0.96 times their original value, whereas if the mean MSE increased they were scaled to 1.02 times their original value. This process was continued until the scale of the convergence coefficients produced the minimum mean MSE over all cardiac cycles. This was done separately for all electrograms and all episodes of tachycardia.

From the first 10 QRS complexes following ventricular tachycardia onset, a QRS complex was selected during which electrograms served as the template (FIG. 1, QRS #6). The template QRS complex had to have the same morphology as the remainder of the tachycardia and the shape of the template electrograms had to be relatively constant for the next few cardiac cycles as determined by visual inspection. The template consisted of a specified discrete time interval, k=1 to N, which was fixed at N=100 discrete signal data points (100 msec) for all experiments in this study, that encompassed the electrograms from all recording sites (FIG. 1, template time window (T) indicated by thick bordered rectangles). The window was centered on the largest positive or negative peak for each electrogram.

Input electrograms for ATM matching came from all recording channels during each of 50 subsequent cardiac cycles following the template during ventricular tachycardias. A given input signal window, like the template window, was centered on the largest positive or negative peak of the electrogram (FIG. 1, thin bordered rectangles indicate window for first input electrograms (I)). The windowed intervals, also initially 100 discrete signal data points (100 msec), but scaled by the ATM duration parameter (see below), were chosen to capture activation at all sites for all cardiac cycles, yet remain below the shortest cycle length so that only one cycle of activation was matched at a time.

The template for each electrogram was adaptively matched with the corresponding input electrogram interval, for all 50 successive cardiac cycles, j=1 to M of the same signal. The digitized electrograms from each recording channel for each subsequent cycle of the tachycardia were overlaid on the template for that channel and changed adaptively until the best fit to the template was obtained. The fiducial time for initial overlap of template with input electrograms was determined by first finding the extremum points (maximum or minimum during each cardiac cycle) in a representative electrogram with high signal-to-noise ratio and with a uni- or biphasic deflection. The fiducial time for electrograms from other sites were then determined using an automated algorithm as follows. For each cardiac cycle at each site, the extremum point within (0.5 cardiac cycle from the reference electrogram fiducial time was defined as the electrogram fiducial time for that cycle. These input electrogram extrema points, for each site, were then phase aligned with the extremum point of their respective templates based on the fiducial times, for initial overlap during each cardiac cycle prior to adaptation of the ATM weights. The estimated signal ($y_j$), which is the signal that results after the input electrogram is weighted, is a function of the input electrogram ($x_j$) and the parameter weights ($w_i$) during iteration (i) of the adaptive weight update that are used to change the fit (further details about the ATM algorithm are given in the Appendix). The parameters of scale (amplitude and duration) and shift (average baseline and phase lag) were used to adjust the input electrogram, $x_j$, to form the estimated signal $y_j$ that results from template matching. The equations used to update the weights are based on the estimated mean square error (MSE) (21) (see Appendix 1). For ATM, amplitude is considered to be the height of the signal averaged over the entire signal. The amplitude parameter (a) is unitless and is expressed as the ratio of the input signal amplitude to the template amplitude in mV. The duration parameter (d) is also a unitless ratio and is used to contract or expand the input signal by scaling the time base. For an input signal originally sampled in discrete time with period T, for contraction or expansion it is resampled by linear interpolation with a period $T^1=T*d$. If d is less than 1.0 it expands, if d is greater than 1.0 it contracts, and if d is unity there is no change. The phase lag (p) is the average time difference (msec) of all electrogram features of the input signal relative to corresponding features of the template, when they are overlapped. A change in the phase lag (p) means that the time of occurrence of all signal features (both peaks and isoelectric intervals) are shifted in time relative to the template by an equal amount.

For some statistical calculations, the electrogram phase parameter was expressed as the cycle to cycle difference in phase which can be considered to be a local cycle length (LCL). At any given electrogram recording site, the LCL can vary independently of the tachycardia cycle length as measured from the ECG. The average baseline (b) is defined as the average vertical level of the signal relative to isoelectric (0) in mV. Thus both peaks and isoelectric segments of the signal are shifted by the amount of the average baseline parameter. The ATM parameters of amplitude, duration, average baseline and phase lag scale and shift the signal linearly. Because these transformations are linear, they do not affect the relative angular and geometrical relationships which constitute the "intrinsic shape" of the signal (16) and which are invariant to linear scaling and shifting. Given two signals, if when they are scaled and shifted for best overlap, they become exactly coincident, then those two signals have precisely the same intrinsic shape. Otherwise, they do not have the same intrinsic shape.

FIGS. 2A–D provides an example of ATM matching with arbitrary initial weighting of the input signal. Only the 100 data point matching intervals are shown. Initially (Panel A), there is some overlap between the input (thin trace) and template (thick trace) signals but the input signal has a much larger amplitude and a greatly increased duration relative to the template. Due to its long duration, the input signal is not entirely contained within the matching window. For best overlap, the input signal amplitude must decrease, the duration must contract, the phase must be shifted to the left, and the average baseline must move upward. After 5 iterations, there is a much improved match between the two signals (Panel B). This occurred by decreasing the amplitude of the input signal from a=2.00 to a=1.53, compressing the duration from 1/d=1.67 to 1/d=0.88, shifting the signal to the left by 40.62 sample points (p=−2.29) (phase lag), and shifting the average baseline upward slightly by 0.01 volts (b=−0.24). After 25 iterations, with further parameter adjustment, there is a closer overlap of the signals (Panel C). After 500 iterations the weights provide a very close overlap of the template and input signals (Panel D). It is considered that at iteration 500, the weights approximate the optimal weighting (see below). Thus these weights at iteration 500 are recorded as the ATM weights which provide the best overlap of the signals. Matching is done for each electrogram in every tachycardia cycle. In this example the fit for the selected cycle is almost exact because the intrinsic shapes of the template and the input signal are nearly the same. Shape, however, might change for other cycles.

FIGS. 2E–H provides an example of ATM matching when the intrinsic shapes of the template (thick trace) and input (thin trace) signals are different (Panel E, initial weighting). Much of the weight changes occur during the first 25 iterations (Panels F and G). The overlap of template to input signals is considered to be optimal after 500 iterations (see below) (Panel H). However, perfect overlap does not occur because the intrinsic shapes of the two signals differ. Small-scale signal processing artifacts might also lead to incomplete convergence but for simplicity it was assumed that the effects averaged out from cardiac cycle to cycle. Large-scale signal processing artifacts (60 Hz line interference and amplifier noise) which made the signal to noise ratio less than 1.0 did occur on a few electrogram channels and these signals were not quantified by ATM.

A generalized form of the Widrow-Hoff least mean squares algorithm (LMS) was used to update the weights $w_i$ (parameter magnitudes) during each iteration, i=1 to P (20). Differences in intrinsic electrogram shape (the shape of the electrogram following normalization of the shift and scale parameters) were measured using the estimated mean square error (MSE) on the P=500th iteration of the weight update. As described above and illustrated in FIG. 2, the 500th iteration of the adaptive weight update was chosen as the stopping point to approximate the optimal solution for best overlap of the signals, based on the estimated MSE performance index (21).

Each of the ATM parameters was summarized in the form of statistical variance maps to represent cycle to cycle temporal variation in electrogram morphology at each recording site during a ventricular tachycardia. The variance of each of the parameters determined by ATM for each electrogram channel was computed over all cardiac cycles in the ventricular tachycardias that were analyzed. The variance of a given ATM parameter is defined as the sum of squares difference between the mean parameter value and the individual parameter value for each cardiac cycle (22). Five sets of variance measurements (amplitude, average baseline, phase lag, duration, and MSE at all recording sites were generated. Additionally, the normalized mean variance of the five ATM parameter variances was computed; first, the ATM variances or other weight variabilities at each site for each parameter was normalized (mean of zero and unity variance), then, the mean of the normalized data at each site using all five parameters was computed. Three dimensional variance maps generated from the data consisted of the variances for all sites for a single parameter plotted on a digital grid where the X and Y axes denoted the spatial position of the recording electrode, and the Z axis denoted the magnitude of the variance (a positive quantity). The digital grid spatial resolution was greater than either of the multielectrode arrays to reduce the error between the true position and the digitized position of the bipolar electrodes. For the 292 electrode array (XY dimensions of 6.8×13.6 cm) a 68×68 digital grid size was used so that each digital pixel represented a 1 mm×2 mm surface area, for the 312 electrode array (6.4 cm×12 cm) each pixel represented a 1 mm×1.5 mm surface area. Each bipolar electrode was projected to the nearest square pixel of the digitized grid. Piecewise bilinear interpolation was used to provide continuity to the relationships between neighboring electrode sites. Bilinear interpolation is a linear interpolation in two dimensions, which for ATM mapping is along the X and Y spatial coordinates. The value of an interpolated pixel was a combination of the values of the four nearest pixels in the X and Y directions. The result of this mathematical operation was a spatial low pass filtering or smoothing of the Z axis magnitude along the X and Y coordinates. For each of these maps, the Z axis scale was adjusted to fit the data so that any peaks of high variance would be apparent. The variance at each site was normalized using an estimate of the signal energy (viz., the mean of the sum of squares of the digital signal for the set of all electrogram input signals for that site) to render the variance independent, to a first approximation, of site to site differences in signal amplitude. Quantification of the association of variances with functional lines of block bounding the central common pathway of "figure of eight" reentrant circuits (8,17,19) was then computed by ranking peaks (22). The lines of block during each episode of tachycardia were projected onto the variance maps from the activation maps so that they would be located at the same electrode sites. Then, the sum of the heights of the highest 10 variance peaks which resided within 5.5 mm (the mean inter-electrode spacing) of the position of a line of block was computed (x). The sum of the heights of all of the highest 10 peaks was also computed (y). The ratio x/y times 100 was taken as the percent association of variance peaks with functional lines of block.

B) RESULTS

1) Activation Patterns During Ventricular Tachycardia

Fourteen monomorphic ventricular tachycardias lasting 12.4 to 58.7 seconds (56–322 cycles) in twelve infarcted dog hearts, were analyzed for this study (Table 1).

TABLE 1

CHARACTERISTICS OF VENTRICULAR TACHYCARDIA

| Ep. | Start CL (msec) | Prol.RT (msec/cycle) | VT Dur to Term(s) | Type of Term. | Cyc to Term. |
|---|---|---|---|---|---|
| 1 | 200 | 0.295 | 24.8 | ST | 122 |
| 2A | 214 | 1.393 | 12.4 | ST | 56 |
| 2B | 215 | 1.459 | 14.4 | ST | 61 |
| 3 | 240 | 0.179 | 13.7 | ST | 56 |
| 4A | 255 | 0.345 | 14.8 | ST | 58 |
| 4B | 243 | 0.165 | 19.8 | ST | 79 |
| 5 | 199 | 0.222 | 12.8 | ST | 63 |
| 6 | 160 | 0.106 | 50.7 | ST | 274 |
| 7 | 204 | 0.373 | 55.1 | ST | 158 |
| 8 | 298 | 0.163 | 34.1 | OD | 112 |
| 9 | 167 | 0.087 | 58.7 | OD | 322 |
| 10 | 178 | 0.085 | 52.9 | OD | 272 |
| 11 | 196 | 0.062 | 50.2 | ST | 242 |
| 12 | 363 | 0.178 | 30.6 | OD | 84 |
| Mean | 224 | 0.365 | 31.8 | | 140 |

| Ep. | Array Sites | CCP Loc. | CCP Dir. | CCP Min. Wi. (mm) |
|---|---|---|---|---|
| 1 | 196 | LAD/Apex | Parallel | 7.3 |
| 2A | 196 | Cen/Lat | Diagonal | 8.0 |
| 2B | 196 | Cen/Lat | Diagonal | 8.0 |
| 3 | 196 | LAD/Apex | Parallel | 8.4 |
| 4A | 312 | Cen | Parallel | 13.6 |
| 4B | 312 | Cen | Parallel | 9.0 |
| 5 | 312 | Cen | Diagonal | 13.9 |
| 6 | 196 | Cen/Base | Parallel | 16.0 |
| 7 | 312 | Cen | Diagonal | 18.2 |
| 8 | 312 | Lat | Diagonal | 14.2 |
| 9 | 312 | Lat | Parallel | 23.6 |
| 10 | 312 | Lat/Apex | Parallel | 22.4 |
| 11 | 312 | Cen | Diagonal | 21.2 |
| 12 | 312 | Apex | Diagonal | 14.0 |
| | | | | 14.1 |

Figures 5A, 5B, 5C:
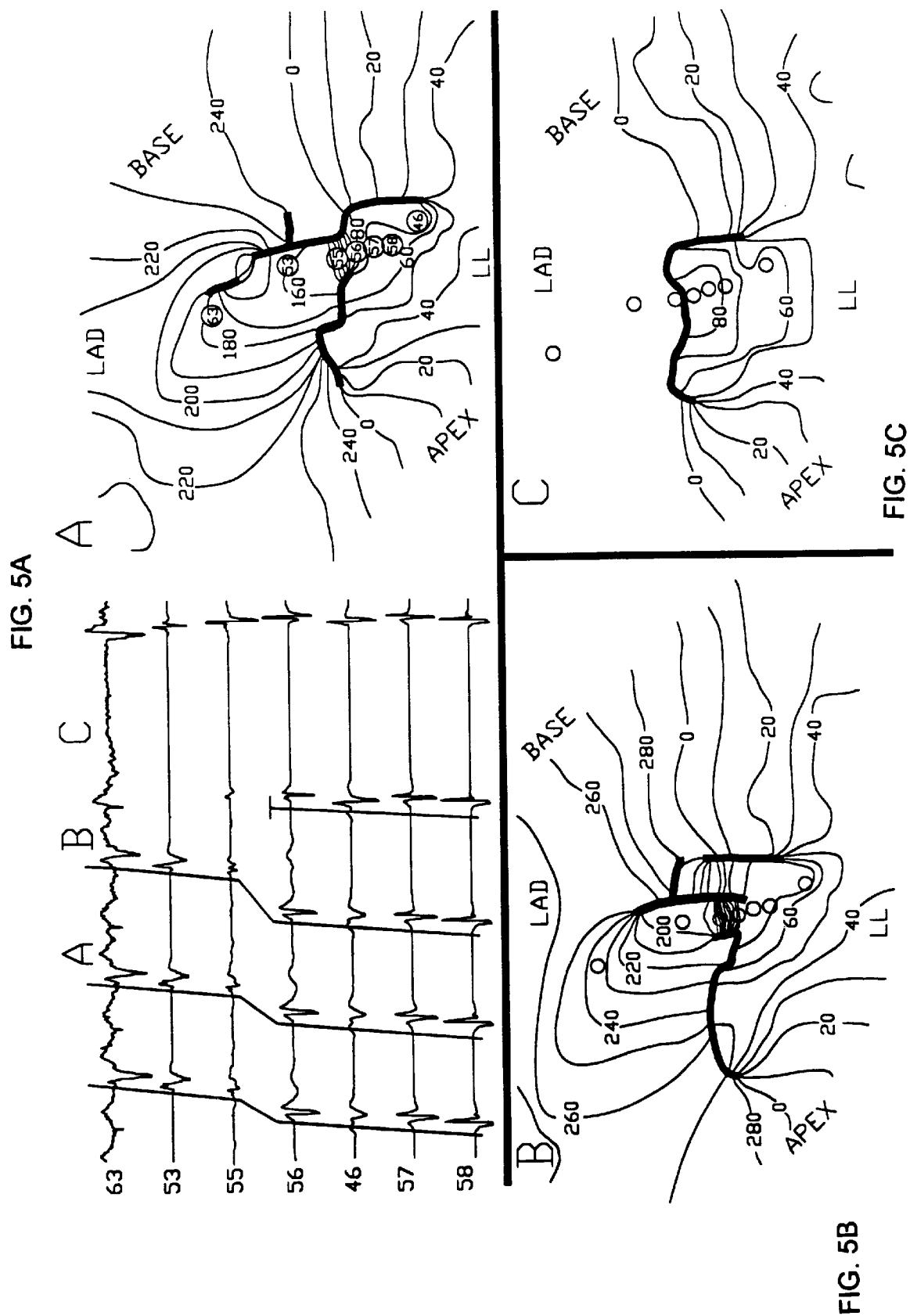
FIGS. 5A–5C Spontaneous termination of the tachycardia described in FIGS. 1 and 3. In Panel A is shown the activation map of the next to last complete cycle. Electrograms recorded from the central common pathway are shown at the left (recording sites indicated by circles on the map and labeled at the left of the electrogram traces) during the next to the last (A), and the last complete cycle (B) and block in the central common pathway (C). Panel B shows the map of the last complete cycle and Panel C shows the map during block in the central common pathway that terminated tachycardia.

Legend to Table 1 above:
Ep # = tachycardia episode; 2A and 2B occurred in the same heart as did 4A and 4B
Start CL = first tachycardia cycle length upon initiation of tachycardia
Prol. Rt = prolongation of cycle length rate from initiation to spontaneous termination
VT Dur to Term. = duration of tachycardia in seconds
Type of Term. = type of termination
ST = spontaneous termination
QD = termination by overdrive stimulation
Cyc to Term. = number of tachycardia cycles
Array Sites = electrode array used for mapping
CCP Loc. = location of central common pathway (CCP) on electrode array (Cen = center, Lat = lateral margin, LAD = LAD margin, and Apex = apical margin) (see FIG. 5)
CCP Dir. = direction of CCP with respect to the long axis of the muscle fibers
CCP Min. Wi. = width of CCP at its narrowest region just prior to termination Ten of the tachycardias terminated spontaneously after 12.4 to 55.1 sec while 4 tachycardias were terminated by overdrive stimulation after 30.6 to 58.7 sec (Table 1).

Complete reentrant circuits could be mapped in the epicardial border zone for all tachycardias. We describe the characteristics of the reentrant circuits prior to the electrogram analysis since they may have important influences on changes in electrograms that occurred.

Only tachycardias associated with reentry wavefronts rotating around two lines of block, resembling the "figure of eight" described by El-Sherif et al (17) are included in this study. FIG. 3 shows activation maps from one of the episodes of tachycardia which lasted 12.4 sec (56 cycles) (episode 2A in Table 1, ECG shown in FIG. 1). In panel A (cycle 15), the time window begins within the 0–10 msec isochrones where two wavefronts are propagating toward the lateral (LL) margin of the electrode array, one clockwise from the base and the other counterclockwise from the apex. These wavefronts merge after 50 msec and move towards the LAD margin (isochrones 50–180) between two long functional lines of block indicated by the thick black lines which were not present during sinus rhythm. This wavefront then divides into two, with one wavefront moving to the right and the other to the left around the ends of the lines of block to complete two circuits after 220 msec. The region activated between isochrones 50–160 msec is designated the central common pathway, the region between the functional lines of block that is common to both reentrant wavefronts. In this example, designation of the central common pathway is somewhat arbitrary compared to circuits where the two lines of block are parallel to each other (17) (see FIGS. 4, 6B, and 6D). The activation pattern appeared by eye to be stable throughout much of the tachycardia as shown by comparing cycles 25 (Panel B), 35 (Panel C), and 45 (Panel D) with cycle 15 (Panel A) in FIG. 3 although cycle length did prolong gradually (1.393 msec/cycle, Table 1). Cycle length prolongation was a characteristic of all tachycardias. FIG. 4 shows activation maps from a longer episode of tachycardia that lasted 55.1 sec (158 cycles) (episode 7 in Table 1) Panel A is the first cycle following the template. At the beginning of the time window, two wavefronts are moving toward the LAD margin, one in a clockwise direction from the apex (isochrones 0–30), and one in a counterclockwise direction along the base (isochrones 0–30). These wavefronts coalesce and move in the central common pathway, between two lines of functional block (thick black lines) back toward the apex-LL margin (isochrones 40–130). This pattern is essentially the same during cycles 15 (panel B), 35 (panel C) and 50 (panel D). Tachycardia cycle length also prolonged over the first 50 cycles but much less so than the tachycardia shown in FIG. 3 (mean of 0.373 msec/cycle, Table 1). The mean prolongation rate for all tachycardias was 0.365 msec/cycle with short lasting tachycardias (<30 sec) showing greater cycle length prolongation (0.580 msec/cycle) than longer lasting tachycardias (>30 sec, 0.151 msec per cardiac cycle).

In some of the tachycardias which terminated spontaneously, particularly those lasting less than 30 sec, significant changes in the activation patterns began to occur during the last 2–10 cycles prior to spontaneous termination. Although cycle length prolonged gradually throughout each of the tachycardias without changes in the lines of block, during the last few cycles a much greater prolongation of the cycle length was associated with changes in the lines.

FIG. 5 shows the last two complete cycles (cycle 55 in Panel A and cycle 56 in Panel B) and the spontaneous termination (Panel C) of the tachycardia described in FIG. 3. Slowing of activation in the central common pathway is evident by the increased number of isochrones in this region during cycles 55 and 56 and the increased time delay between electrograms recorded at sites 56 and 55 (electrogram traces are at the left in Panel A). The increasing delay of the wavefront between sites 56 and 55 approximately corresponds to the increase in the cycle length. The last cycle length prior to block (cycle 56, Panel B) increased by 42 msec from the prior cycle length (a change from 247 to 289 msec). Eventually the circulating wavefronts blocked near electrode 55 (Panel C and electrograms C at left of Panel A), at the horizontal thick black line. Block occurred near the region of the central common pathway with the narrowest width.

Figure 6F:
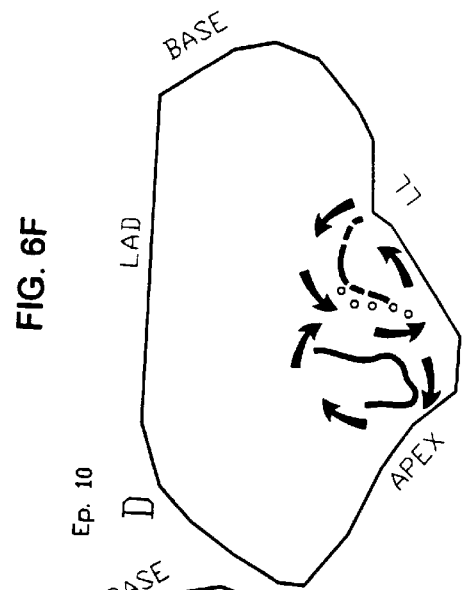
Figure 6E:
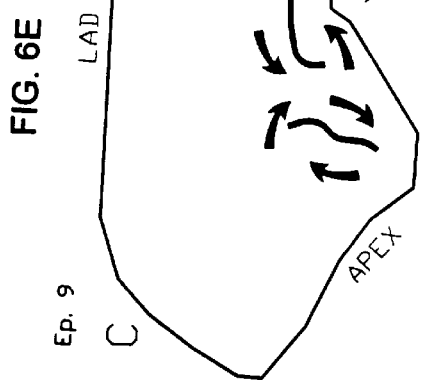
Figure 6D:
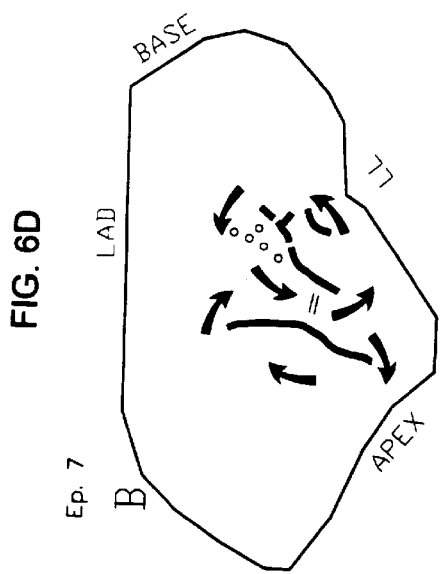

FIG. 6 shows the relative stability of the functional lines of block for six of the episodes of tachycardia. The figure also illustrates the variability of activation patterns, locations and orientation of the lines of block for these tachycardias (Table 1). Segments of lines of block which persisted throughout the tachycardia are indicated by the solid black lines, segments that occurred during the initial period and then later disappeared are indicated by the dashed lines, and new segments not present initially but which formed later are indicated by the circles. Often these new segments narrowed the central common pathway (Panels A, C, D and F) prior to spontaneous termination. Most of the slowing of activation which prolonged tachycardia cycle length prior to termination occurred in these narrowed regions as did conduction block which resulted in termination. The site where conduction block occurred in spontaneously terminating tachycardias is denoted by a double horizontal line. Changes in the functional lines of block were large in episode 2A and 4A, were smaller in episodes 3, 7 and 10 and did not occur in episode 9 (Table 1). In general, the location of the functional lines of block was more stable during the longer lasting tachycardias.

2) Changes in Electrogram Morphology During Ventricular Tachycardia

Figure 7A:
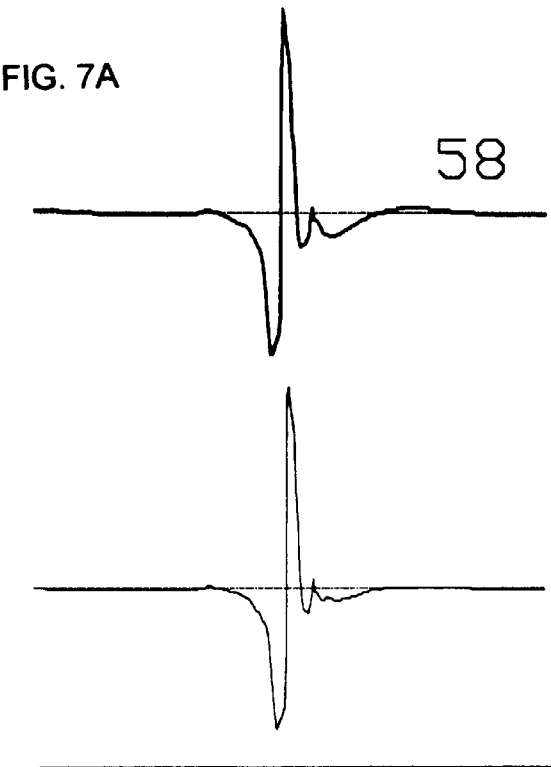
FIGS. 7A–D Comparison of electrograms recorded at four different sites in the reentrant circuit shown in FIGS. 3 and 5 during cycle 6 (the template, upper trace designated by thick line) with electrograms recorded at cycle 56 (an input signal, lower trace designated by thin line). The number at the left above the template trace in each panel is the recording site indicated in FIG. 5A. The dotted line is the zero volt level. The start of the template is at 100 msec, the end at 200 msec and it is centered at 150 msec. All input signals are centered so that their peaks occur at 150 msec (i.e., the initial phase weighting used for template matching). Panel A is site 58 of FIG. 5A. Panel B is site 55 of FIG. 5A. Panel C is site 63 of FIG. 5A. Panel D is site 46 of FIG. 5A.
Figure 7B:
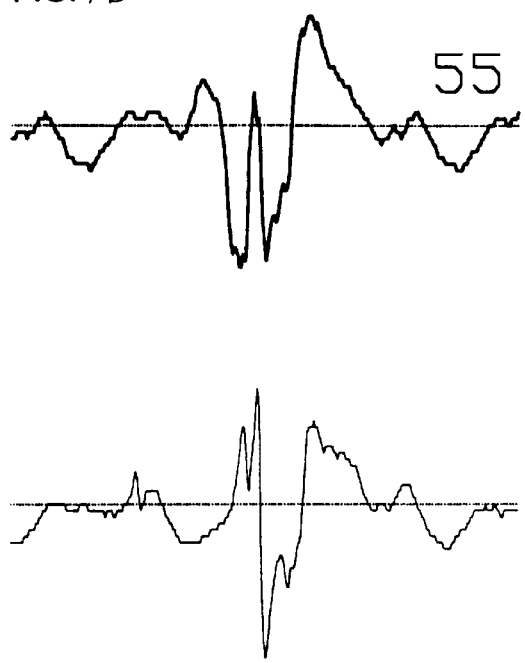
Figure 7C:
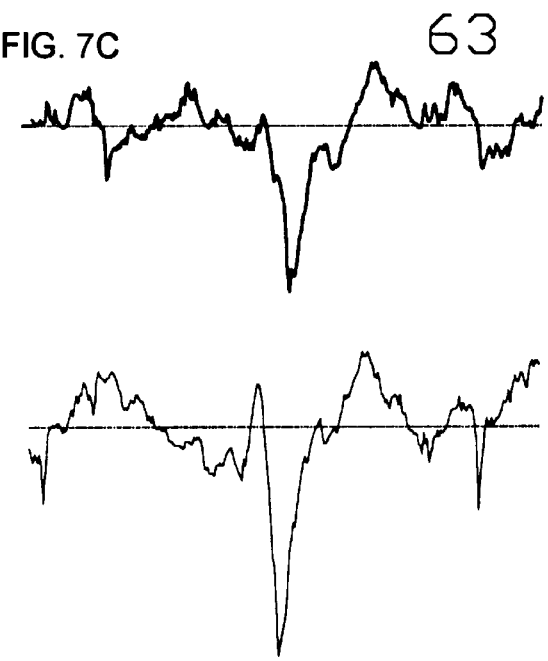
Figure 7D:
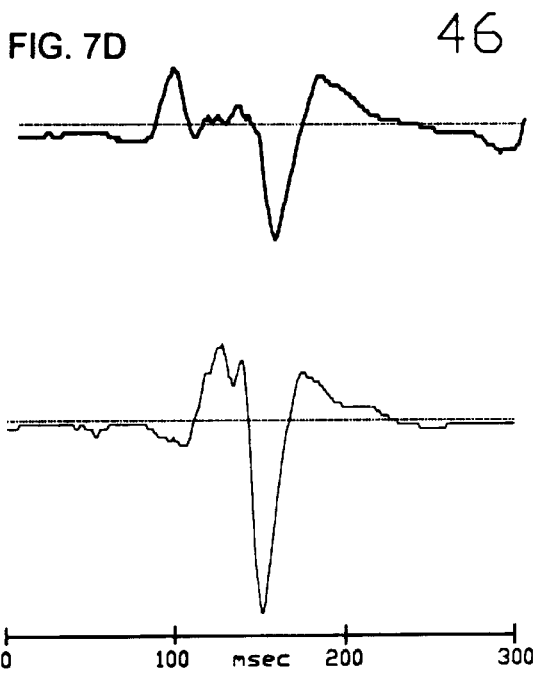
Figure 8A:
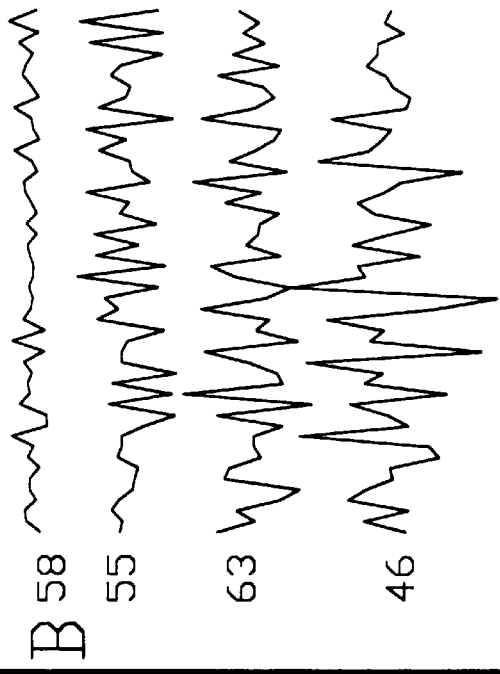
FIGS. 8A–8D Beat to beat changes in electrogram parameters used for ATM analysis from the four recording sites shown in FIGS. 5 and 7. The recording sites from FIG. 5 are indicated to the left of the traces. The abscissa is cycle number beginning at cycle 7 (the template was cycle 6). The ordinate is change in the parameter relative to the template (traces are offset). Panel A is amplitude, Panel B is phase lag, Panel C is duration and Panel D is MSE (intrinsic electrogram shape).
Figure 8C:
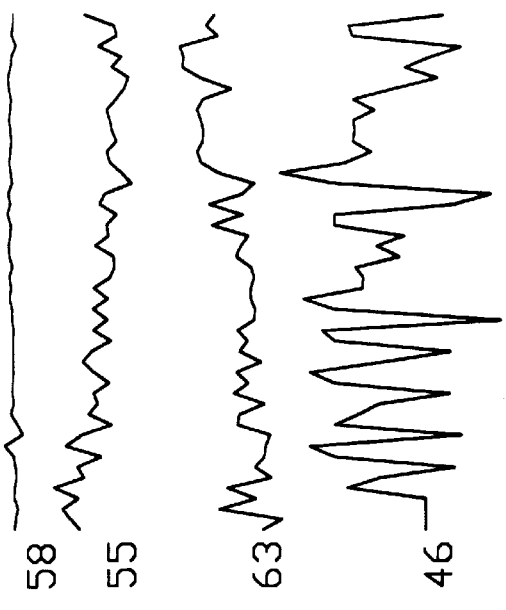
Figure 8B:
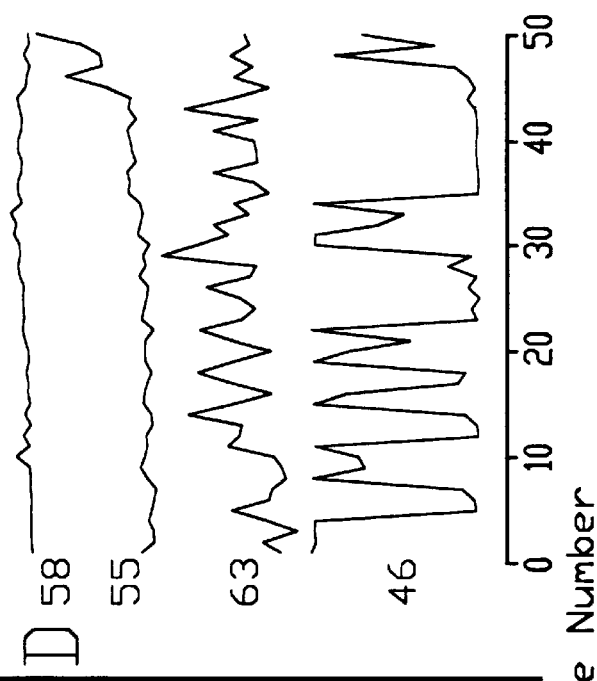
Figure 8D:
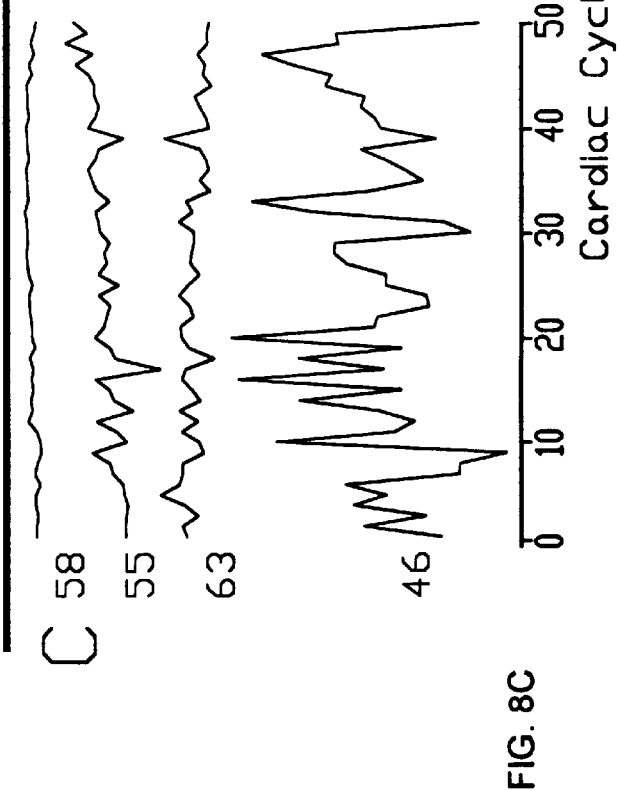

The changes that occurred in electrogram morphology during tachycardia that were quantified by ATM analysis were related to the different recording sites in the reentrant circuits and surrounding regions. FIG. 7 illustrates some of the changes in electrograms in the reentrant circuit causing the tachycardia (episode 2A) described in FIGS. 3 and 5 with initiation shown in FIG. 1. A three hundred millisecond window (greater than the cycle lengths of tachycardia) is shown. FIG. 7A shows that only slight changes occurred in the amplitude, duration, average baseline and intrinsic shape of an electrogram recorded at the entrance to the central common pathway (site 58 in FIG. 5) when input cycle 56 (bottom trace) is compared with the template (top trace, cycle 6). For an electrogram near the site of spontaneous termination in the central common pathway (FIG. 5B, site 55) (compare bottom input trace, cycle 56 with top template trace, cycle 6 in FIG. 7B) changes in amplitude and duration differ in different portions of this signal, contributing to a change in intrinsic shape and an increase in the MSE. There is also a net decrease in the average amplitude despite the similar size in the maximum negative-going peak and an increase in size of the central positive peak when measured by ATM analysis although these changes are not readily discernible by visual inspection. The duration and the average baseline increase as well. In an electrogram from a site at the exit from the central common pathway (FIG. 7C, site 63 in FIG. 5), the amplitude increases and the duration decreases slightly. The average baseline remains approximately constant. The intrinsic shape also changes, causing the MSE to increase. At a site adjacent to a functional line of block which subsequently shortens prior to termination of tachycardia (FIG. 7D, site 46 in FIG. 5), there is an increase in amplitude from cycle 6 to 56. Also, the small initial positive-going peak (double potential), caused by activation on the opposite side of the line of block, in template cycle 6 (top trace) shifts to the right by approximately 25 msec in cycle 56 (bottom trace) due to breakthrough at the functional line of block, causing marked changes in intrinsic electrogram shape (MSE).

Figure 4B:
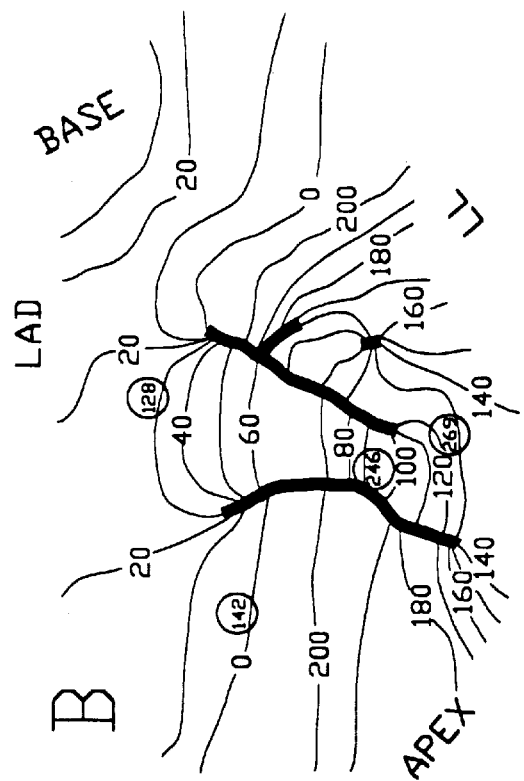
FIGS. 4A–4D Activation maps of a reentrant circuit causing ventricular tachycardia. In each panel is a representation of the electrode array. The margins at the LAD, base, lateral left ventricle (LL) and apex are labeled. Panel A shows the activation pattern during the template cycle; Panel B during cycle 15; Panel C during cycle 35 and Panel D during cycle 50. The small numbers in Panel A are activation times at each of the recording sites. Activation times have been omitted from the other panels. In Panel B, circles containing electrode numbers are referred to in the text. Isochrones are drawn at 10 msec intervals and are labeled with the larger numbers. Thick black lines designate regions of conduction block. Arrows point out the direction of wavefront propagation.
Figure 4D:
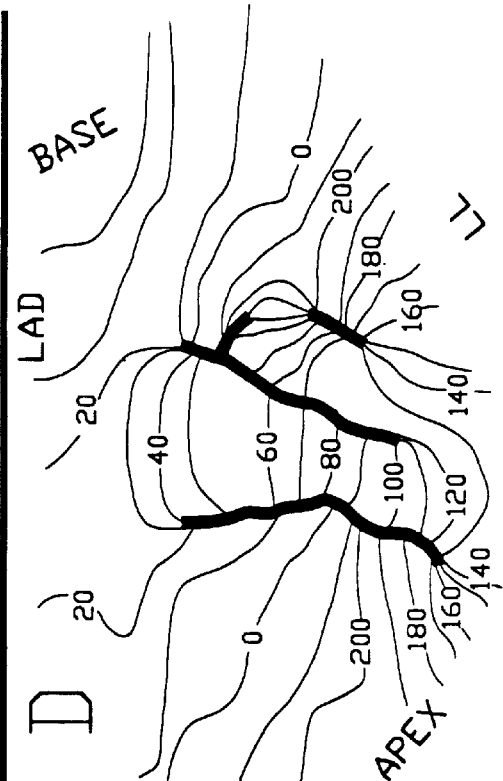
Figure 4A:
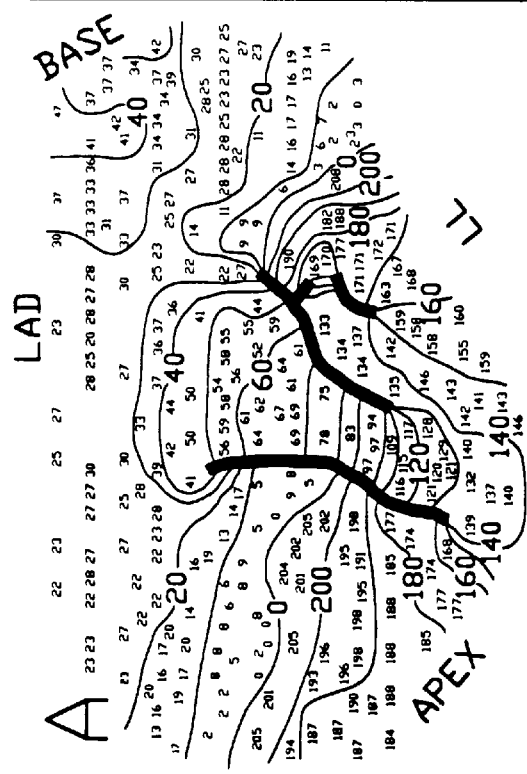
Figure 4C:
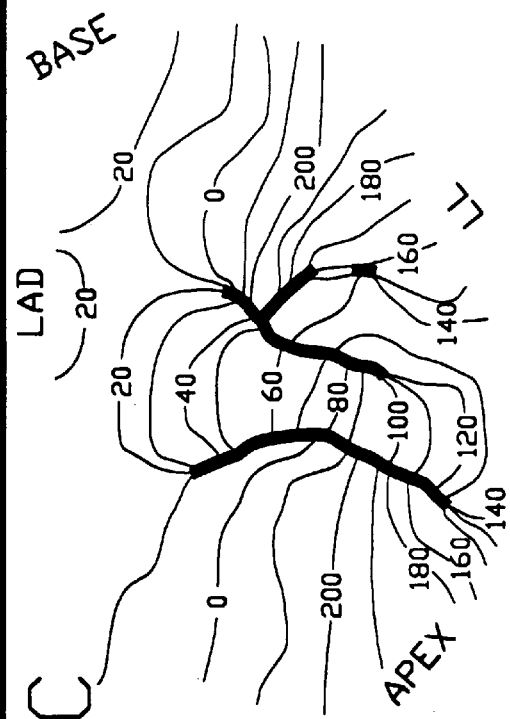

A plot of the time course of changes of the electrograms in FIG. 7, shows the variability in electrogram morphology during this episode of tachycardia that was quantified by ATM (FIG. 8). In FIG. 8A (amplitude changes), site 55 (spontaneous termination site) exhibits amplitude oscillations with an overall decrease in amplitude, site 46 (site near the line of functional block which broke down at the end of tachycardia) exhibits large amplitude oscillations, site 63 (near the exit from the central common pathway) exhibits small amplitude oscillations and an overall increase in amplitude and at site 58 (near the entrance to the central common pathway) very little change in amplitude can be seen. The changes in phase lag are plotted in FIG. 8B with oscillations of different magnitudes occurring at all recording sites. The largest oscillations occur at sites 46, 63, and 55. The duration parameter (FIG. 8C) also oscillates with the largest oscillations at site 46. Site 63 exhibits a slightly decreasing duration and site 55 exhibits an increasing duration. There is almost no duration change at site 58. The MSE (intrinsic shape) (FIG. 8D) oscillates at sites 63 and 46 and increases at sites 55 and 63, indicating that these electrograms undergo large changes in intrinsic shape. The gradual increase in MSE at site 55 indicates that a gradual change in intrinsic shape occurred there, until the last few cycles prior to spontaneous termination where the jump in MSE indicated that a large change in intrinsic shape occurred (see FIG. 7B which displays cycles 6 and 56). The large jump in intrinsic shape during the last few cycles at site 55 is likely due to the narrowing of the central common pathway during the last few cycles prior to spontaneous termination. The wild oscillations in MSE at site 46 are due to an alternating pattern of intrinsic shape change which occurred at this site. Also, during the last few cycles, a change in the line of block occurred near site 46 and the spacing of the double potential narrowed, increasing the MSE. There is much less change in electrogram shape at site 58. Thus, these graphs in FIG. 8 provide information about the time course and beat to beat changes in electrogram morphology for this short-lasting episode of tachycardia. FIG. 9 shows a similar plot for representative electrograms in a longer lasting episode of tachycardia during which the lines of functional block were more stable (episode 7 also shown in FIGS. 4 and 6D) to illustrate that beat to beat changes in electrograms were not entirely dependent on changes in the lines of block. The amplitude (panel A), phase (panel B), duration (panel C) and MSE (panel D) for the four recording sites located in FIG. 4B, are illustrated. The site outside the central common pathway and distant from the line of block (site 142) shows only very slight changes in these parameters over the 50 cycles. Likewise, site 128 at the entrance to the central common pathway distant from the functional lines of block shows only small changes. However site 246 which is adjacent to a functional line of block and site 269 at the exit of the central common pathway adjacent to a pivot point around the end of a line of block, both show marked oscillations, with the greatest overall oscillations at site 246. Similar graphs were constructed for all electrograms for all tachycardias and are the basis for the variance data described in the next section.

3) Variance Maps

Figure 10A:
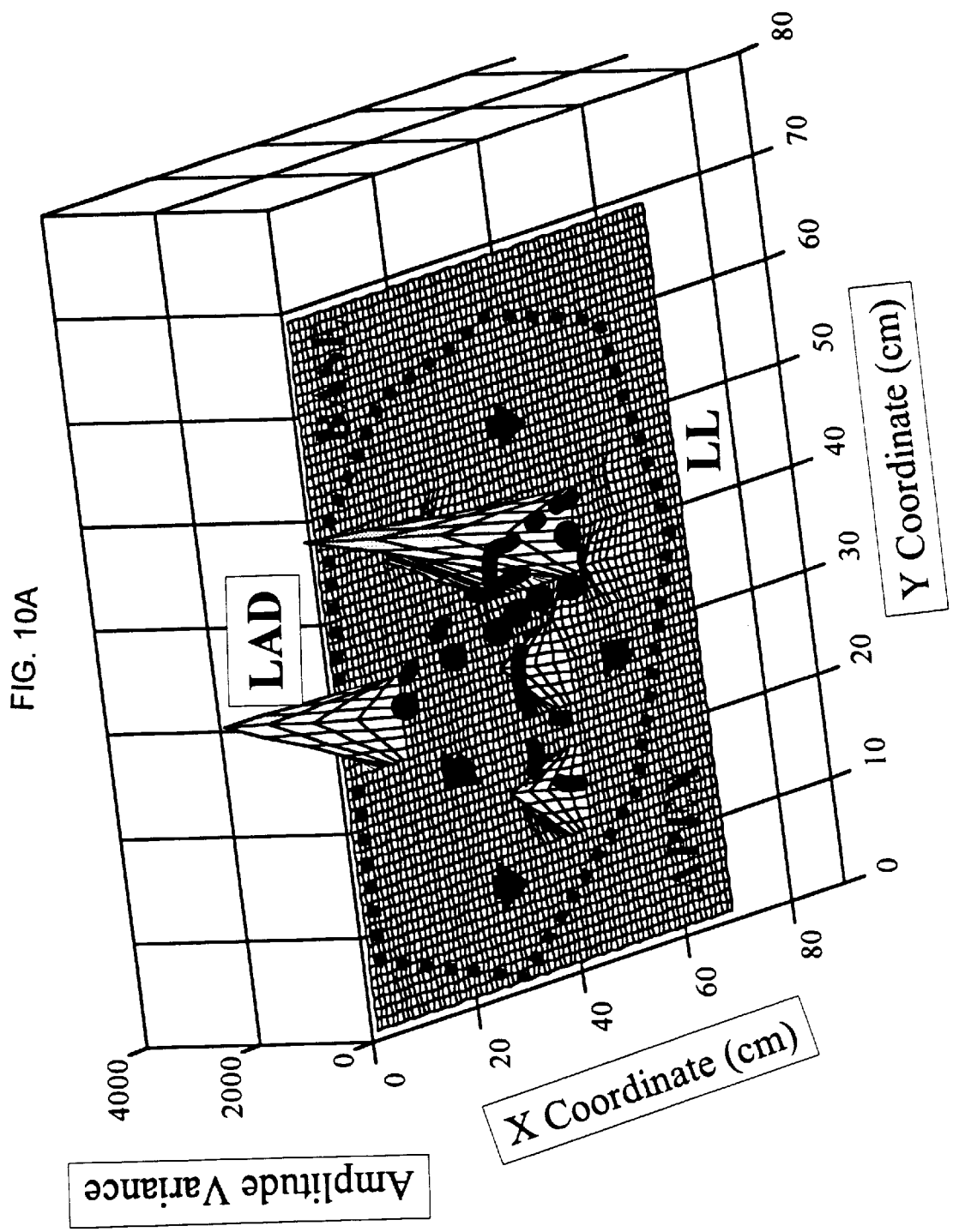
FIGS. 10–10B Panel A. Variance map that shows the magnitude of the variance (Z axis) for amplitude during tachycardia 2A (Table 2) at 196 recording sites plotted on the X and Y axes. The borders of the electrode array are outlined by the dashed red lines. The map is viewed from an azimuth of −10 degrees with respect to the viewing angle of FIGS. 3–6 and an altitude of 65 degrees. Overlaying the variance map is the location of the functional lines of block (thick black lines) in the reentrant circuit. The location of the seven electrode sites in FIG. 5 are denoted by red circles. The fourth circle in the circuit is the spontaneous termination site (see FIG. 5). Arrows show the direction of reentrant wavefront propagation. Panel B. Variance map that shows the magnitude of the variance (Z axis) for duration in tachycardia 2A (Table 2). The format is the same as for Panel A.
Figure 10B:
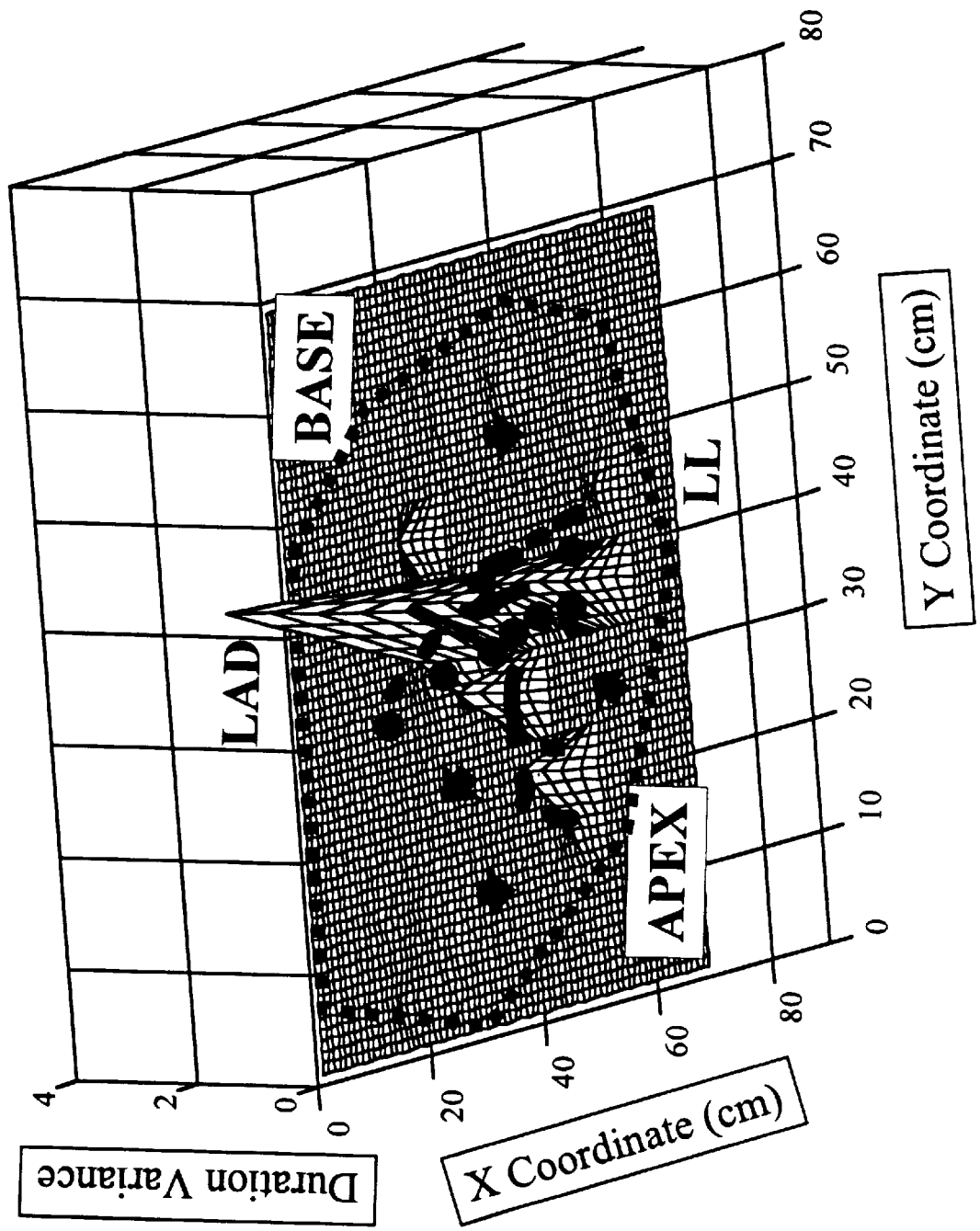

The changes in electrogram morphology during each tachycardia, as shown in FIGS. 8 and 9, were expressed as three dimensional variance maps. In the maps of amplitude variance (FIG. 10A) and duration variance (FIG. 10B) from tachycardia 2A (Table 1) (FIGS. 3, 5, 7 and 8), the largest variance peaks occur in proximity to the functional lines of block (thick black lines) that bound the central common pathway (92.0 and 96.7% of amplitude and duration variance peaks were associated with the functional lines of block, that is, they were at electrodes on either side of the lines of block (see Methods and Table 2)), indicating that electrograms recorded in these regions were intrinsically unstable and underwent more beat to beat changes than electrograms in other regions. In FIG. 10A, a large variance peak can be seen at X,Y coordinates (1.5, 6) not strictly adjacent to a functional line of block but at the end of a line of block that disappeared prior to termination (dashed lines) and in a region where the wavefront sharply turned in the circuit. Plots of MSE, phase lag, and normalized mean variance (not shown) had a 100.0%, 97.6% and 93.7% correlation for this tachycardia episode (Table 2). The parameter which showed the poorest correspondence for episode 2A was the average baseline, 78.4% (Table 2). The mean association of largest variance peaks with functional lines of block for all parameters for episode 2A is 93.1% (Table 2). In contrast, much of the region of the central common pathway exhibits minimal variance as well as regions in the outer pathways of the reentrant circuit (FIGS. 10A and B) indicating relative stability of ATM parameter variance there during tachycardia. In FIG. 10B, the variance peaks located adjacent to functional lines of block spill over into the CCP in some places but this is mostly caused by the interpolative procedure used to create the ATM maps. Occasionally, moderate dynamic changes in electrogram morphology occurred at a site which was not adjacent to a functional line of block, causing a medium-sized variance peak to appear on the ATM maps at the site location; this lowered the accuracy of the ATM method.

TABLE TWO

CORRESPONDENCE OF VARIANCE PEAKS
WITH LINES OF BLOCK DURING TACHYCARDIA

| Exp. # | Ampl. | Baseline | Phase |
|---|---|---|---|
| 1 | 97.0 | 73.2 | 50.2 |
| 2A | 92.0 | 78.4 | 97.6 |
| 2B | 93.6 | 52.9 | 85.4 |
| 3 | 95.0 | 75.7 | 100.0 |
| 4A | 100.0 | 100.0 | 100.0 |
| 4B | 84.6 | 100.0 | 94.0 |
| 5 | 100.0 | 88.7 | 77.0 |
| 6 | 89.7 | 100.0 | 100.0 |
| 7 | 94.5 | 46.2 | 86.9 |
| 8 | 97.5 | 93.4 | 100.0 |
| 9 | 76.4 | 81.2 | 51.6 |
| 10 | 100.0 | 91.0 | 70.0 |
| 11 | 83.8 | 95.1 | 85.5 |
| 12 | 100.0 | 96.3 | 82.9 |
| Mean | 93.2 | 83.7 | 84.4 |

| Exp.# | Duration | MSE | N-Mean | Mean |
|---|---|---|---|---|
| 1 | 78.7 | 72.0 | 87.1 | 76.4 |
| 2A | 96.7 | 100.0 | 93.7 | 93.1 |
| 2B | 100.0 | 31.7 | 85.3 | 74.8 |
| 3 | 89.6 | 92.9 | 92.3 | 90.9 |
| 4A | 91.2 | 96.1 | 93.0 | 96.7 |
| 4B | 83.7 | 94.5 | 83.8 | 90.1 |

TABLE TWO-continued

CORRESPONDENCE OF VARIANCE PEAKS
WITH LINES OF BLOCK DURING TACHYCARDIA

| 5 | 68.1 | 84.0 | 100.0 | 86.3 |
| --- | --- | --- | --- | --- |
| 6 | 100.0 | 87.8 | 100.0 | 96.3 |
| 7 | 93.4 | 99.1 | 82.2 | 83.7 |
| 8 | 93.2 | 94.5 | 94.8 | 95.6 |
| 9 | 60.0 | 41.4 | 77.3 | 64.7 |
| 10 | 92.2 | 74.9 | 71.7 | 83.3 |
| 11 | 100.0 | 93.3 | 93.0 | 91.8 |
| 12 | 87.2 | 68.5 | 92.0 | 87.8 |
| Mean | 88.1 | 80.8 | 89.0 | 86.5 |

Legend to table 2 above:
Exp. # = Tachycardia episode, corresponds to Table 1
ATM parameters are as follows:
Ampl. (amplitude)
Baseline (averaqe baseline)
Phase (phase lag)
Duration
MSE (intrinsic shape)
N-mean (normalized mean variance)

Figure 11A:
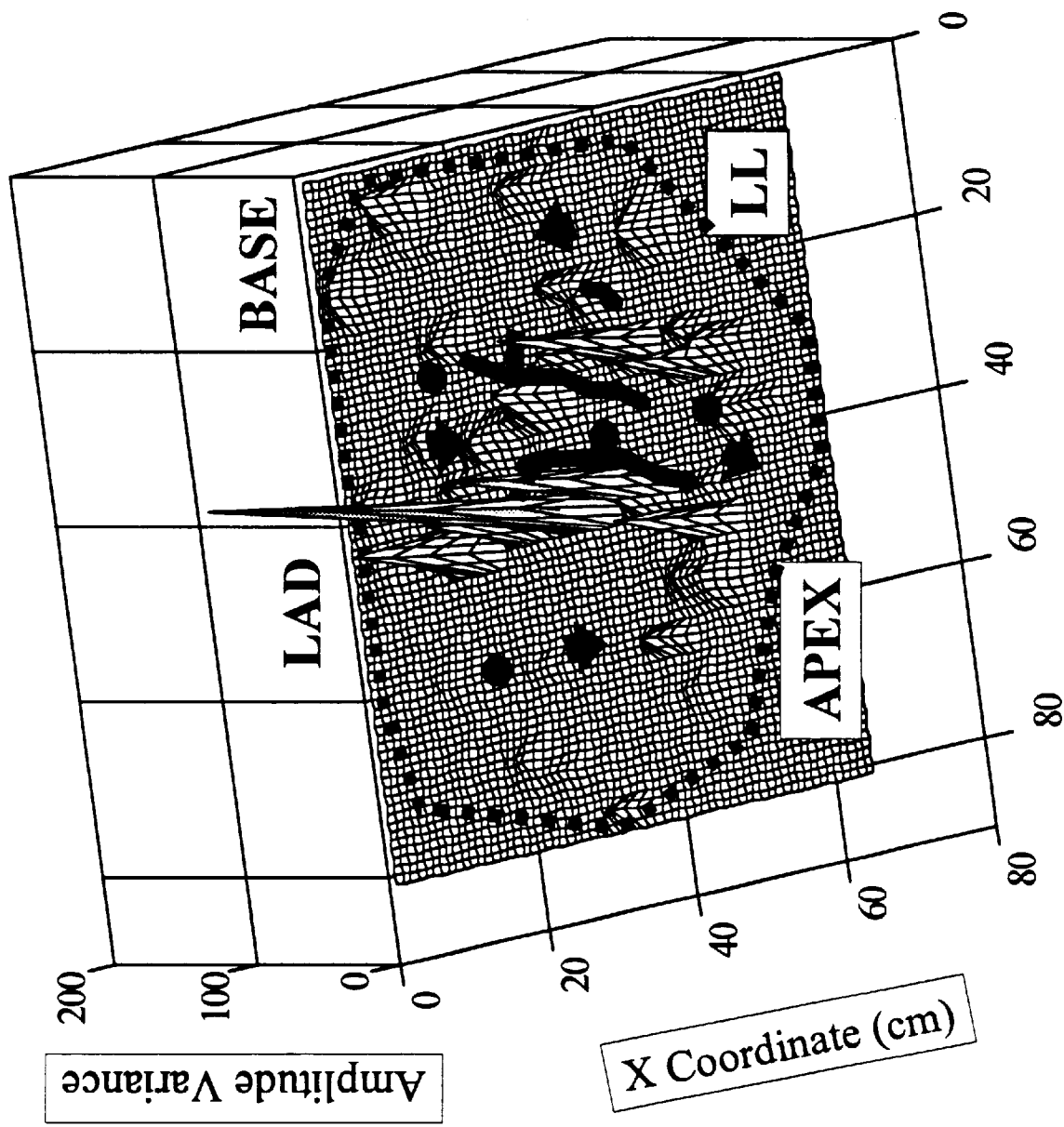
FIGS. 11A, 11B Panel A. Variance map that shows the magnitude of the variance (Z axis) for amplitude in tachycardia 7 (Table 2) (FIGS. 4 and 6D). Panel B. Variance map that shows the magnitude of the variance (Z axis) for phase in tachycardia 7 (Table 2). The format is the same as for FIG. 10.
Figure 11B:
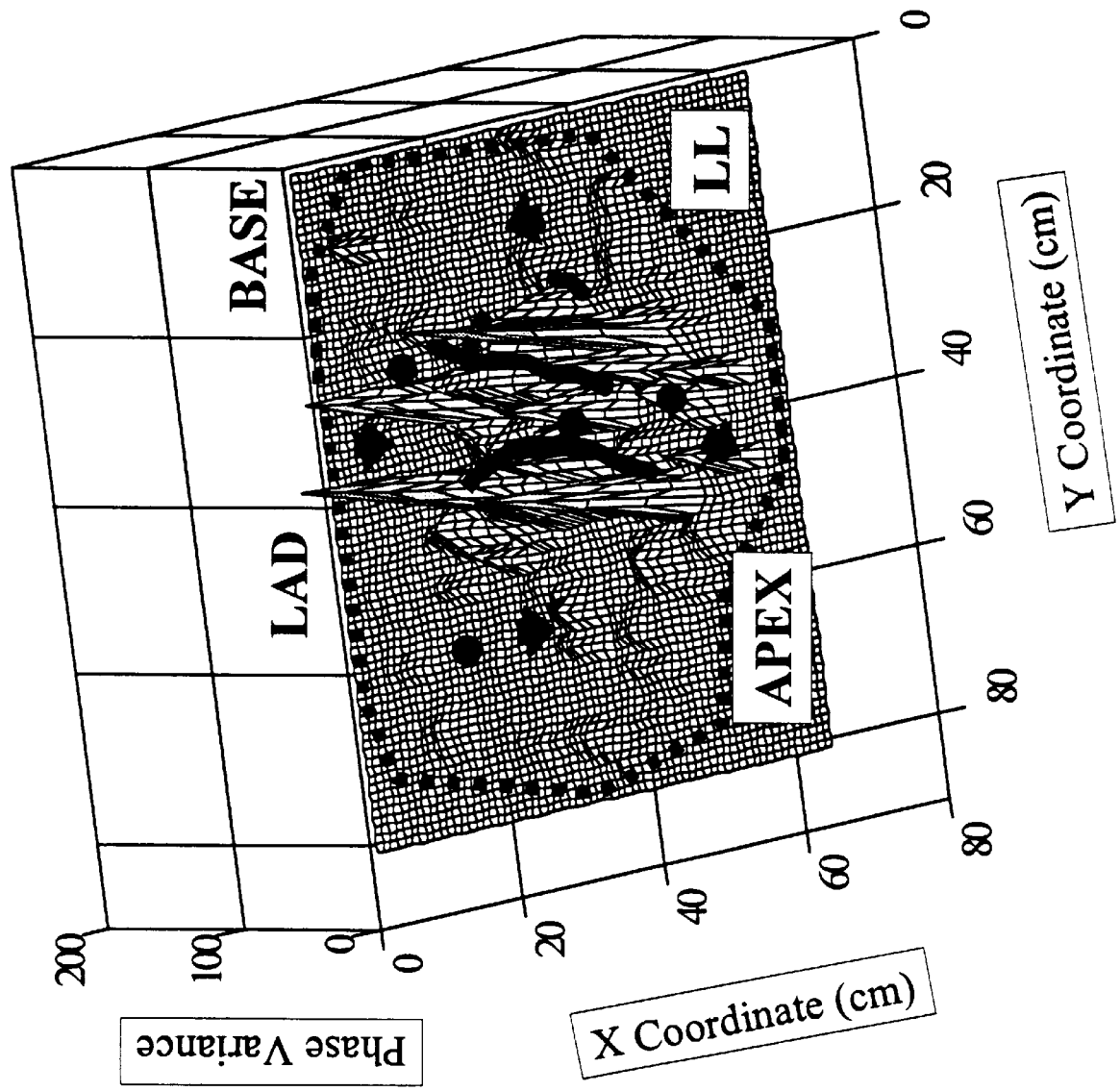
Figure 12A:
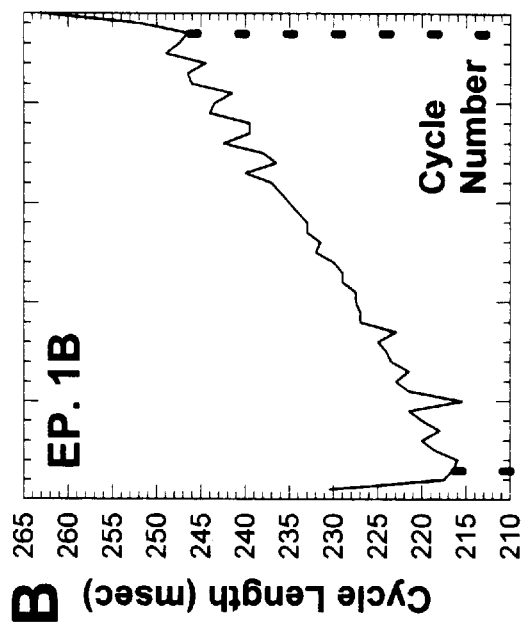
FIGS. 12A–12D The change in cycle length (CL) with cycle number for four episodes of VT. Relatively quiescent periods of approximately linear CL increase occur in all episodes with endpoints shown by the dashed lines. In episode 1A (Panel A) there is additionally a period of approximately linear decrease in CL followed by another period of increase. Large CL changes occur in each episode for a few cycles following onset, and just prior to spontaneous termination in episodes 1B and 2. Smaller oscillations of 4–5 msec occur during the quiescent periods of linear increase or decrease in CL. Panel A shows Episode 1A. Panel B shows Episode 1B. Panel C shows Episode 2. Panel D shows Episode 3.
Figure 12B:
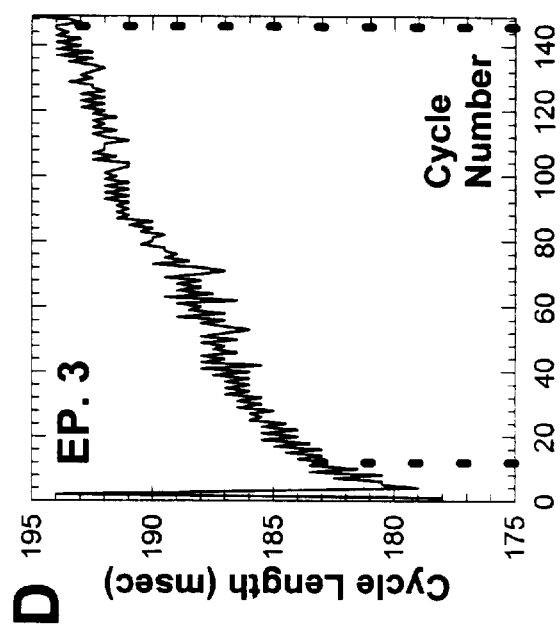
Figure 12C:
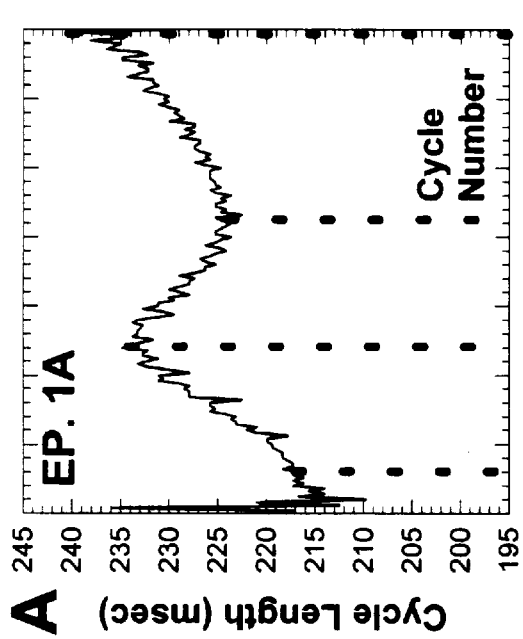
Figure 12D:
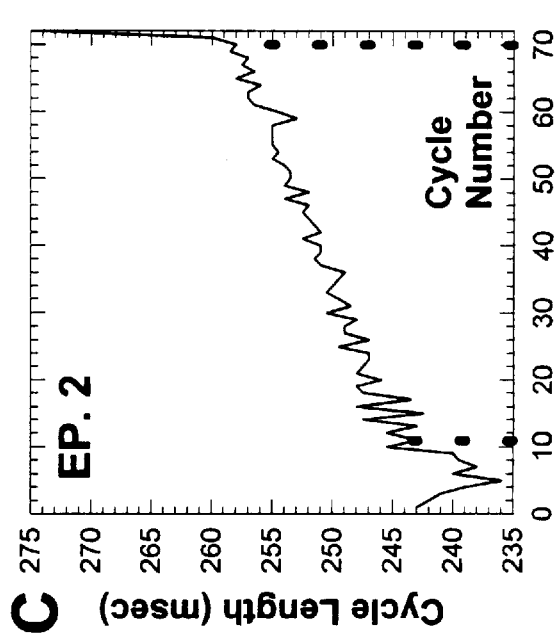

It might be expected that the largest variances would be associated with functional lines of block in the episode of tachycardia shown in FIG. 10 (episode 2A) because of the changes in the lines of block associated with tachycardia termination (see FIG. 6A). However, ATM measurements are weighted equally for all cycles, and ATM measurement changes during the last few cycles only affected ATM variances or other weight variabilities at a few sites. Similar relationships between variance peaks and functional lines of block were also found in tachycardias which had minimal changes in the lines of block independent of whether they were short-lasting so that cycle lengths near their termination were included in the ATM analysis such as episode 3 (FIG. 6B) or long lasting so that cycle lengths near termination were not included in the analysis such as episode 7 (FIGS. 4 and 6D) (see Methods; the template is from the first 10 cycles and 50 subsequent cycles were matched for each episode). A mean of 90.9% of all variance peaks in the reentrant circuit for episode 3 were associated with the stable functional lines of block compared to the 93.1% for episode 2A (Table 2). For episode 7, a mean of 83.7% of all variance peaks were associated with the stable functional lines of block. The relationships between variance peaks and functional lines of block for amplitude (94.5%) and phase lag (86.9%) are shown in FIGS. 11A and B for this tachycardia. The site of spontaneous termination appears in FIG. 11B as a variance peak of medium height residing within the central common pathway near the exit. Much of the region of the central common pathway and the periphery away from functional lines of block exhibit minimal variance.

The correspondence of variance peaks with functional lines of block for all parameters in all episodes of tachycardia ranged from 96.7% in episode 4A to 64.7% in episode 9 with an average of 86.5% (Table 2). The amplitude (93.2%), the normalized mean variance (89.0%), the duration (88.1%) and the phase lag (84.4%) parameters provided the best correlation of variance peaks with functional lines of block. The average baseline (83.7%) and the MSE (80.8%) did not provide as good a correlation between variance peaks with functional lines of block. The MSE correlation would have been much improved for the group if not for episodes 2B and 9 which showed only a 31.7 and 41.4% correlation. For the remaining tachycardias alone the mean MSE correlation was 88.2%.

The random association of variance peaks with functional lines of block was computed as the number of sites adjacent to all functional lines of block, divided by the total number of sites in the grid. The mean association by random chance was 19.2% for all tachycardias which is significantly lower than the data shown in Table 2.

C. DISCUSSION

1) Electrogram Characteristics for Analysis of Conduction Properties

The characteristics of extracellular electrograms can provide important information about properties of conduction which are not available from transmembrane potential recordings. For example, slow conduction (5–7), anisotropic conduction (2–4), and collision of wavefronts (1) all have specific representation in extracellular space. Therefore, extracellular electrogram morphology (shape, duration, amplitude) can provide useful information for analyzing conduction properties of reentrant circuits. In this regard electrograms with rapid upstrokes in regions of slow activation have suggested slow anisotropic conduction (2), double potentials have been interpreted to indicate conduction block (9,10,23), and fractionated electrograms have inferred slow, nonuniform and discontinuous conduction (4–8,11,13,24,25). All such analyses and interpretations have been based on individual electrogram complexes; beat-to-beat changes (dynamic changes) in morphology have not been reported. In this study we tested the hypothesis that additional information about conduction in reentrant circuits might be obtained from analysis of such dynamic changes.

2) Adaptive Template Matching for Quantifying Biological Signals

An accurate method was needed to quantify dynamic, beat-to-beat changes in electrogram morphology. The method that we used, adaptive template matching (ATM), is an offshoot of adaptive signal processing. The adaptive template matching technique as developed by Widrow (16) is a modification of the least mean squares (LMS) algorithm (21), the main difference being that for ATM only short signal segments are adaptively matched for best overlap, whereas continuous signals are adaptively matched for best overlap in LMS. ATM has previously been applied to the analysis of other bioelectric signals (16,26,27).

We used ATM to quantify scale (amplitude and duration) and shift (phase and average baseline) parameters of electrogram shape, because they measure aspects of the extracellular potential that reflect changes in the intracellular action potential during impulse conduction (1–4,7). The average baseline parameter was included for completeness of the two dimensional algorithmic scale and shift operations because it provides independent information that is necessary to compute the ATM weights. Any changes in average baseline which may have occurred because of changes in cell electrophysiology e.g., changes in resting potential (28), were most likely eliminated to a large extent by the high pass filter at the signal inputs. Therefore, the source of the small average baseline changes which occurred was most likely an artifact of the two-dimensional template matching process. The sum of squares (MSE estimate) criterion was used for adaptation of the weights because, following weight convergence to the optimal weighting, MSE is also a measure of the difference in the intrinsic shape of the two signals (16, 21). Thus, the MSE was used as a fifth ATM parameter and measured cycle-to-cycle changes in intrinsic electrogram shape. With ATM, because each electrogram on each cardiac cycle could be compared to a reference or template electrogram, we obtained information about the changes that occurred in electrogram morphology from one cardiac cycle to the next. Since this information was available in a unified form (i.e., the parameters of scale, shift, and MSE), site-to-site comparisons of dynamic electrogram morphology could be obtained even though the shape of the electrogram itself varied widely from site to site.

The algorithm which we developed used the differential steepest descent (DSD) method to compute the weight update (29) because it is simple to compute. The magnitude and direction for weight adjustment was determined by calculating a derivative of the error based on finite difference changes in the weighting. However, the DSD method results in a misadjustment of the weights (29). To minimize the misadjustment the convergence coefficient should be minimized (but this will also slow convergence of the weights and therefore increase the time for computation), the number of data samples should be maximized (i.e., the length of the segments for matching should be maximized), and the finite difference should be maximized (but this will decrease the sensitivity of the weight update to very small changes in shape). Thus, the most practical way to minimize the misadjustment is to maximize the length of the segment for matching. We chose 100 milliseconds which corresponds to approximately 100 data points. A greater segment length might sometimes cause overlap of consecutive cardiac cycles, since the cycle length of reentrant ventricular tachycardias in the canine model can be as short as approximately 140 milliseconds (our unpublished observations). Use of the sum of squares difference over the signal segments to compute the weighting also increases the achievable resolution of the time alignment (phase weight) (26). When the wavelets are initially aligned so that their peak data points coincide (as we did in our study), convergence to a resolution of less than 0.05 data points (0.05 milliseconds in our study) is possible for sharper electrograms when signal to noise ratios are on the order of 100:1. In comparison, methods that align waveforms based on peaks by definition result in convergence to a resolution of 1 data point. High-resolution activation mapping (not part of this study) may also benefit from the high phase resolution obtainable with ATM. Similar resolutions are also potentially achievable for the other ATM weights (amplitude, duration, and average baseline), since they are computed in the same way as the phase weight.

3) Electrophysiology of High Variance in ATM Parameters at Functional Lines of Block in Reentrant Circuits We found that regions of greatest variance of ATM parameters were adjacent (within one electrode on either side) to the location of functional lines of block that formed the boundaries of the central common pathway in reentrant circuits. The high variance was not related to any special characteristics of the electrograms during tachycardia since double potentials, fractionated electrograms and biphasic potentials all occurred adjacent to the lines of block. Since variance was measured over many cardiac cycles without regard to order, a high variance does not necessarily imply net changes in ATM parameters in any particular direction (directional information was not part of this method of quantification). The high variances indicate that there were greater cycle to cycle changes in amplitude, duration, phase and shape of electrograms in the regions straddling the functional block in the reentrant circuits than in other areas of the border zone. Changes in the extent and location of the functional lines of block as is sometimes associated with unsustained tachycardia (lasting less than 30 sec) (see FIGS. 6A,C) is predicted to markedly change electrogram characteristics. However, the high variance was not dependent on such alterations in the location of the lines of block since it occurred even when changes were minimal during unsustained tachycardia (FIG. 6B) or during sustained tachycardia (FIGS. 6D–E and 11) or when the 50 cycles of ATM analysis did not include terminal cycles. Furthermore, when ATM measurements included the last few cycles of unsustained tachycardia when most changes in lines of block or slowing of conduction in the central common pathway occurred, they only affected variance slightly because ATM measurements are weighted equally for all cycles. Other instabilities at functional lines of block, therefore, are responsible for subtle beat to beat changes in electrogram morphology which are not dependent on conduction changes around the circuit nor on gross changes in the extent or location of the block. Segments of lines of block in anisotropic circuits may actually be areas of pseudoblock where there is slow and nonuniform conduction without actual block (8). Beat-to-beat changes in the conduction pathway on a microscale would be expected to cause high electrogram variances. If collisions of wavefronts originating on either side of the block line occur as in the leading circle model (30), sites of collision might shift slightly from beat to beat. If the line of block is a linear unexcited region as in the spiral wave model (31), beat to beat changes in penetration of the reentrant wavefront into this region from either side caused by small changes in wavefront curvature, may lead to instabilities of the electrograms. An understanding of the electrophysiological mechanisms for the high variance awaits a more complete description of the mechanisms causing the lines of block in this reentrant model which might be obtained by high resolution activation mapping within the 6–10 mm that encompasses the lines of block. While the functional lines of block showed large variances, the electrograms in most of the central common pathway did not. This feature likely reflects uniform and stable conduction over the same pathway on a microscale. However, sites of spontaneous termination of unsustained and sustained tachycardias sometimes tended to have a higher variance than other portions of the central common pathway although less than at the lines of block. The variance in electrograms recorded in the outer pathways of the reentrant circuits and in regions of the epicardial border zone at a distance from the circuit was low, also implying relative stability of conduction properties.

4) Possible Clinical Applications of ATM Signal Processing

Special characteristics of electrograms have been sought that locate reentrant circuits for surgical incision or catheter ablation in patients with ventricular tachycardia since detailed activation mapping cannot always define the reentrant pathway. During sinus rhythm mapping intraoperatively or with catheters, patients with sustained ventricular tachycardia have been found to have more sites with fractionated and abnormal (low amplitude, long duration) electrograms than patients with unsustained tachycardia or no tachycardia (12). The location of these recording sites however, is a poor predictor of reentrant circuit location as assessed by the results of surgical (12) or catheter ablation (15). During ventricular tachycardia mapping, continuous electrical activity extending throughout the diastolic interval (11) or double potentials (23) may indicate the location of reentrant circuits but these electrogram characteristics cannot always be found (13–15). The timing of occurrence of local electrical activity relative to the surface QRS during tachycardia has also been used as a guideline for location of reentrant circuits with variable success, for example, the location of potentials in mid-diastole, separated from the main body of ventricular potentials associated with the QRS complex by an isoelectric segment (24). More recently, electrogram characteristics have been used to locate a region of slow activation while stimulation at that site is used to validate that it is part of the reentrant circuit based on the analysis of stimulated QRS morphology, stimulus to QRS intervals, and post pacing cycle length (13–15,25). However, electrogram features of morphology and timing from analysis of single complexes, that are specific for reentrant circuit localization in patients have not been described.

Our results show that functional lines of block in reentrant circuits causing unsustained and sustained monomorphic ventricular tachycardia in a canine model can be located by analyzing ATM variances or other weight variabilities. Such analysis can be done automatically and rapidly by computer processing with the algorithms described. Although in this study calculations of variances and variance maps for one episode of tachycardia required about 20 minutes using a Pentium based PC computer with a 200 MHZ processor, computation time should easily be reduced to less than 5 minutes by increasing processing speed and utilizing multiple processors to work in parallel to quantify ATM variances or other weight variabilities at a number of sites simultaneously. In this study it was also necessary to construct detailed activation maps from large numbers of recording sites to validate the method since it was necessary to correlate the regions of high ATM weight variability with isochronal activation maps. However, having done that, functional lines of block can now be located without the necessity for drawing the isochronal maps. We propose that this method may, therefore, have applications for locating functional reentrant circuits and the functional lines of block that bound the central common pathway, for catheter ablation of ventricular tachycardia without the necessity for recording from such a large number of sites and without constructing activation maps. There is evidence from activation mapping that functional circuits cause some ventricular tachycardias in patients with ischemic heart disease (14,32–35). Ablation of the central common pathway between lines of functional block may prevent tachycardia as shown by El-Sherif et al (36) in this canine model.

5) Limitations and Future Directions

The results of this study have a number of limitations which require additional investigation to ascertain the clinical usefulness of the methodology. In order for the ATM method to be useful for localizing functional circuits clinically, specificity needs to be maintained when the number of recording sites is reduced to a number compatible with available clinical multisite mapping electrodes such as the basket electrodes under current development (37). The cellular mechanisms for functional block in human reentrant circuits may not be the same as in the animal model and it is likely that block in human circuits is sometimes anatomical (14,32–35). It is uncertain whether different kinds of block will show the same high variance as we have shown here. It is also uncertain whether the methodology would be useful to locate short lasting, unstable reentrant circuits which may cause polymorphic ventricular tachycardia since significant beat to beat changes in lines of block and activation patterns may lead to nonspecific changes in electrogram morphology at sites that are not associated with the reentrant circuits. Finally, some functional lines of block associated with reentrant circuits may bound dead end pathways or bystander regions which are not crucial to the reentrant mechanism, yet show high variances. It might therefore, be necessary to utilize entrainment methodology or some activation mapping along with the ATM signal processing to try and identify such regions. Although some of these questions might be answered from additional studies in animal models, others can only be answered from clinical investigations.

REFERENCES

1. Spach M S, Barr R C, Johnson E A, et al. Cardiac extracellular potentials. Analysis of complex waveforms about the Purkinje networks in dogs. Circ Res 1973; 33:465–473.
2. Spach M S, Miller W T III, Miller-Jones E., Warren R B, and Barr R C. Extracellular potentials related to intracellular action potentials during impulse conduction in anisotropic canine cardiac muscle. Circ Res 1979; 45:188–204.
3. Spach M S, Miller W T III, Geselowitz D B, et al. The discontinuous nature of propagation in normal canine cardiac muscle. Evidence for recurrent discontinuities of intracellular resistance that affect the membrane currents. Circ Res 1981; 48:39–54.
4. Spach M S, Dolber P C. Relating extracellular potentials and their derivatives to anisotropic propagation at a microscopic level in human cardiac muscle. Evidence for electrical uncoupling of side to side fiber connections with increasing age. Circ Res 1986; 58:356–371.
5. Waldo, A L, Kaiser G A. A study of ventricular arrhythmias associated with acute myocardial infarction in the canine heart. Circulation 1973; 1222–1228.
6. Boineau J P, Cox J L. Slow ventricular activation in acute myocardial infarction. A source of re-entrant premature ventricular contractions. Circulation 1973; 48:702–713.
7. Gardner P I, Ursell P C, Fenoglio J J Jr, et al. Electrophysiologic and anatomic basis for fractionated electrograms recorded from healed myocardial infarcts. Circulation 1985; 72:596–611.
8. Dillon S M, Allessie M A, Ursell P C, et al. Influences of anisotropic tissue structure on reentrant circuits in epicardial border zone of subacute canine infarcts. Circ Res 1988; 63:182–206.
9. Feld G K, Shahandel-Rad F. Mechanism of double potentials recorded during sustained atrial flutter in the canine right atrial crush-injury model. Circulation 1992; 86:628–641.
10. Restivo M, Gough W B, El-Sherif N. Ventricular arrhythmias in the subacute myocardial infarction period. High-resolution activation and refractory patterns of reentrant rhythms. Circ Res 1990; 66:1310–1327.
11. Josephson M E, Horowitz L N, Farshidi A. Continuous local electrical activity. A mechanism of recurrent ventricular tachycardia. Circulation 1978; 57:659–665.
12. Kienzle M G, Miller J, Falcone R A, et al. Intraoperative endocardial mapping during sinus rhythm: relationship to site of origin of ventricular tachycardia. Circulation 1984; 70:957–965.
13. Stevenson W G, Khan H, Sager P, et al. Identification of reentry circuit sites during catheter mapping and radiofrequency ablation of ventricular tachycardia late after myocardial infarction. Circulation 1993; 88:1647–1670.
14. Stevenson W. Catheter mapping of ventricular tachycardia. In: Zipes D P and Jalife J eds. Cardiac Electrophysiology. From Cell to Bedside. W. B. Saunders Co. Philadelphia Pa. 1995. pp 1093–1099.
15. Stevenson W G. Ventricular tachycardia after myocardial infarction: From Arrhythmia surgery to catheter ablation. J Cardiovasc Electrophys 1995; 6:942–950.
16. Widrow B. The rubber mask technique. Pattern measurement and analysis. Pattern Recognition 1973, 5: 175–197.
17. El-Sherif N. The FIG. 8 model of reentrant excitation in the canine postinfarction heart. In: Zipes D P and Jalife J eds. Cardiac Electrophysiology. From Cell to Bedside. W.B. Saunders Co. Philadelphia Pa. 1995. pp 363–378.
18. Ciaccio E J. Novel quantification of impulse slowing followed by spontaneous termination in the central isthmus of anisotropic reentrant circuits. In: J. Liebman ed. Electrocardiology from the cell to the body surface '96. World Scientific 1995. pp 605–606.
19. Coromilas J, Saltman A E, Waldecker B, et al. Electrophysiologic effects of flecainide on anisotropic conduction and reentry in infarcted canine hearts. Circulation 1995; 91:2245–2263.
20. Ciaccio E J, Wit A L, Scheinman M M, et al. Prediction of the location and time of spontaneous termination of reentrant ventricular tachycardia for radiofrequency catheter ablation. J Electrocardiol 1995; 28(Suppl):165–173.
21. Widrow B, Glover Jr. J R, McCool J M, et al. Adaptive noise canceling: principles and applications. Proc IEEE 1975; 63:1692–1716.
22. Scheaffer, R. L., Mendenhall, W., Ott, L. Elementary Survey Sampling, 2nd Ed. Duxbury Press, North Sciatuate, Mass., p.6 and p.178.
23. Olshansky B, Moreira D, Waldo A L. Characterization of double potentials in ventricular tachycardia. Circulation 1993; 87:373–381.
24. Fitzgerald D M, Friday K J, Yeung Lai Wah J A, et al. Electrogram patterns predicting successful catheter ablation of ventricular tachycardia. Circulation 1988; 77:806–814.
25. Morady F, Frank R, Kou W H, Tonet J L, et al. Identification and catheter ablation of a zone of slow conduction in the reentrant circuit of ventricular tachycardia in humans. J Am Coll Cardiol 1988; 11:775–782.
26. McGill K C, Dorfman L J. High-resolution alignment of sampled waveforms. IEEE Trans Biomed Eng 1984; BME-31:462–468.
27. Lo Conte L R and Merletti R. Advances in processing of surface myoelectric signals: Part 2. Med Biol Eng Comp 1995; 33:373–384.
28. Kleber A G, Janse M J, van Capelle F J, et al. Mechanism and time source of S-T and T-Q segment changes during acute regional myocardial ischemia in the pig heart determined by extracellular and intracellular recordings. Circulation Research 1978; 42:603–613.
29. Widrow B, McCool J M. A comparison of adaptive algorithms based on the methods of steepest descent and random search. IEEE Trans Ant Prop 1976; AP-24:615–637.
30. Allessie M A, Bonke F I, Schopman F J. Circus movement in rabbit atrial muscle as a mechanism of tachycardia. III. The "leading circle" concept: a new model of circus movement in cardiac tissue without the involvement of an anatomical obstacle. Circ Res 1977; 41:9–19.
31. Pertsov A M, Davidenko J M, Salomonsz R, et al. Spiral waves of excitation underlie reentrant activity in isolated cardiac muscle. Circ Res 1993; 72:631–650.
32. Miller J M, Harken A H, Hargrove W C, et al. Pattern of endocardial activation during sustained ventricular tachycardia. J Am Coll Cardiol 1985; 6:1280–1287.
33. De Baaker J M T, van Capelle F J L, Janse M J, et al. Reentry as a cause of ventricular tachycardia in patients with chronic ischemic heart disease: electrophysiologic and anatomical correlation. Circulation 1988; 77:589–606.
34. Downar E, Harris L L, Mickleborough L L, et al. Endocardial mapping ventricular tachycardia in the intact human ventricle: evidence for reentrant mechanisms. J Am Coll Cardiol 1988; 783–791.
35. Littman L, Svenson R H, Gallaher J J, et al. Functional role of theepicardiumn postinfarction ventricular tachycardia. Observations derived from computerized epicardial activation mapping, entrainment, and epicardial laser photoablation. Circulation 1991; 83:1577–1591.
36. El-Sherif N, Mehra R, Gough W B, et al. Reentrant ventricular arrhythmias in the late myocardial infarction period. Interruptions of reentrant circuits by cryothermal techniques. Circulation 1983; 68:644–656.
37. Triedman J K, Jenkins K J, Colan S D, et al. Intra-atrial reentrant tachycardia after palliation of congenital heart disease: characterization of multiple macroreentrant circuits using fluoroscopically based three-dimensional endocardial mapping. J of Cardiovasc Electrophys 1997; 8:259–270.

EXPERIMENT #2

Ventricular tachycardia (VT) is an important health concern that can be debilitating and even life threatening. There is abundant evidence that many and perhaps a majority of VTs occurring in humans are caused by reentry[1-11]. The initiation of a reentrant circuit requires a zone of slow conduction and a zone of unidirectional block. In large reentry circuits such as those arising from infarct scars, areas of slow conduction in and around the scar should be targeted for ablation[6]. Clinical studies suggest that targeting this region will interrupt the circuit and stop tachycardia without recurrence. In a series of patients in which transcatheter shocks were delivered to a zone of slow conduction (SCZ) bounded by unexcitable tissue between the pacing site and the exit site of the reentrant circuit, VT was terminated without recurrence[2]. In another series of patients in which the common SCZ for reentry circuits with two distinct circuit morphologies was ablated, there was also no recurrence of reentrant VT associated with cardiomyopathy[11]. In a third series of patients in which two tachycardia morphologies occurred with a shared SCZ within the mitral isthmus, a single application of RF energy at the site of slow conduction common to both VT morphologies eliminated tachycardia without recurrence[9]. In a canine study el-Sherif found that cryothermy applied to sites within the central common pathway (CCP) of reentrant circuits during VT, wherein the SCZ resides, was the only region that would terminate reentry[12].

The SCZ has special properties that may be related to its efficacy as an ablation site. Tachycardia-dependent conduction delay can occur in the SCZ and may be partly mediated by changes in calcium channel-dependent and sodium channel-dependent conduction[10]. The action of drugs on the SCZ may vary, and can even be proarrhythmic[3]. Pacing at a critical cycle length results in conduction delay[5] or orthodromic block[4] in the SCZ. During pacing in the SCZ, conduction slows and the S-QRS and postpacing intervals increase[7] suggesting that this zone is easily fatigued. In a canine model of reentrant VT with figure of eight pattern, when spontaneous termination occurred the reentrant wave was found to always block in the CCP[13,14]. This latter phenomenon is related to cycle-by-cycle progressively delayed conduction occurring within the SCZ at an area where CCP width is narrowed[15]. Channel geometry, which can evolve over the course of a VT[15], may play an important role in progressively delayed conduction[16]. Hence, in both humans and in a canine model the SCZ during reentrant VT is a dynamic, not a static, region that may be thought of as a focal point or "weak link" in the circuit that is easily fatigued. As we will demonstrate, progressively delayed conduction in and around the SCZ, as well as progressively more rapid conduction there, can be detected elsewhere in the circuit as far-field activity. We have developed a procedure, termed piecewise linear adaptive template matching (PLATM), which measures changes in the shape of electrogram deflections over short time intervals for detection of changes in far-field activity. We will show how this method can be used to time-localize activation at the proximal and distal boundary lines of the SCZ during reentrant VT.

METHODS

1) Data Collection and Activation Mapping

A laboratory model of VT caused by reentrant excitation was used to test the analytical methods. This model has many characteristics that are very similar to those of clinical tachycardia associated with chronic ischemia, including inducibility and termination by programmed stimulation techniques[17], the ability to be entrained[18] and similar responses to antiarrhythmic drugs[19]. Unsustained and sustained monomorphic VT, polymorphic VT, and VT with multiple morphologies can be induced in this animal model as they can in patients with ischemic heart disease. The surgical procedure to create the infarct involves complete occlusion of the LAD and has been described elsewhere[17]. Bipolar electrograms are recorded from 196–312 electrodes simultaneously[15]. Following data acquisition, activation times of electrogram signals are marked automatically, using criteria based on electrogram slope and peak features, followed by manual correction[17]. An activation map is generated by printing the activation times on a computerized map grid using a planar projection of the electrode sites located on the curved surface of the heart. Isochrones separating regions of similar activation times are plotted with 10–20 msec spacing and by arbitrary definition, lines of block separate adjacent electrode sites with activation time differences of greater than 40 msec and where wavefronts on opposite sides of the lines are moving in different directions.

VT cycle length (CL) was determined from onset to termination by measuring the ECG peak-to-peak interval. In FIG. 12 are shown the relationships between CL and cycle number for four episodes of VT. The episodes of VT in Panels A and B (episodes 1A and 1B) are from the same canine experiment whereas those in Panels C and D (episodes 2 and 3) are from different experiments. During each VT there is at least one quiescent period, bounded by dashed lines, in which CL change is approximately linear with respect to cycle number. In episode 1A, there are three adjacent quiescent periods where CL changes in alternate directions; CL still increases overall. Quiescent periods are flanked by periods of unstable CL at onset, and just prior to spontaneous termination (episodes 1B and 2); episodes 1A and 3 were terminated by premature stimulation. These events are in accord with previous observations of CL[15].

Activation maps of the endpoint cycles of the quiescent periods in FIG. 12 were used to measure changes in conduction velocity (CV) in the reentrant circuit. An example is shown in FIG. 12 for episode 1A. FIGS. 13A–D are the activation maps for the four respective endpoint cycles shown by dashed lines in FIG. 12A. The CCP is located near the center of each map. Sites of interest are circled in FIGS. 13A–B and their site numbers are given in FIG. 13B. In episodes of VT during this experiment when spontaneous termination occurred (14 of 20) site 55 near the SCZ center was the site of block. The major change in the conduction pattern between maps occurs at the SCZ, where the number of isochrones is directly related to CL. In FIGS. 13B and D (CL 236 and 241 msec respectively) there are more isochrones in the SCZ whereas in FIG. 13A and C (CL 217 and 224 msec respectively) there are less isochrones. Distal to the narrowed CCP there is a zone of rapid conduction (RCZ) in which the activating wavefront has the form of a jet. In FIGS. 13B and 13D CV in the RCZ is increased whereas it is decreased in the activation maps of FIGS. 13A and 13C; this is reverse to changes in CV occurring in the SCZ. Small changes in spurs of lines of functional block also occur near the SCZ from one map to the next. Several bystander areas are present (at an area of three sites near the CCP exit encircled by a line of block, and at two small areas on either side of the CCP created by spurs).

2) Electrogram Deflection Preprocessing

Electrograms in and near the CCP were graphed to show more precisely the relationship between CL and changes in CV. Electrogram traces from sites 61–51 (episode 1A) are plotted in FIG. 14 with site numbers denoted parenthetically between traces. The activation times during each cardiac cycle are denoted by short, thin vertical lines. The numbers directly to the right of the marks on the first cycle are activation time differences between two adjacent sites. The total time for activation from site 61 to site 52 (i.e., the approximate time for activation through the CCP) is given at the bottom of each panel. The difference in the total time for activation from one panel to another equals the difference in CL between the two panels. The thick vertical lines denote the edges of the SCZ (S) and RCZ (R) intervals. The SCZ activation interval is longer and the RCZ interval shorter in FIGS. 14B and D where CL is longer as compared to FIGS. 14A and C. The parenthetical numbers between cycles are the difference in activation time between successive cardiac cycles at the local site. When there is a change in activation between any two sites, CL changes at distal sites. For example, the large jump from 241 to 236 msec from site 57 to site 56 in FIG. 14D causes one of the oscillatory swings in CL that can be observed in FIG. 12A.

Figures 15A, 15B:
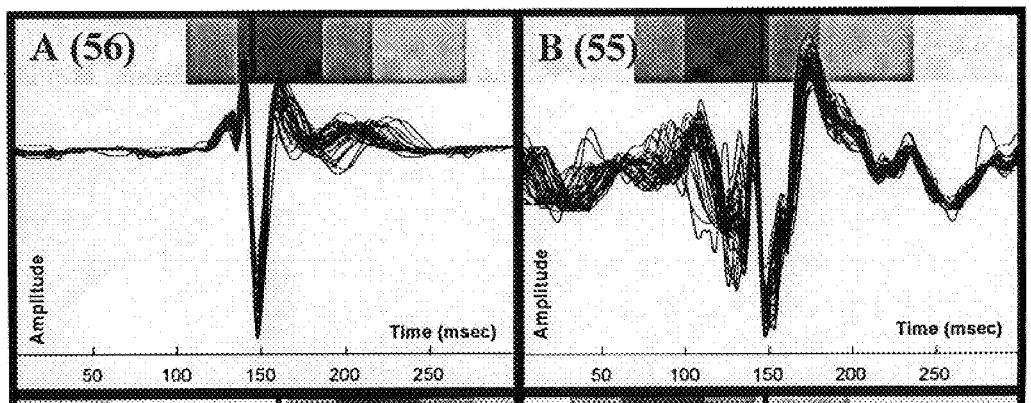
FIGS. 15A–15D Electrograms from sites 56, 55, 74, and 64 extracted from successive cardiac cycles during the quiescent interval of episode 1B are shown time-aligned with respect to the largest peak. Red, yellow, green, and blue traces denote electrograms from successively later cardiac cycles. The colored bar above the electrogram traces denotes the activation time intervals of the SCZ (red/orange), the RCZ (green), the NCZ (yellow), and electrogram activation time (black). Panel A shows site 56. Panel B shows site 55. Panel C shows site 74. Panel D shows site 64.
Figures 15C, 15D:
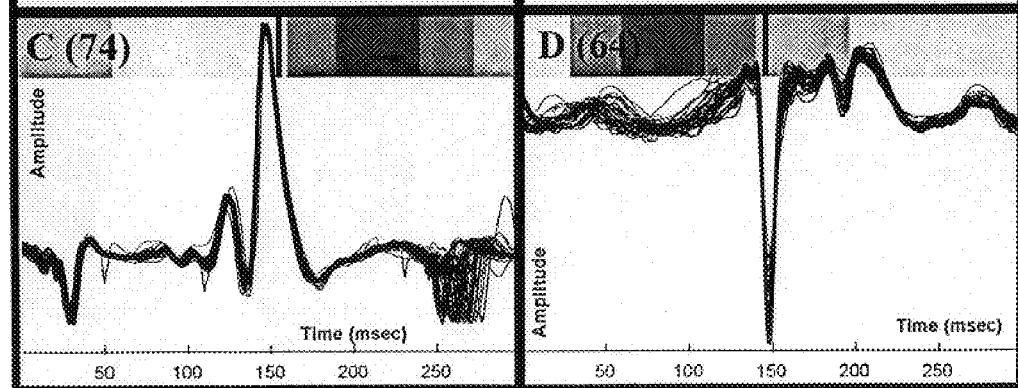
Figure 16A:
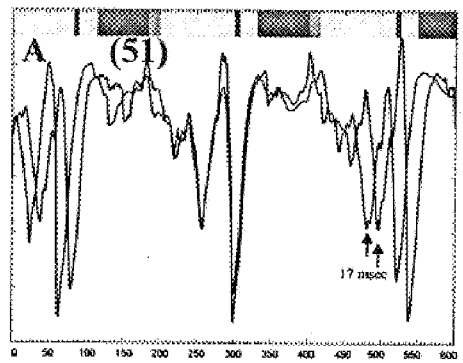
FIGS. 16A–16D Electrograms from sites 51 (Panel A), 55 (Panel B), 74 (Panel C), and 64 (Panel D) from the beginning (red) and ending (blue) cycles during the first quiescent period of episode 1A are time-aligned with respect to the largest peak. The colored bar is as described in FIG. 15.
Figure 16B:
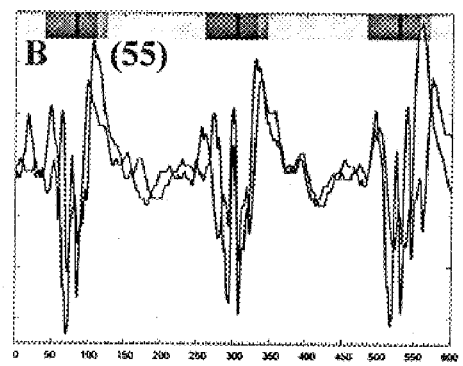
Figure 16C:
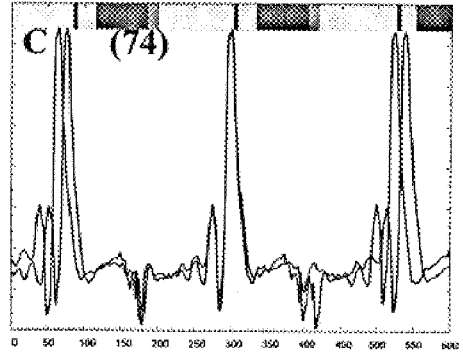
Figure 16D:
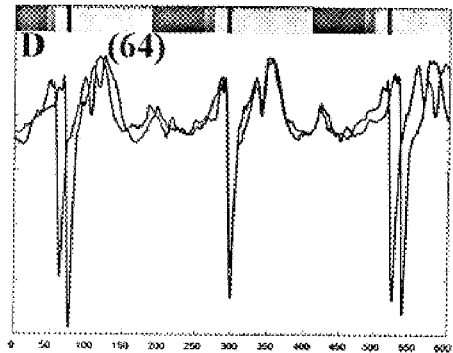
Figure 17A:
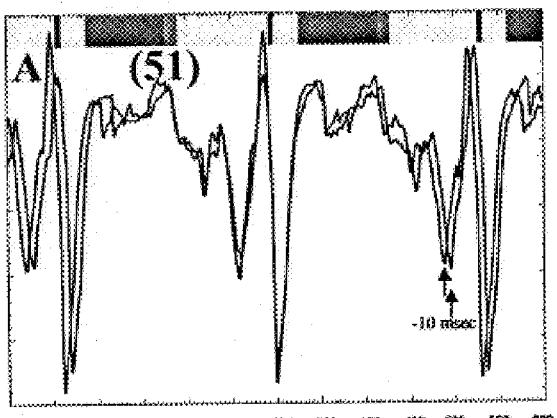
FIGS. 17A–17D Electrograms from sites 51 (Panel A), 55 (Panel B), 74 (Panel C), and 64 (Panel D) from the beginning (red) and ending (blue) cycle during the second quiescent interval for episode 1A are time-aligned with respect to the largest peak. The colored bar is as described in FIG. 15.
Figure 17B:
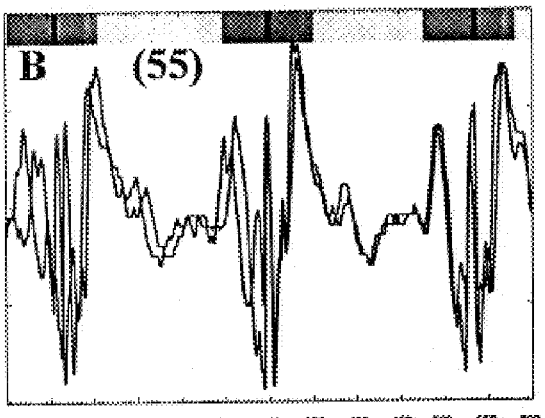
Figure 17C:
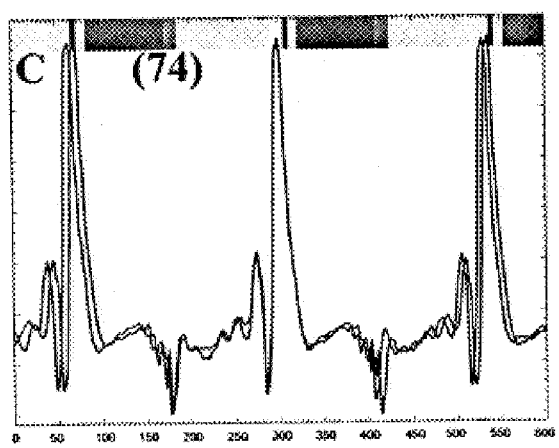
Figure 17D:
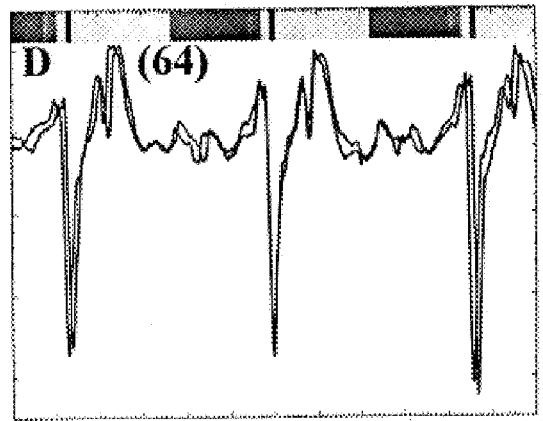
Figure 18A:
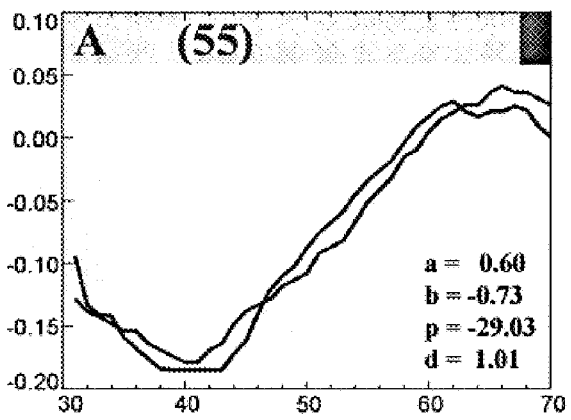
FIGS. 18A–18D PLATM template matches are shown for site 55, VT episode 1B. The panels show the beginning (red trace) and ending (blue trace) electrogram segments from the quiescent period. The end electrogram segment (input) is shown optimally weighted by PLATM for maximum overlap with the beginning electrogram (template). Optimal weighting values are shown. Panel A shows match from normal conduction zone. Panel B shows match form slow conduction zone. Panel C shows match from rapid conduction zone. Panel D shows match from normal conduction zone.
Figure 18B:
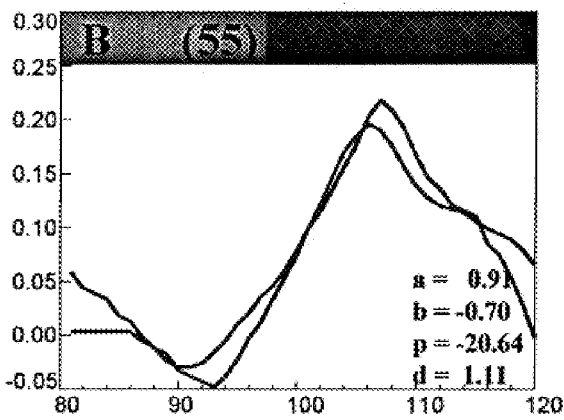
Figure 18C:
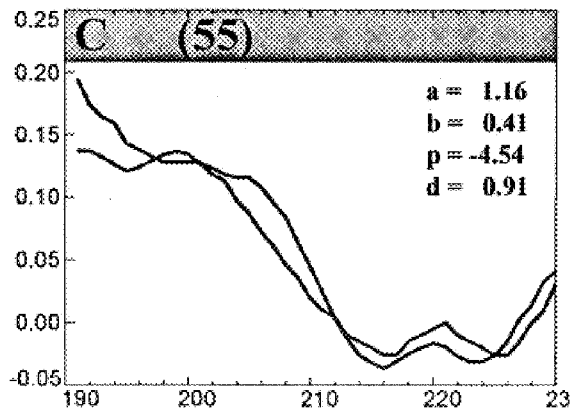
Figure 18D:
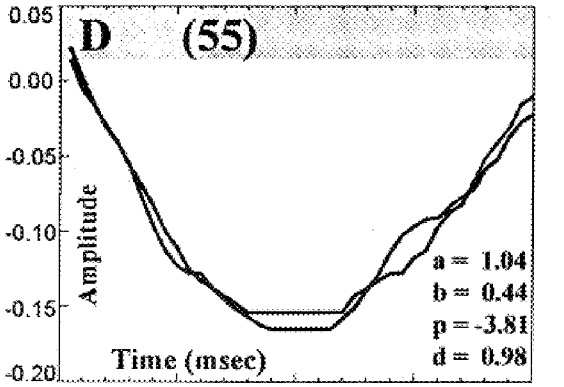
Figure 19A:
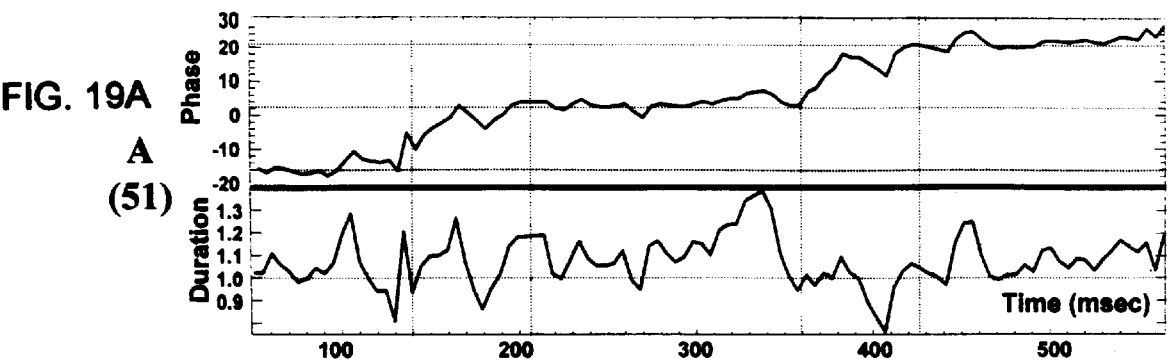
FIGS. 19A–19D Examples of PLATM phase and duration weighting of the beginning and ending electrogram segments for the first quiescent interval of episode 1A (sites 51, 55, 74, 64). The dotted lines show time of activation of the proximal and distal border of the SCZ with respect to local activation, determined from the activation map of FIG. 13A. Site 51 (panel A), site 55 (panel B), Site 74 (Panel C), Site 64 (panel D).
Figure 19B:
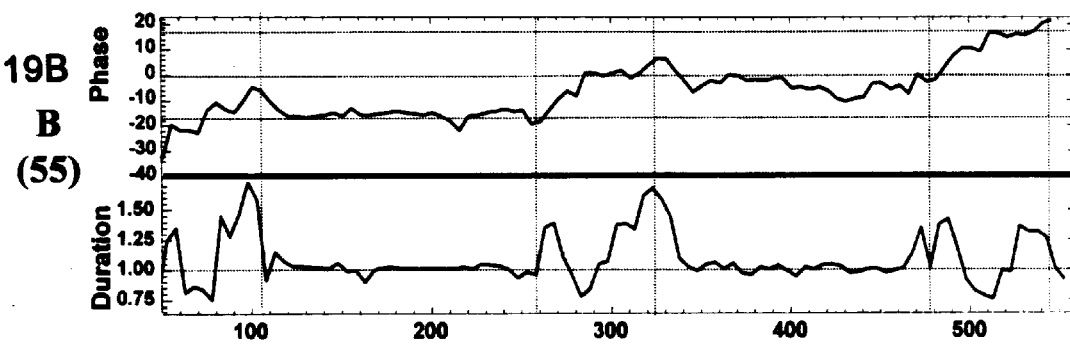
Figure 19C:
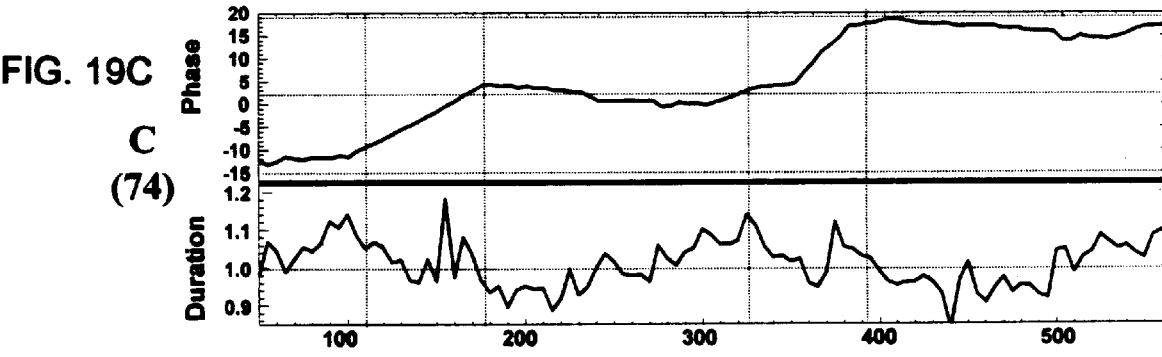
Figure 19D:
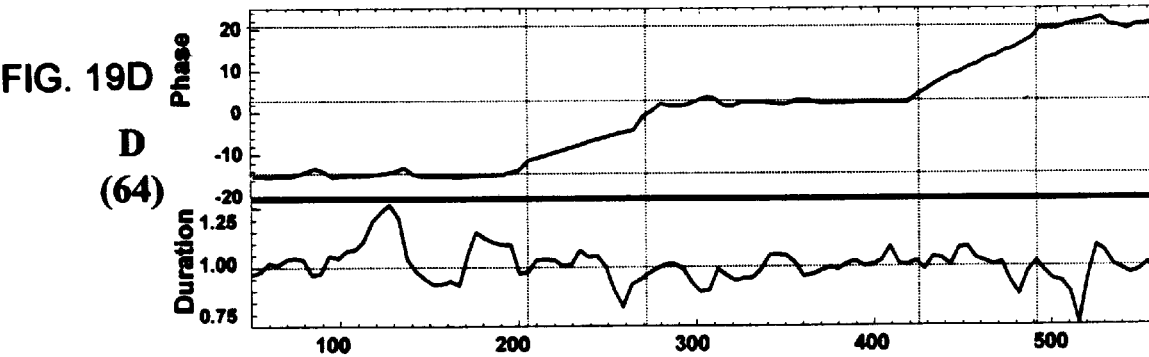
Figure 20A:
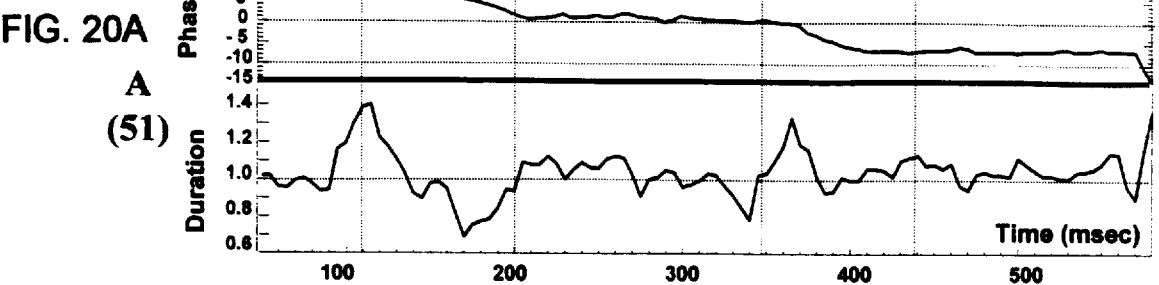
FIGS. 20A–20D Examples of PLATM phase and duration weighting of the beginning and ending electrogram segments for the second quiescent interval of episode 1A (sites 51, 55, 74, 64). The dotted lines show time of activation of the proximal and distal border of the SCZ with respect to local activation, determined from the activation map of FIG. 13B. Site 51 (panel A), site 55 (panel B), Site 74 (Panel C), Site 64 (panel D).
Figure 20B:
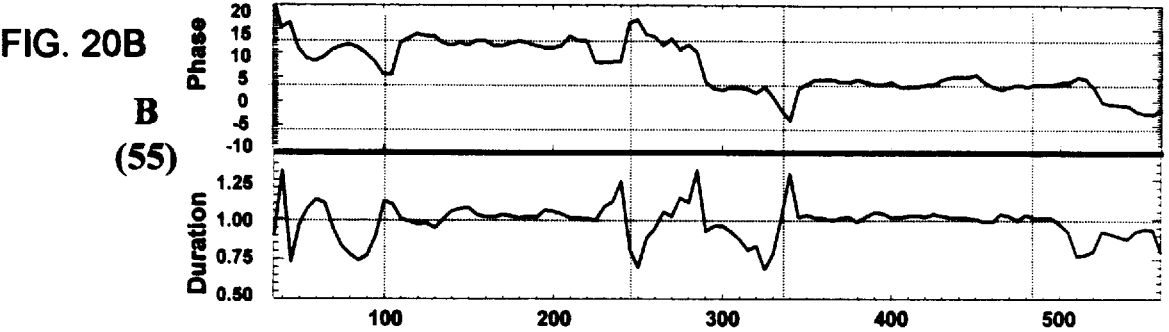
Figure 20C:
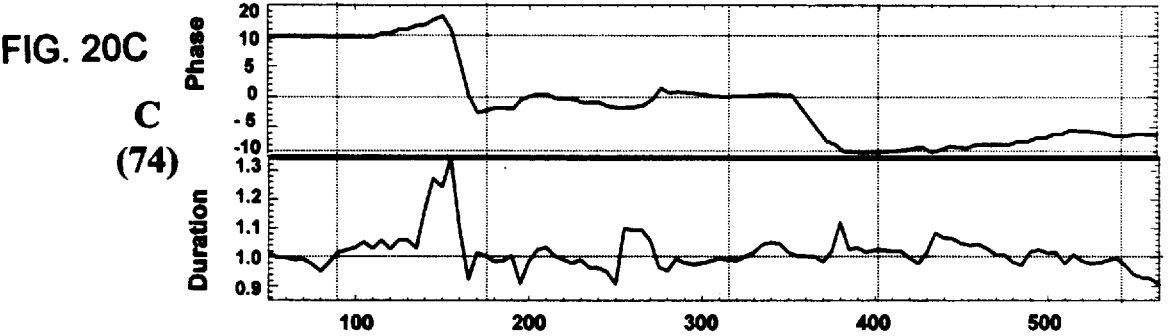
Figure 20D:
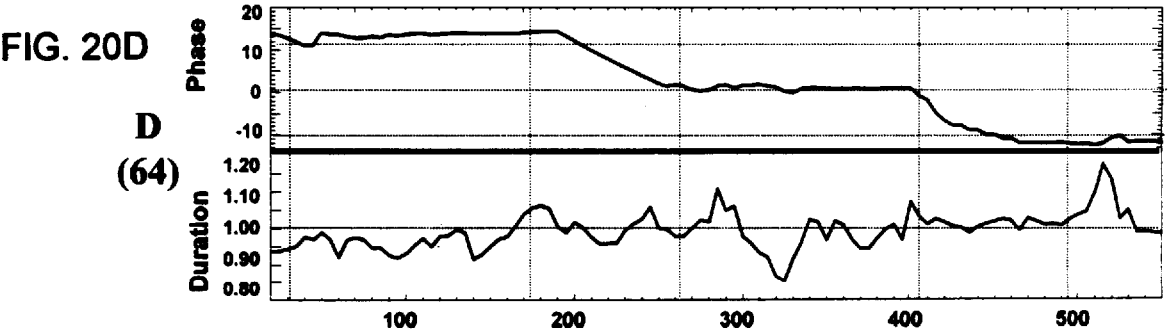

To determine if changes in CV were correlated with advances or delays in the electrogram deflections, the electrograms for an entire quiescent period at selected sites were first extracted from the data, time-aligned with respect to the largest peak, and graphed. FIG. 15 shows time-aligned electrograms from VT episode 1B (sites 56, 55, 74, and 64). The shape of the CCP and of the electrograms for episodes 1A and 1B were virtually identical and FIGS. 13A–B can be used as a guide to site location. Episode 1B electrograms are given in FIG. 15 because disparities in electrogram deflection are more apparent due to larger changes in CV. The electrograms of the first cardiac cycles in the sequence are colored red and those of the subsequent few cardiac cycles are colored yellow, green, and blue respectively. The colored bar at the top of each panel denotes activation intervals of the SCZ (red where CV decreases the most, and orange), RCZ (green), and the remaining portion of the circuit where there is little change in CV that can be considered a normal conduction zone or NCZ (yellow). The black line shows local activation time. In each panel of FIG. 15, the waveform gradually expands and the phase lags over successive cycles during the SCZ activation interval, in conformity with the gradual trend of CL prolongation depicted in FIG. 12B for episode 1B. The waveform contracts and the phase advances slightly during the interval when the RCZ activates. Note for example at site 55 that the deflections become delayed at 150–175 msec (during the interval when the SCZ is activating) but then advance when the RCZ is activating (180–230 msec). This causes electrogram deflections from the last cycles (blue) to shift to the left of electrogram deflections of the earliest cycles (red) beginning at about time 205 msec. If an SCZ\RCZ activation interval coincides with an isoelectric electrogram segment, phase changes will not be visible until the end of the segment since the measurement is cumulative (see for example, Panel C, time 165–300 msec), and duration changes, which are not cumulative measurements, will be unobservable.

3) PLATM Measurements

To quantify electrogram deflection changes, it was first necessary to provide starting phase shift weights, at 5 msec intervals, between two signals. In FIGS. 16A–D are graphed electrograms from sites 51, 55, 74, and 64 at the beginning (red) and end (blue) of the first quiescent interval of episode 1A. Similarly to FIG. 15, the colored bar at the top of each panel denotes activation of the SCZ (orange), RCZ (green), and NCZ (yellow) with respect to local activation (black). The red and blue traces are time-aligned with respect to the maximum peak. The end electrogram (blue trace) expands and delays with respect to the beginning electrogram (red trace) during the interval that the SCZ activates, contracts and advances during the interval that the RCZ activates, and exhibits no change during the intervals that the NCZ activates. Ruler and caliper measurements made at approximately 20 fiducial points along each pair of signals where corresponding peaks were observable (e.g. see arrows, FIG. 16A) were used to initialize phase shift. Linear interpolation between these fiducial points provided the initial phase weight at 5 msec intervals. In FIGS. 17A–D, traces from the same selected sites as in FIG. 16 from the beginning (red) and end (blue) of the second quiescent period of episode 1A (decreasing CL) are shown. The electrogram deflection dynamics are the same as in FIG. 16 except that they are reversed (e.g. see arrows, FIG. 17A). The deflections contract and advance during the SCZ activation interval and expand and delay during the RCZ activation interval.

Changes in electrogram deflections were quantified using PLATM which is a template matching method for determining similarity of signal shapes and is based on the equations for adaptive template matching (ATM)[15,20]. The templates are sliding 40 msec segments of an electrogram extracted from the beginning cardiac cycle of a CL quiescent period and the inputs for matching are sliding 40 msec segments of electrograms extracted from the ending cardiac cycle of the quiescent period. The inputs are adaptively weighted based on the mean squared error (MSE) criterion for best overlap with the template[21]. The parameters for weighting are the amplitude and duration (scale the signal vertically and horizontally) and the average baseline and phase shift (shift the signal vertically and horizontally). Amplitude and duration weights were initialized to a 1:1 correspondence, the average baseline was initialized to zero difference, and phase shift was initialized as described above. Upon convergence to the optimal weighting there is maximal signal overlap. The PLATM phase weight shows the degree of shift in msec needed to overlap the electrogram segments. The 40 msec window was shifted by 5 msec increments to measure duration and phase changes over approximately 2 cardiac cycles. The starting and ending points of the largest shift in PLATM phase weight in one direction, closest to the local activation time, were used to estimate the time of activation of the SCZ proximal and distal borders, respectively. These points were determined by measuring the times at which the change in phase leveled off to approximately zero with ruler and caliper. The results were tabulated for each of the quiescent intervals at each of the four selected PLATM measurement sites.

RESULTS

In FIG. 18 selected PLATM matches are shown for the electrogram of site 55, episode 1B. The colored bars denote times of SCZ, RCZ, and NCZ activation intervals as in FIGS. 16–17. The short 40 msec matching segments were extracted from longer 300 msec electrogram segments which were time-aligned at 150 msec centered about the maximum peaks (FIG. 15B). The amplitude (a), average level (b), phase shift (p), and duration (d) PLATM weights at convergence to best overlap are given. The duration weight is greater than unity during the SCZ activation interval (FIG. 18B) indicating that the end electrogram expanded with respect to the beginning electrogram.

The duration was less than unity during the RCZ activation interval (FIG. 18C) indicating that the end electrogram contracted with respect to the beginning electrogram. The duration was approximately unity during the NCZ activation interval (FIGS. 18A and D) indicating that the end electrogram did not expand or contract with respect to the beginning electrogram. During the SCZ activation interval the phase weight lagged and during the RCZ interval it advanced due to increased CV. The total PLATM phase shift during the interval of SCZ/RCZ activation approximated the change in CL from beginning to end of the quiescent period.

In FIGS. 19A–D an example of PLATM duration and phase weighting is shown for the entire first quiescent period of VT episode 1A (sites 51, 55, 74, and 64 respectively). The PLATM phase weights were initialized based on FIGS. 16A–D. The phase lags during the time interval when the SCZ activates (vertical dotted lines) at each of the four sites. The difference in phase over one cardiac cycle is equal to the change in CL during the first quiescent interval (17 msec). The center plateau of constant phase is sometimes shifted from zero due to a difference between peak-to-peak phase alignment (the zero line) and the optimal phase alignment determined by PLATM. The duration is sometimes, but not always, greater than unity when the SCZ activates. In FIGS. 20A–D the PLATM duration and phase weighting is shown for the second quiescent interval of episode 1A using the same respective four sites. The PLATM phase weights were initialized based on FIGS. 17A–D. The phase disparity is reversed to that which occurs in FIG. 19; it advances during the time interval when the SCZ activates at each of the four sites. The difference in phase over one cardiac cycle is equal to the change in CL during the second quiescent interval (−10 msec). The duration is sometimes, but not always, less than unity when the SCZ activates. Table 1 shows the absolute difference in activation times at the SCZ determined by PLATM versus activation mapping from the four different areas of the circuit was measured for the six quiescent periods of FIG. 12.

TABLE 3A

Relationship of SCZ Proximal Edge Activation Time Determined by PLATM versus Activation Mapping

| SITE | | EPISODE | | | | | | |
|---|---|---|---|---|---|---|---|---|
| | | 1A (i) | 1A (ii) | 1A (iii) | 1B | 2 | 3 | AMean |
| $D_{out}$ | (msec) | 0 | 1 | −7 | 0 | −5 | 5 | 3.0 |
| $D_{SCZ}$ | (msec) | −2 | 3 | 8 | 2 | 1 | −21 | 6.2 |
| $D_{Ent}$ | (msec) | −10 | 13 | −13 | −1 | 0 | −2 | 6.5 |
| $D_{Exit}$ | (msec) | −12 | 22 | −3 | 0 | 3 | 0 | 6.3 |
| AMean | (msec) | 6.0 | 9.9 | 7.8 | 0.8 | 2.3 | 7.0 | 5.6 |

TABLE 3B

Relationship of SCZ Distal Edge Activation Time
Determined by PLATM versus Activation Mapping

| SITE | | 1A (i) | 1A (ii) | 1A (iii) | 1B | 2 | 3 | Amean |
|---|---|---|---|---|---|---|---|---|
| $D_{Out}$ | (msec) | 6 | −29 | 8 | −20 | −5 | −7 | 12.3 |
| $D_{SCZ}$ | (msec) | 1 | 3 | 4 | −1 | −3 | 10 | 3.7 |
| $D_{Ent}$ | (msec) | 7 | −7 | 0 | −18 | 3 | −2 | 5.0 |
| $D_{Exit}$ | (msec) | 5 | −19 | 5 | −2 | 0 | −1 | 5.7 |
| AMean | (msec) | 3.3 | 14.5 | 4.3 | 10.3 | 2.8 | 5.0 | 6.7 |

Legend for tables 3A and 3B above
i, ii, iii - the first, second, and third quiescent periods, respectively.
D - difference in activation time at the SCZ border determined by PLATM versus activation mapping.
$_{Out}$ - Site residing away from the CCP.
$_{SCZ}$ - Site residing in SCZ of CCP.
$_{Ent}$ - Site residing near CCP entrance.
$_{Exit}$ - Site residing near CCP exit.
AMean - absolute mean.

In Table 3A and 3B the difference in activation time at the SCZ proximal and distal borders, respectively, are shown. The mean absolute differences for determining the activation time of the proximal and distal edges of the SCZ are 5.6 and 6.7 msec, respectively. Site location with respect to the SCZ does not appear to influence the accuracy of the PLATM measurement. However, PLATM measurement of the SCZ activation interval is poorer when CL decreases (1Aii). The average CL for the six quiescent periods was 225.8 msec. The range of ±6.2 msec average absolute disparity in activation time of the SCZ edges results in an accuracy of (225.8−12.4)/225.8=94.6%.

DISCUSSION

1) Relationship to Catheter Ablation Site

The goal of this study was to develop a foundation for accurate time-localization of the SCZ activation interval based on single-site recordings with possible application to distance-localization of ablation sites. Current treatment of reentrant VT by ablation to interrupt the circuit is sometimes problematic. Ablation will fail if lesions that are too small or too far away from the reentrant pathway incompletely ablate arrhythmogenic sites or if all arrhythmogenic sites are not identified[22,23]. An effective method to determine arrhythmogenic sites for ablation is to find areas which when paced during VT exhibit entrainment with concealed fusion[7,8]. However, the geometry of the reentrant tract can be complex and extensive with multiple entrances and exits[24]. Thus entrainment with concealed fusion can occur from bystander areas as well[8], so that not all areas that when stimulated, entrain the tachycardia with concealed fusion are good ablation sites. Activation mapping is also used to identify arrhythmogenic sites for ablation but besides being tedious and time consuming, it is subjective when multiple electrogram deflections are present[25]. PLATM might be adaptable to localize sites for catheter ablation, having advantages over existing methods, if the difference in activation time between the local site and the SCZ can be translated into a distance along an arc of the circuit (see Model below). If this is possible then the location of a roving ablation catheter could be updated toward the SCZ based on the computed distance from the local site. When CL changes, and corresponding electrogram deflection changes occur gradually and approximately linearly (FIGS. 1 and 4), probe location could potentially be updated based on only a few cycles' worth of data. Although CV changes during reentry in the same canine model have been reported to occur in other areas of the circuit such as at wavefront pivot points[13,14], our observations suggest that the SCZ/RCZ is a focal point for CV changes during reentry, and that the assumption that changing deflections are caused by SCZ/RCZ CV changes is valid.

2) Signal Processing

PLATM was developed to time-localize SCZ/RCZ activation based on measurements of far-field activity. Far-field electrogram deflections result from changes in the direction of the electric field as the activating wavefront pivots around obstacles to conduction[26]. Bipolar electrodes, used in our recordings and often used clinically to record from the tip of an ablation catheter, sense far-field activity differently from unipolar electrodes (decreased amplitudes and slopes in bipolar recordings)[27-30]. These factors are not expected to influence quantification of far-field electrogram deflections, however, since PLATM measurements are relative, not absolute, and therefore independent of slope and peak absolute magnitudes. Our early approach for electrogram shape quantification, adaptive template matching (ATM)[15,20] measured electrogram shape changes over a fixed 100 msec window centered on the largest electrogram deflection during each cardiac cycle. There is good overlap of template and input using ATM only if the "intrinsic shapes"[21], i.e., shapes following normalization for shift and scale, are similar. ATM cannot accurately measure changes in far-field activity which occur over short time-localized intervals (see FIGS. 15–17). Hence PLATM, which uses 40 msec sliding windows (N=40 sample points) was developed. This was a compromise between too large a window (less time-localized PLATM measurements) and too small a window (less accurate because there are fewer observations N to form a good estimate of the MSE weight update criterion)[3]. Although RCZ activation interval edges were not addressed in this study, detection may be possible; for example, as a dip in the phase trace in FIG. 19B, time 330–350 msec.

3) Model

As a first approximation of the changes in CV in the SCZ/RCZ that occur during reentry, causing CL prolongation, and their effect on signal shape, a linear model was developed that is shown in FIG. 21. Panel A shows a hypothetical reentrant circuit, denoted by the dotted line, with three distinct arcs: the SCZ (orange-yellow to red bars), RCZ (yellow-green to violet bars), and NCZ (yellow area). Each bar covers a 5 mm arc of the circuit. In this example the CL prolongs by 39 msec (from 208 msec to 247 msec) over the course of the VT during 50 cardiac cycles. CV from cycle k to cycle k+50 decreases in the SCZ and increases in the RCZ according to the specifications given in Table 4. The fraction CV(k)/CV(k+50) in Table 4 is the change in time base (i.e., change in duration) that occurs from cycle k to cycle k+50; it increases in the SCZ and decreases in the RCZ. The phase column shows the phase shift that results from a given change in duration across a 5 mm arc of the circuit. The duration and phase lag properties of FIG. 21A and Table 4 during the interval 0–500 msec are shown in FIG. 21B. The duration changes from 0.50 (violet) to 2.60 (red). The colored bars in FIG. 21B denote the times of activation in the SCZ and the RCZ during cycle k with respect to local activation at the site. In FIG. 21C the effect of the changes in duration and phase shift given in FIGS. 21A and 21B and Table 4 is shown for an example electrogram whose location is shown by the gray circle in FIG. 21A. The changes in electrogram shape are very similar to those that occur for the site 55 electrogram of FIG. 16B and it was this electrogram that was actually modeled. The model parameters did not include amplitude and average baseline and so these factors were not accounted for.

TABLE 4

Model Changes in Conduction Velocity in the CCP.

| Color | CV (k) | CV (k + 50) | Duration | Phase |
|---|---|---|---|---|
| Violet | 1.6 | 3.20 | 0.50 | 1.57 |
| Dark blue | 1.5 | 2.54 | 0.59 | 1.36 |
| Blue | 1.4 | 2.09 | 0.67 | 1.18 |
| Light blue | 1.3 | 1.73 | 0.75 | 0.97 |
| Green | 1.2 | 1.46 | 0.83 | 0.71 |
| Yellow-green | 1.1 | 1.21 | 0.91 | 0.41 |
| Yellow | 1.0 | 1.00 | 1.00 | 0.00 |
| Yellow-orange | 0.9 | 0.64 | 1.40 | −2.25 |
| Orange | 0.8 | 0.44 | 1.80 | −5.11 |
| Orange-red | 0.7 | 0.32 | 2.20 | −8.49 |
| Red | 0.6 | 0.23 | 2.60 | −13.41 |

Legend for table 4 above
CV (k) - CV during cycle k.
CV (k + 50) - CV during cycle k + 50.

4) Limitations and Future Directions

Several additional problems need to be addressed if PLATM is to become an accurate method for time-localization of the SCZ activation. Electrogram deflections occurring during local activation were not always the largest magnitude deflections in the electrogram, making it impossible to establish the local activation time in those cases. Additional electrogram recordings obtained from neighboring sites might be useful to determine local activation time by consensus if the largest deflections at some of these sites are caused by local activation. Difference in intrinsic shape between the two signals was a possible source of measurement error. The poor correspondence of PLATM duration weight with SCZ/RCZ activation interval (except perhaps at site 55, FIGS. 19–20) was likely due to intrinsic shape differences. The PLATM duration weight may be more sensitive to intrinsic shape differences than phase, suggesting that refinement of the algorithm, such as in the selection of initial parameters, could be useful. We must also distinguish T-waves (ventricular repolarization), appearing on some electrograms as dome-shaped deflections of low amplitude, from deflections due to far-field activity, perhaps by using syntactic pattern recognition procedures[32]. Improved time resolution would allow for accurate time-localization of SCZ activation even when changes in CV are small (such as if only a few cardiac cycles of data were to be recorded from a site). Improved voltage resolution might allow detection of far-field activity in portions of the electrogram which appear isoelectric at lower voltage resolution. However, since there is an inverse relationship between field strength of the extracellular potential and distance to the site of origin[33], at distances greater than a few centimeters it will become difficult to separate the signal (electric field originating at the leading edge of the wavefront) from background noise. Future work will be directed toward addressing these limitations and to translate time-localization of SCZ activation into a distance from the electrogram recording site.

REFERENCES

1. Josephson M E, Horowitz L N, Farshidi A, Spielman S R, Michelson E L, Greenspan A M, Sustained ventricular tachycardia: evidence for protected localized reentry., Am J Cardiol 1978 September; 42(3):416–24.
2. Morady F, Frank R, Kou W H, Tonet J L, Nelson S D, Kounde S, De Buitleir M, Fontaine G. Identification and catheter ablation of a zone of slow conduction in the reentrant circuit of ventricular tachycardia in humans. J Am Coll Cardiol 1988 April; 11(4):775–82.
3. Chinushi M, Aizawa Y, Miyajima S, Funazaki T, Tamura M, Shibata A Proarrhythmic effects of antiarrhythmic drugs assessed by electrophysiologic study in recurrent sustained ventricular tachycardia. Jpn Circ J 1991 February; 55(2):133–41.
4. Aizawa Y, Niwano S, Chinushi M, Tamura M, Kusano Y, Miyajima T, Kitazawa H, Shibata A. Incidence and mechanism of interruption of reentrant ventricular tachycardia with rapid ventricular pacing. Circulation 1992 February; 85(2):589–95.
5. Habbab M A, el-Sherif N. Recordings from the slow zone of reentry during burst pacing versus programmed premature stimulation for initiation of reentrant ventricular tachycardia in patients with coronary artery disease. Am J Cardiol 1992 July 15; 70(2):211–7.
6. Stevenson W G, Sager P, Nademanee K, Hassan H, Middlekauff H R, Saxon L A, Wiener I, Identifying sites for catheter ablation of ventricular tachycardia. Herz 1992 June; 17(3):158–70.
7. Stevenson W G et al, "Identification of Reentrant Circuit Sites", Circ 88 (part 1):1647–1670, 1993.
8. Stevenson W G et al. Relation of pace mapping QRS configuration and conduction delay to ventricular tachycardia reentry circuits in human infarct scars. Journal of the American College of Cardiology 1985; 26:481–488.
9. Wilber D J, Kopp D E, Glascock D N, Kinder C A, Kall J G. Catheter ablation of the mitral isthmus for ventricular tachycardia associated with inferior infarction. Circulation 1995 December 15; 92(12):3481–9.
10. Okumura K, Yamabe H, Tsuchiya T, Tabuchi T, Iwasa A, Yasue H Characteristics of slow conduction zone demonstrated during entrainment of idiopathic ventricular tachycardia of left ventricular origin. Am J Cardiol 1996 February 15; 77(5):379–83.
11. Sato M, Sakurai M, Yotsukura A, Betsuyaku T, Ito T, Yoshida I, Kitabatake A The efficacy of radiofrequency catheter ablation for the treatment of ventricular tachycardia associated with cardiomyopathy. Jpn Circ J 1997 January; 61(1):55–63.
12. El-Sherif N et al. "Interruption of Reentrant Circuits by Cryothermal Techniques". Circ 68:644–656, 1983.
13. El-Sherif N, Yin H, Caref E B, Restivo M. Electrophysiologic Mechanisms of Spontaneous Termination of VT. Circulation 93(8):1567–1578, 1996.
14. Schmitt H, Wit A L, Coromilas J, Waldecker B. Mechanisms for Spontaneous Termination of Monomorphic Ventricular Tachycardia. JACC 31(2):460–472 1998.
15. Ciaccio E J, Scheinman M M, Fridman V, Schmitt Coromilas, Wit. "A new approach to the analysis of electrogram features for the localization of reentrant circuits". Submitted to Cardiovascular Electrophysiology, 1998.
16. Kogan et al. Excitation wave propagation within the narrow pathways: Geometric configurations facilitating unidirectional block and reentry. Physica D. 1992; 59:275–296.
17. Dillon S M et al. Influence of Anisotropic Tissue Structure on Reentrant Circuits. Circ Res 63:182–206, 1988.
18. Wit A L et al. Significance of the Endocardial and Epicardial Border Zone. In: Cardiac Arrhythmias: A Decade of Progress, edited by D C Harrison and G K Hall. Medical Publishers, Boston:1981, pp. 39–68.
19. Wit A L and M J Janse, *The Ventricular Arrhythmias of Ischemia and Infarction*. Futura, Mt. Kisco, N.Y., 1993.

20. Ciaccio E J, Wit A L, Scheinman M L, Coromilas J, Costeas C A, Kwaku K F, "Prediction of the Location and Time of Spontaneous Termination of Ventricular", J Electrocardiol 28 (Suppl.) pp 165–173, 1995.
21. Widrow B. Flexible Templates. Pattern Recognition 5, 1973.
22. Ideker R E, Smith W M, Blanchard S M, Reiser S L, Simpson E V, Wolf P D, Danieley N D. The assumptions of isochronal cardiac mapping. Pacing Clin Electrophysiol 1989 March; 12(3):456–78.
23. Blanchard S M, Walcott G P, Wharton J M, Ideker R E. Why is catheter ablation less successful than surgery for treating ventricular tachycardia that results from coronary artery disease? PACE 17(12 Pt 1):2315–35, 1994.
24. Downar E, Saito J et al. Endocardial Mapping of VT in the Intact Human Ventricle. JACC 25(7):1591–1600, 1995.
25. Bollacker K D et al. Automated Technique for Identification of Activation Fronts. Comps Biomed Res 1994 June; 27(3):229–44.
26. Ciaccio E J, Unpublished Observations, 1998.
27. Bagwell P, Pannizzo F, Furman S, Unipolar and bipolar right atrial appendage electrodes: comparison of sensing characteristics. Med Instrum 1985 May–June; 19(3): 132–5.
28. Damiano R J Jr, Blanchard S M, Asano T, Cox J L, Lowe J E Effects of distant potentials on unipolar electrograms in an animal model utilizing the right ventricular isolation procedure. J Am Coll Cardiol 1988 May; 11(5):1100–9.
29. Brouwer J, Nagelkerke D, den Heijer P, Ruiter J H, Mulder H, Begemann M J, Lie K I. Analysis of atrial sensed far-field ventricular signals: a reassessment. Pacing Clin Electrophysiol 1997 April; 20(4 Pt 1):916–22.
30. Nayak H M, Tsao L, Santoni-Rugiu F, Gomes J A, Mehta D, A pitfall in using far-field bipolar electrograms in arrhythmia discrimination in a patient with an implantable cardioverter defibrillator. Pacing Clin Electrophysiol 1997 November; 20(11):2864–6.
31. Widrow B and S D Stearns. *Adaptive Signal Processing*. Prentice-Hall, Englewood Cliffs N.J., 1985.
32. Papakonstantinou G, Gritzali F. Syntactic filtering of ECG waveforms. Computers and Biomedical Research 1981; 14:158–167.
33. Spach M S, Miller W T III, Miler-Jones E, Warren R B, Bar R C. Extracellular potentials related to intracellular action potentials during impulse conduction in anisotropic canine cardiac muscle. Circulation Research 1979; 45:188–204.

Experiment #3

Functional reentrant circuits causing monomorphic ventricular tachycardia induced by programmed electrical stimulation in the infarcted canine heart, form in the same locations and have the same size and shape on repeated initiations (1, 2, 3). Presumably this is also a property of reentrant circuits causing clinical ventricular tachycardia judging by similar QRS morphologies and cycle length of tachycardias during repeated induction (4). These characteristics suggest that reentrant circuits only form in regions with special electrophysiologic properties. In the canine model we have suggested that these properties include nonuniform anisotropic conduction (1) related to alterations in gap junctions that specifically occur where the functional lines of block form in the circuit (53).

Since a great deal of information about the electrophysiological properties of impulse conduction in cardiac muscle, such as slow and nonuniform propagation, can be found in the characteristics of the extracellular electrograms (6, 7, 8, 9), it might be predicted that such regions with special conduction properties necessary for reentry might be identified on the basis of extracellular current flow in the absence of the arrhythmia, for example during sinus rhythm or ventricular pacing. However, specific characteristics of electrograms (low amplitude, long duration, fractionation) have not been identified during sinus rhythm or pacing, which are accurate predictors of circuit location, in either experimental (10, 11, 12, 13, 15, 16), or clinical studies (17, 14, 18).

All prior studies to determine if specific electrophysiological properties where reentrant circuits occur can be detected in extracellular electrogram morphology during sinus rhythm have been based on analysis of single electrogram complexes. Whether dynamic changes in electrograms, changes from one cardiac cycle to the next, may reveal special features not evident in the analysis of single complexes has not been tested. Previously we have shown that such dynamic changes as quantified by an adaptive template matching method (ATM), can specifically locate the functional lines of block in reentrant circuits during ventricular tachycardia in the canine heart, where electrogram characteristics of single complexes are also not specific (21). We now have applied this method to the analysis of electrograms during sinus rhythm and ventricular pacing and show that regions where lines of functional block form after tachycardia induction by programmed stimulation, show specific dynamic changes which enable an accurate prediction of the location of the circuits and perhaps, where gap junction remodeling has occurred (53). This method might, therefore, be useful to locate some reentrant circuits in patients with ventricular tachycardia, during pacing or sinus rhythm mapping.

A. MATERIALS AND METHODS

1) Canine Model of Myocardial Infarction

Myocardial infarction was produced by ligating the left anterior descending coronary artery (LAD) near its origin in mongrel dogs (1). After four days, the dogs were anesthetized for the electrophysiologic study with pentobarbitol sodium (20–30 mg/kg). The chest was opened via a midsternal incision, and a multielectrode array sutured onto the anterolateral surface of the left ventricle. Catheters were placed in the femoral vein to administer fluids and in the femoral artery for measurement of blood pressure, and standard limb lead ECGs were recorded.

2) Signal Acquisition

Two different mapping electrode arrays, approximately 12×8 cm, were used in different experiments for recording electrograms from the epicardial border zone of the infarct (1). Both arrays were composed of 1 mm bipolar silver electrode discs embedded in a latex material. In one array there were 292 bipolar electrodes and recordings were made from 196 at a time. The bipolar electrode spacing was 2 mm and the distance between bipolar pairs was 5–10 mm (2). In the other array recordings were made from 312 electrodes simultaneously. The bipolar electrode spacing was 3.2 mm and the distance between bipolar pairs was 4.8–6.4 mm. Both arrays also contained stimulating electrodes at their basal and lateral margins and in the center. Bipolar stimulating electrodes were also sutured onto the right ventricle adjacent to the LAD.

The signals from the 292 recording electrode array were amplified, multiplexed, bandpass filtered (10 Hz–1 kHz) and digitized (8 bit resolution at 2 kHz). The digitized signals were recorded on an Ampex PR2230 wide band PCM tape recorder (Ampex Corporation, Redwood City, Calif., USA) along with ECGs, blood pressure, stimulus pulse, and voice annotation on FM channels. Data was acquired from the 312 bipolar array using a 320 channel mapping system with an analog bandpass filter of 15 Hz–500 Hz. The signals were digitized at 1 kHz and 16 bit voltage resolution. The digitized electrogram signals, along with digitized ECGs, blood pressure, stimulus pulse, and voice annotation signals were recorded onto a Pentium-class 133 mHz PC computer (Micron Technology Inc., Boise, Id., USA) hard drive using a DT3010 PCI data acquisition board (Data Translation Inc., Marlboro, Mass., USA) for data streaming.

3) Experimental Protocol

Electrograms were recorded from all sites in the epicardial border zone during sinus rhythm. The ventricles were stimulated from each of the pacing sites (LAD, base, lateral, center) at cycle lengths ranging from the longest enabling capture to cycle lengths approximating those of the tachycardia. Single or double premature stimuli (2 msec duration, 2–4 times diastolic threshold) were also delivered during basic drive of the ventricles from each of the four stimulation sites to initiate ventricular tachycardia (1). Activation maps of the epicardial border zone were constructed as previously described during sinus rhythm, stimulation and tachycardia (1, 21).

4) Analytical Methods

Dynamic changes in electrograms were analyzed by adaptive template matching (ATM) (20,19) during sinus rhythm, ventricular pacing from each of the four sites, and reentrant ventricular tachycardia in twelve infarcted canine hearts. ATM analysis of only ventricular tachycardia for these same twelve experiments has been presented (21). A summary of the characteristics of these tachycardias is given in Table 1 which has been published previously (21). Tachycardias lasted from 12.4 to 58.7 sec and terminated either spontaneously or after overdrive stimulation. Tachycardia cycle lengths ranged from 160 to 363 msec at the start and prolonged gradually prior to termination (Table 1). All tachycardias were associated with "figure of eight" patterns of reentry (22) mapped in the epicardial border zone. Lines of functional block around which the wavefronts rotated were parallel or diagonal to the long axis of the myocardial fibers (1) and were located in different regions of the anterior-left ventricle in different experiments (Table 1).

Figure 22A:
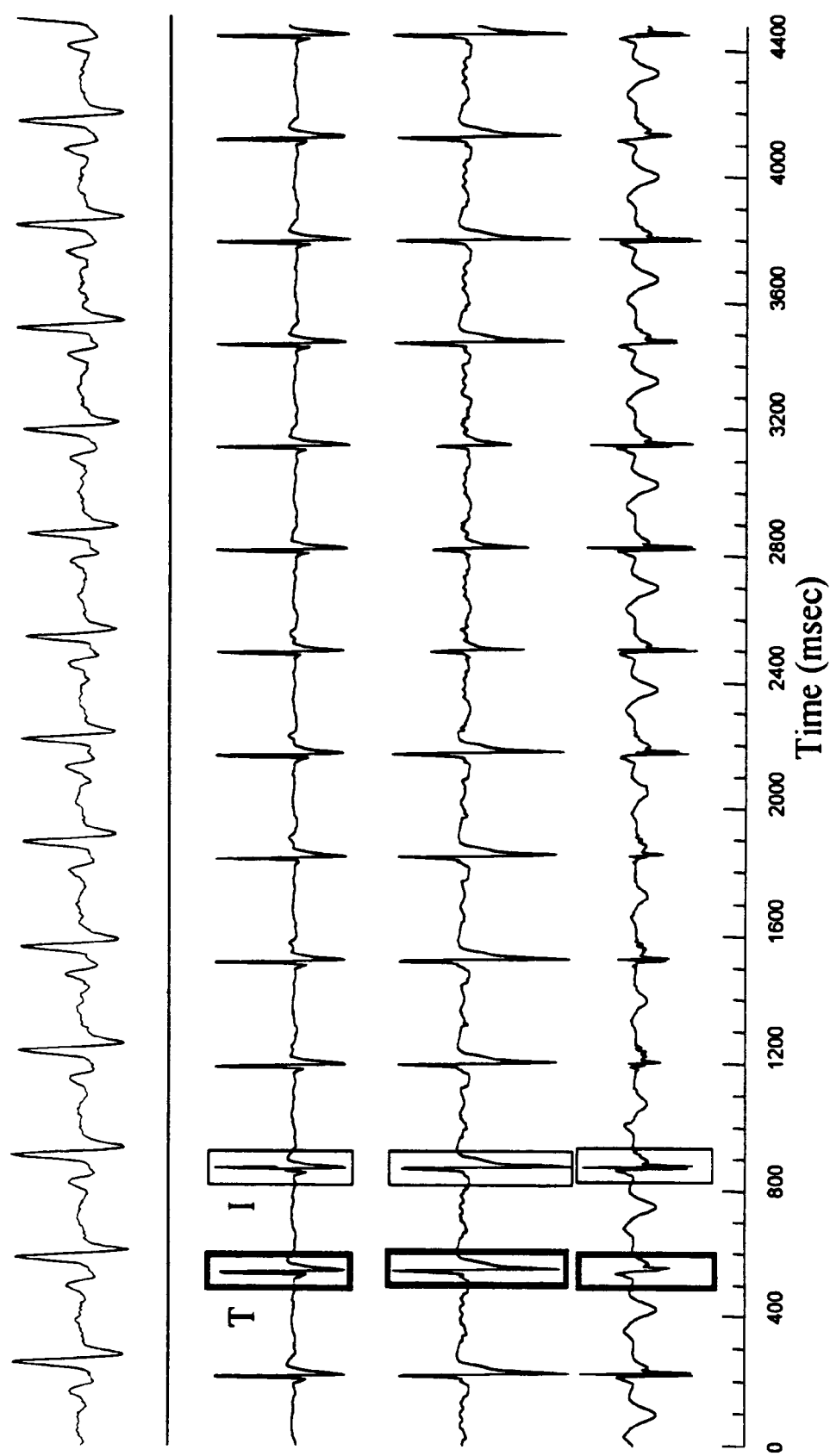
FIGS. 22A–22C The ATM template matching procedure is shown during sinus rhythm (A), ventricular pacing (B), and ventricular tachycardia (C). The top trace in each panel shows an ECG lead, the second trace shows the stimulus signal, and the bottom three traces show three selected electrograms. The selected electrograms are the same in each panel. The boxes marked T for each of the three electrogram sites denote the cycle that was used for the template. The boxes marked I for each of the three electrogram sites denote the cycle that was used for the first input. Subsequent cycles were used as subsequent inputs.
Figure 22B:
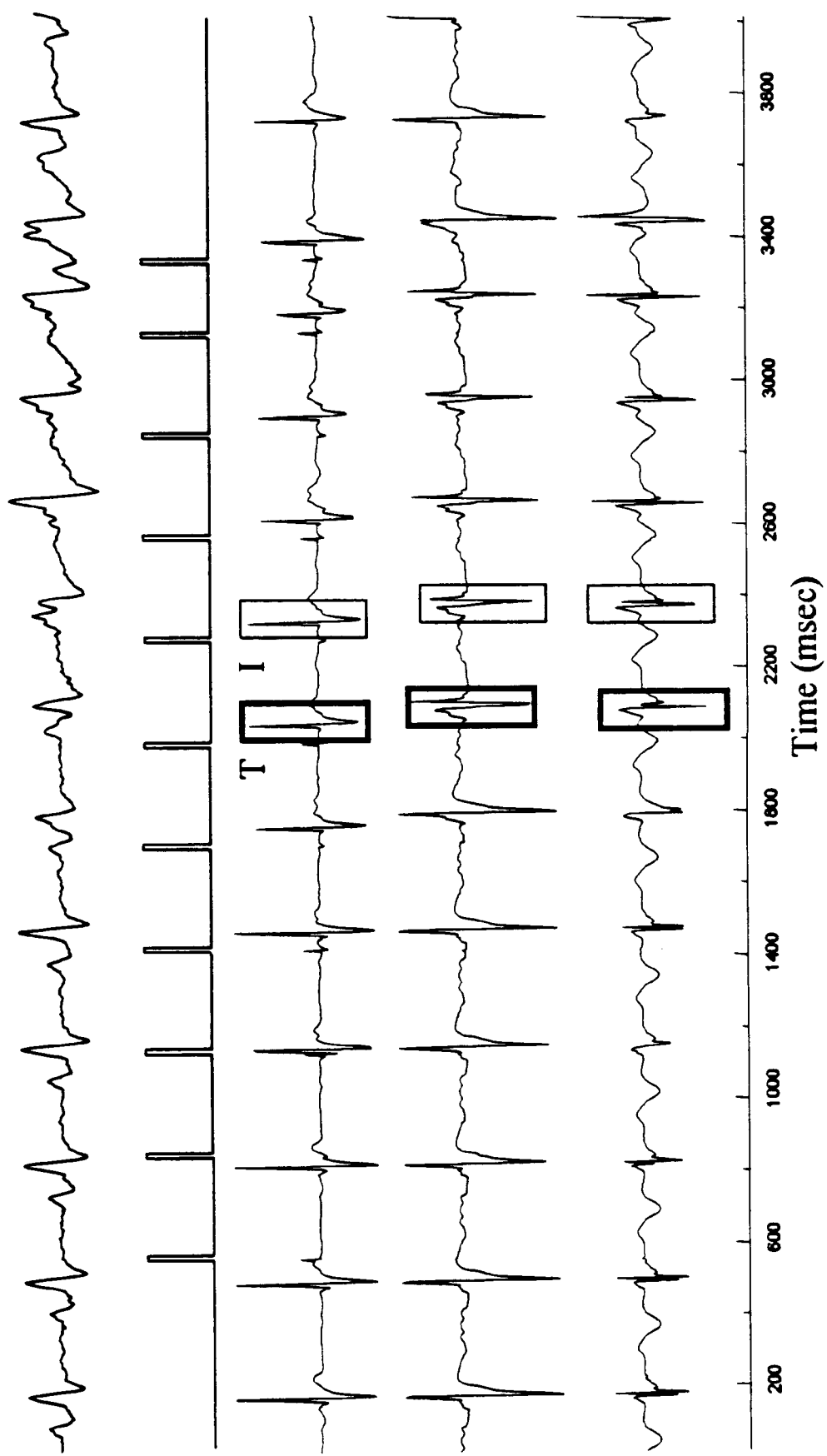
Figure 22C:
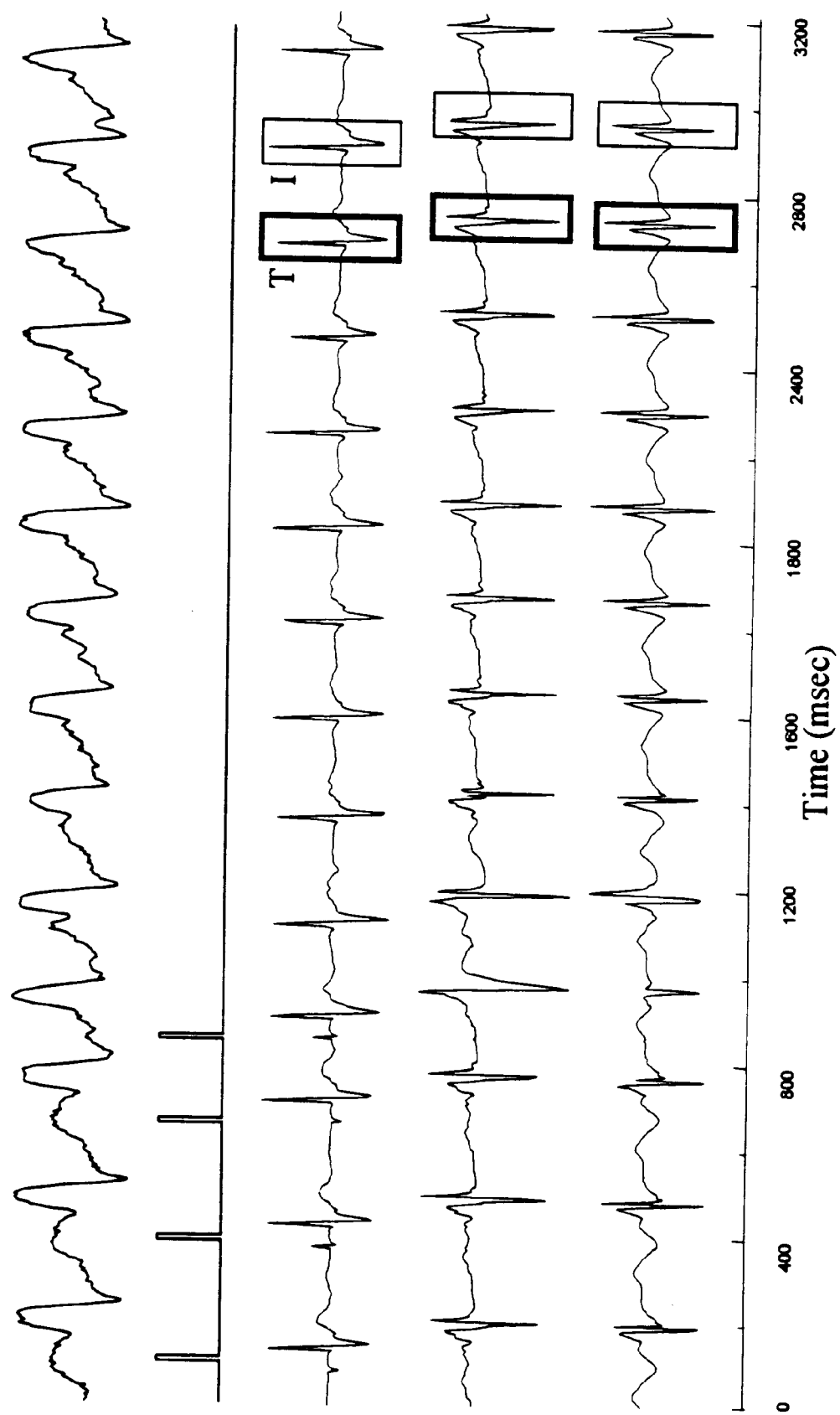

For ATM analysis of sinus rhythm (FIG. 22A), a template electrogram (T) was extracted from each of the 196 or 312 signals. The template consisted of a 100 msec window centered on a peak deflection during a cardiac cycle which was recorded at the beginning of each experiment, prior to pacing and prior to induction of reentrant tachycardia. Each of 50 subsequent cycles (I) was considered to be an input signal which was matched to the template (see below). For ATM analysis of ventricular pacing (FIG. 22B), the template electrogram (T) was selected from an early cycle during basic pacing at a constant rate and for ventricular tachycardia (FIG. 22C) an electrogram during the first 10 cycles was selected during a cardiac cycle in which the QRS morphology was the same (by eye) as the QRS during the remaining monomorphic tachycardia. Fifty subsequent cardiac cycles were used as input electrograms from all recording sites in the electrode array (first input electrogram is labeled I, FIGS. 22A–C) and were matched with each template.

The ATM matching procedure has been described in detail elsewhere (21), except that the algorithm was modified for this study to improve accuracy and versatility (to make ATM useful for analysis of signals obtained during sinus rhythm and pacing as well as during tachycardia). Briefly, each input electrogram for the 50 cycles that were analyzed at each recording site, was weighted for four parameters in two dimensions using parameters of scale (amplitude and duration) and shift (vertical shift and phase lag). These parameters have been defined previously (21) The mean square error (MSE) criterion, which is a measure of the difference in shape between the template and the input electrogram, was used to optimally adapt the weighting of the input for best overlap with the template (23). The convergence coefficients, which determine the step size for weight update, were optimized as follows. Three different convergence coefficients, which spanned the range of coefficient magnitudes, were used for ATM as rough initial indicators of the optimal coefficient magnitude. The mean MSE for all cardiac cycles was recorded using each of these coefficients, and the coefficient value that yielded the lowest average MSE for each channel was used as a starting point for optimizing the coefficient. Fine tuning was done by incrementally and adaptively adjusting the coefficient value until the minimum average MSE was obtained for each channel. This final convergence coefficient following adaptation was the optimal convergence coefficient to be used for ATM matching. The ATM matching procedure is illustrated in FIG. 2 where the template electrogram (thick trace) and input signal (thin trace) are shown for an experiment during sinus rhythm (SR), pacing from the base (BASE) and LAD electrodes, and during ventricular tachycardia. (VT). Initially the input is not well overlapped with the template (FIG. 23A). FIGS. 23B–D show respectively the weighting after 5, 25, and 500 iterations. After 500 iterations (FIG. 23D) the weights provide a very close overlap of the template and input signals. Iteration 500 was chosen as the stopping point to approximate the optimal solution for best overlap of the signals, based on the estimated MSE performance index (23). The weight values at the optimal weighting of each of the 50 input cycles were stored for subsequent analysis.

The variance statistic was used as the measure of dynamic changes in ATM parameters, and it was computed as previously described for the 50 cycles that were analyzed (21). The variance is defined as the sum of squares of the differences between the parameter weight of a given cardiac cycle, and the average parameter weight for all cycles matched (24). Variances were computed for the four ATM weighting parameters (amplitude and duration scale parameters, and phase lag and vertical shift parameters), and for the mean square error (MSE) between the template electrogram and the optimal weighted input electrogram. Additionally, the normalized mean variance was computed, which was the mean of all five variances after normalization of the ATM weight parameters. Each of the ATM parameters was summarized in the form of three dimensional statistical variance maps to show the cycle-to-cycle temporal variation in electrogram morphology at each recording site during sinus rhythm, ventricular pacing and ventricular tachycardia. On these maps, the X and Y axes marked the spatial position of the recording electrodes and the Z axis the magnitude of the variance (21). The location of the lines of functional block during tachycardia, although not present during sinus rhythm or ventricular pacing, were projected onto those maps as well as the maps of tachycardia so that they would be located at the same electrode sites. The correlation of electrode sites with high ATM variances or other weight variabilities (large cycle-to-cycle changes in weighting parameters) with the functional lines of block that occurred during tachycardia was computed for each of the rhythms. The variances were then ranked from highest to lowest, and the ten highest variance peaks were used for final processing. Of the ten highest variances, the number of peaks, weighted by peak height, that were overlapping or adjacent (within one grid cell on either side) to functional lines of block for each experiment was determined. The sum total of the magnitudes of the ten highest variance peaks adjacent to or overlapping lines of block was calculated. This sum was divided by the sum total of the magnitudes of all ten highest variance peaks and multiplied by 100 to calculate the percent association of variance peaks with functional lines of block (21).

We also determined how the center of mass (25) of the variance peaks of each ATM map during sinus rhythm and ventricular pacing, correlated with the location of the central common pathway of the reentrant circuit during ventricular tachycardia. The center of mass is defined as the average position in the XY coordinate system. It is determined by separately averaging the locations of the peak along the x axis and along the y axis. If the center of mass of the ATM weight variability peaks resides within the central common pathway, it might provide an accurate means to determine its location. First the mean center of mass of the 10 highest variance peaks was determined for all ATM weight variability maps generated from data obtained during a given episode of pacing or during sinus rhythm. A center of mass (CM) algorithm was used to make the computation, as follows:

$$CM(x) = [1/(6*10)] * \Sigma_i \Sigma_j V(x,i,j) \text{ for } i=1 \text{ to } 10, j=1 \text{ to } 6$$

$$CM(y) = [1/(6*10)] * \Sigma_j i \Sigma_j V(y,i,j) \text{ for } i=1 \text{ to } 10, j=1 \text{ to } 6$$

where CM(x) and CM(y) are the center of mass coordinates in the X and Y directions with respect to the computerized representation of the electrode grid. V(x,i,j) and V(y,i,j) are, respectively, the variances V of the ten highest variance peaks i=1 to 10 and six ATM parameters j=1 to 6 with respect to (x,y) location. The centers of mass were therefore an average of the six ATM parameters (amplitude, vertical shift, phase lag, duration, MSE, and the mean of these parameters). Activation maps of ventricular tachycardia were used to locate the central common pathway of the reentrant circuit. The center of the narrowest region of the central common pathway, determined by activation mapping during ventricular tachycardia, was used as a spatial marker to compare with location of the center of mass of ATM weight variability peaks. We chose this as a marker because it is usually an area of slowed conduction in the canine model of a reentrant circuit (21) and thus might be a good candidate region for ablation (30, 27, 28). The Euclidean distance (X,Y) between centers of mass of the variance peaks and the center of the narrowest width of the central common pathway was calculated and tabulated.

B) RESULTS

1) Activation Patterns and Locations of Functional Lines of Block

Figure 24A:
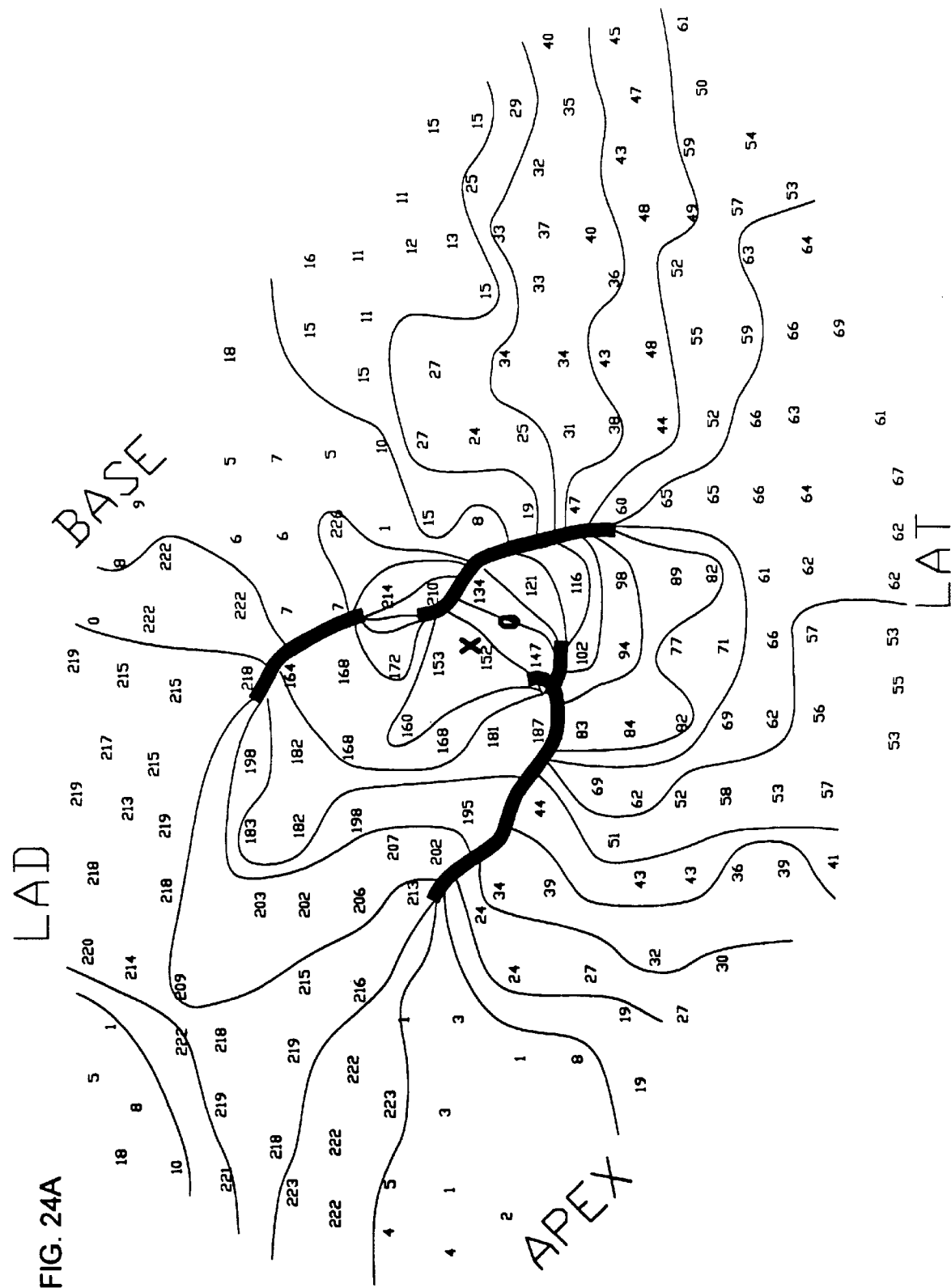
FIGS. 24A–24D Activation maps are shown for experiment 2 (Table 1) during ventricular tachycardia (Panel A), sinus rhythm (Panel B), LAD pacing (Panel C) and pacing from the base (Panel D). In Panel A, the functional lines of block are thick black lines that bound the central common pathway during reentry. The arrows mark the direction of propagation of the activating wavefront. The large numbers give isochrone times. The small numbers are the activation times at individual sites. The location of the electrode grid with respect to the LAD and lateral margins, and the apex and base of the left ventricle, are shown. Further explanation is given in the text.
Figure 24B:
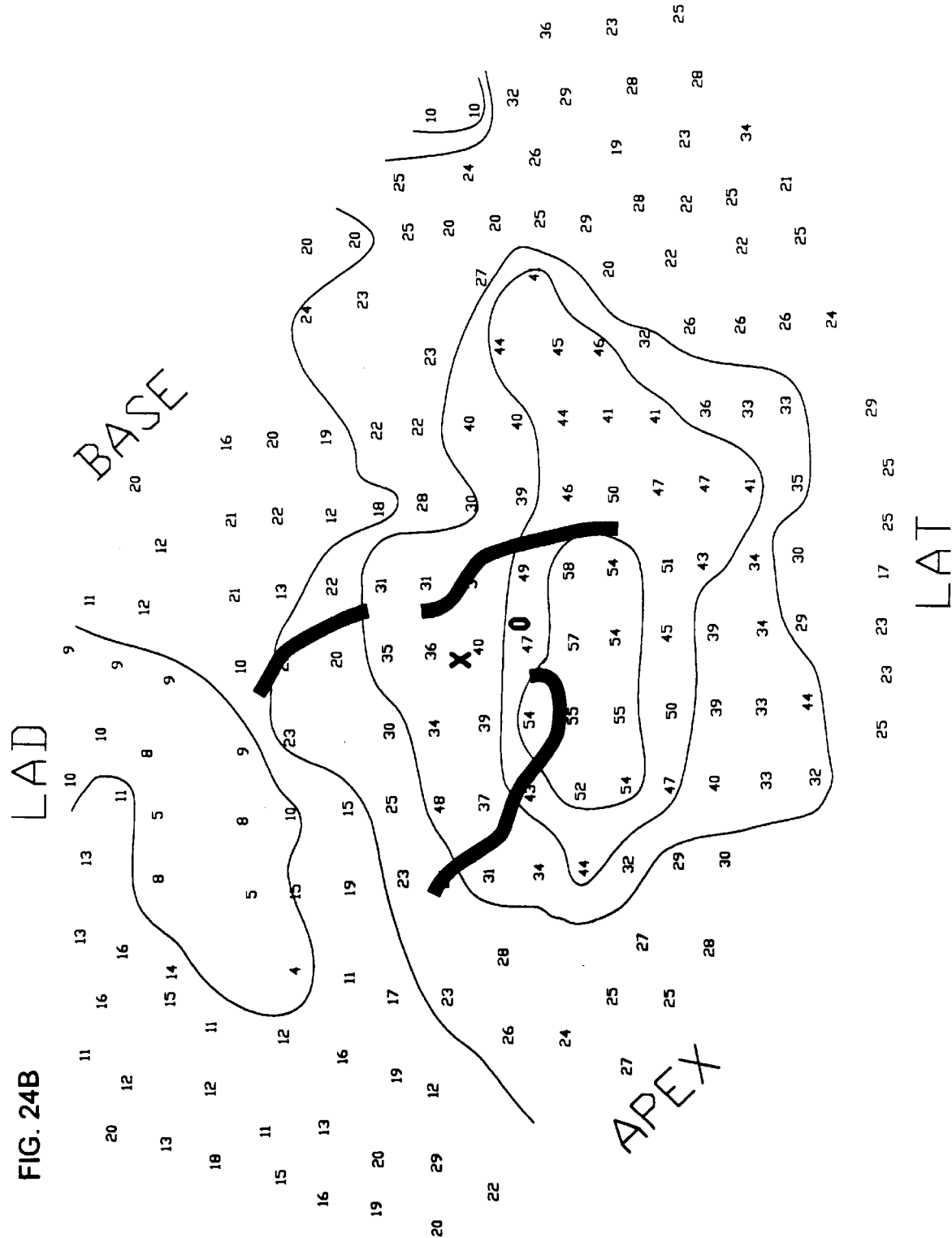
Figure 24C:
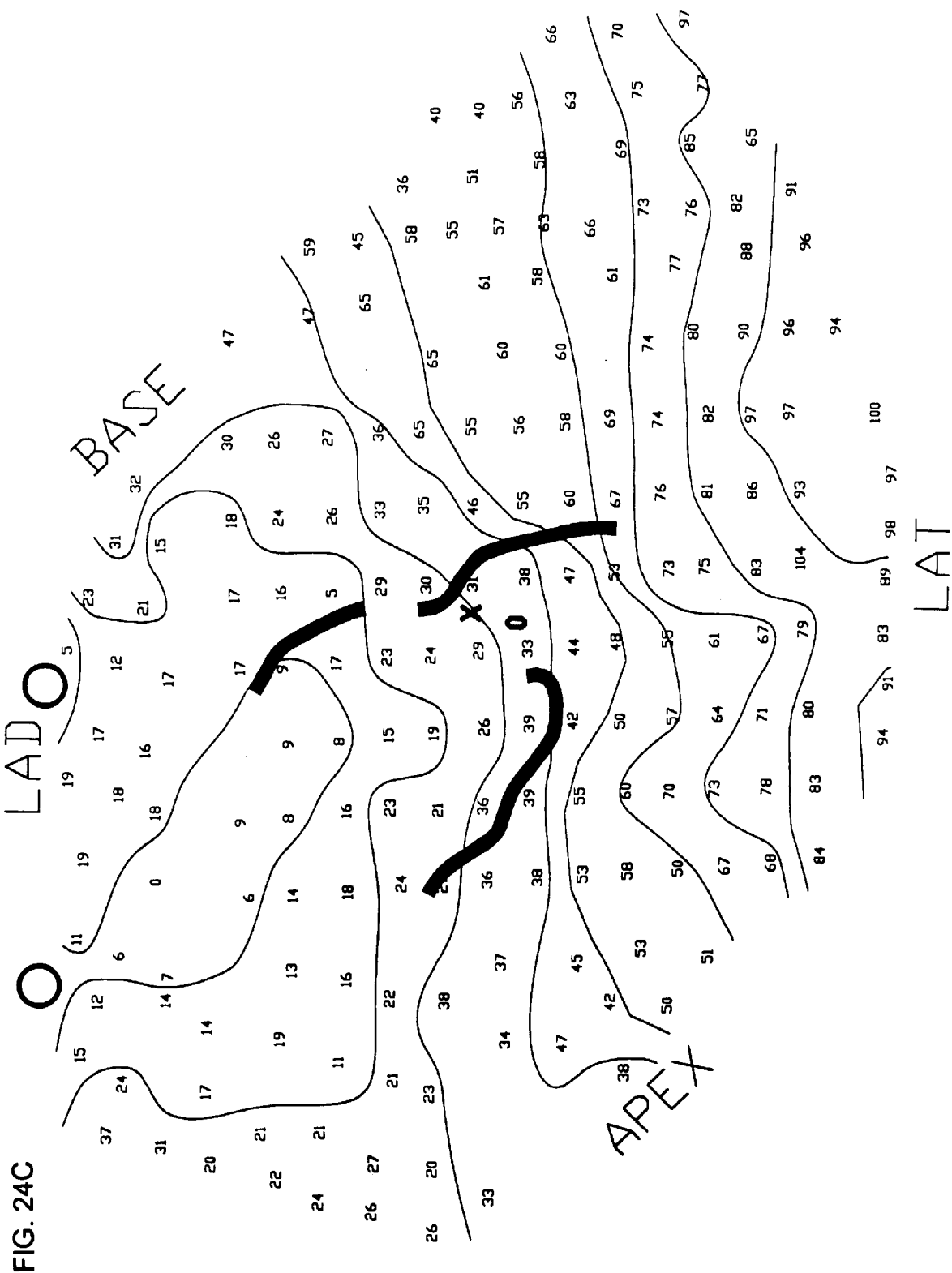
Figure 24D:
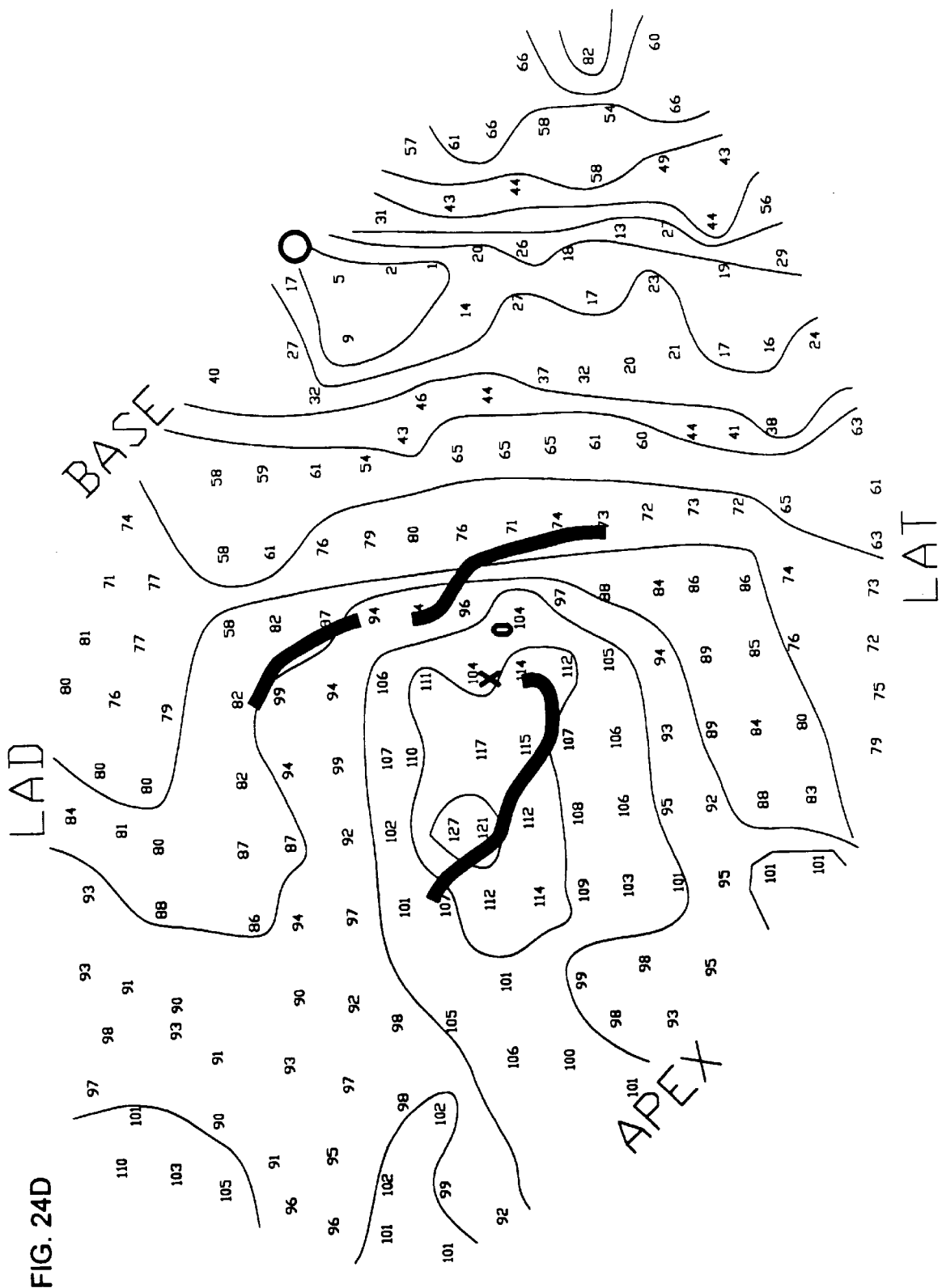
Figures 25A, 25B, 25C, 25D:
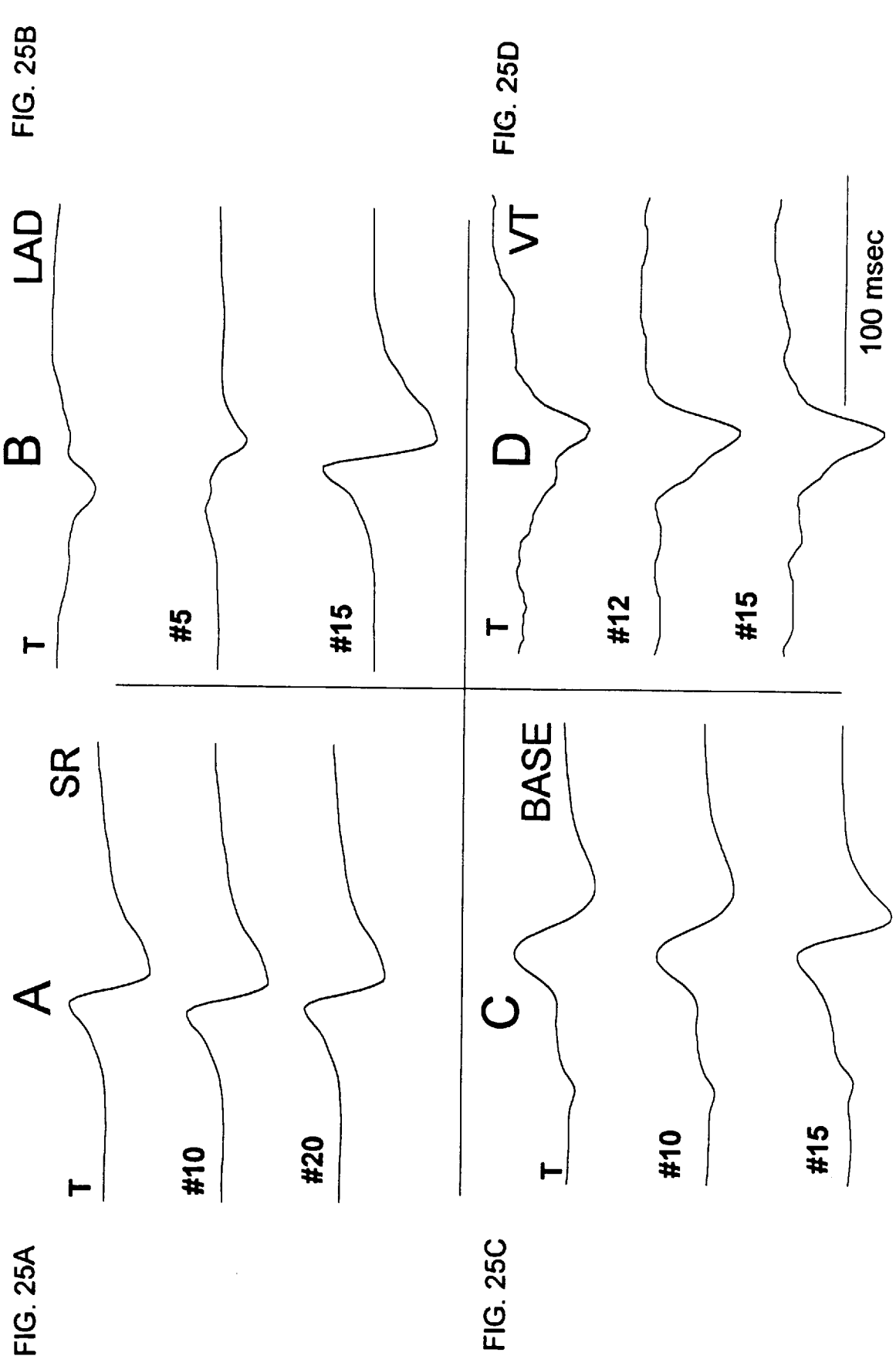
FIGS. 25A–25D Examples of template electrogram (T) and input electrograms (cycle number is labeled) for site 46 of experiment 2A. During sinus rhythm there is minimal change between the template and the input electrograms for cycles 10 and 20. Electrograms changed during pacing from the LAD (Panel B) and base (Panel C), and during ventricular tachycardia (Panel D).
Figure 28A:
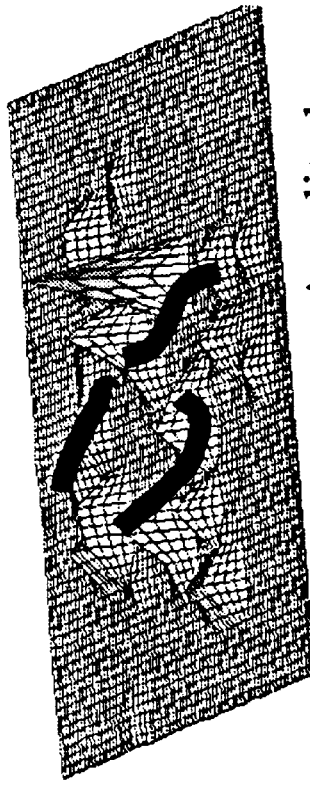
FIGS. 28A–28D ATM weight variability peak maps constructed from LAD pacing data are given for experiment 2 and described in FIG. 27. The largest variance peaks often reside adjacent to functional lines of block, however, there are peaks away from block lines particularly in Panels A, B, and D. The panels show the ATM weight variability doe amplitude (panel A), phase lag (panel B), duration (panel C), and normalized mean variance (panel D).
Figure 28B:
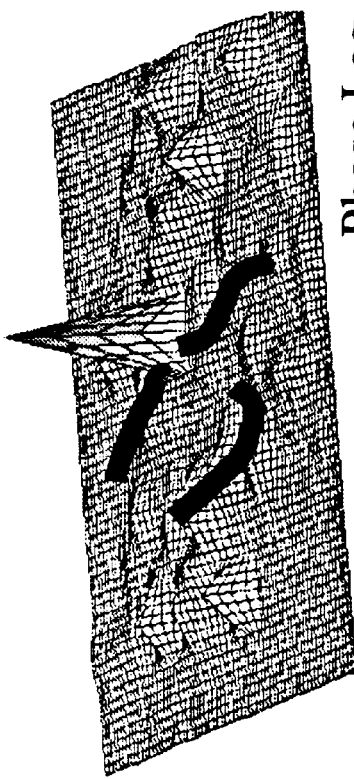
Figure 28C:
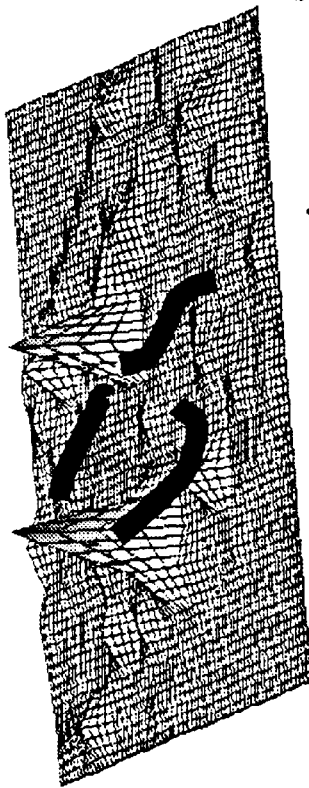
Figure 28D:
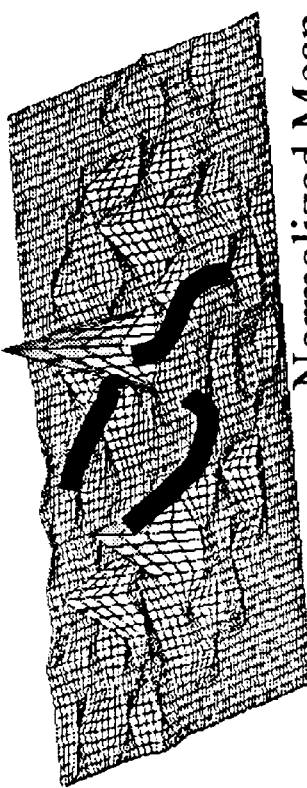
Figure 30:
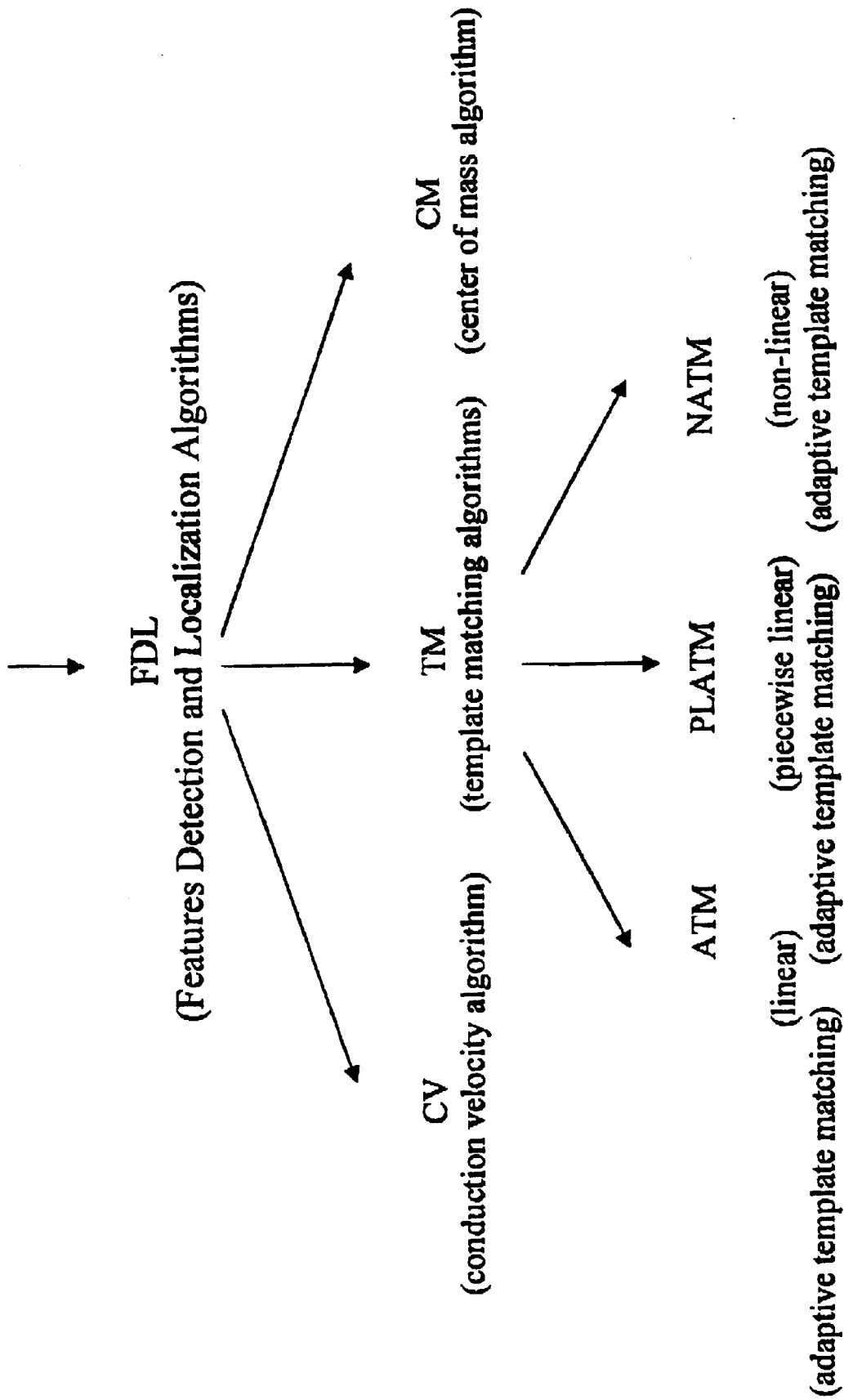
FIG. 30 Algorithm—the names of algorithms used in this invention and their relationships are shown.
Figure 34:
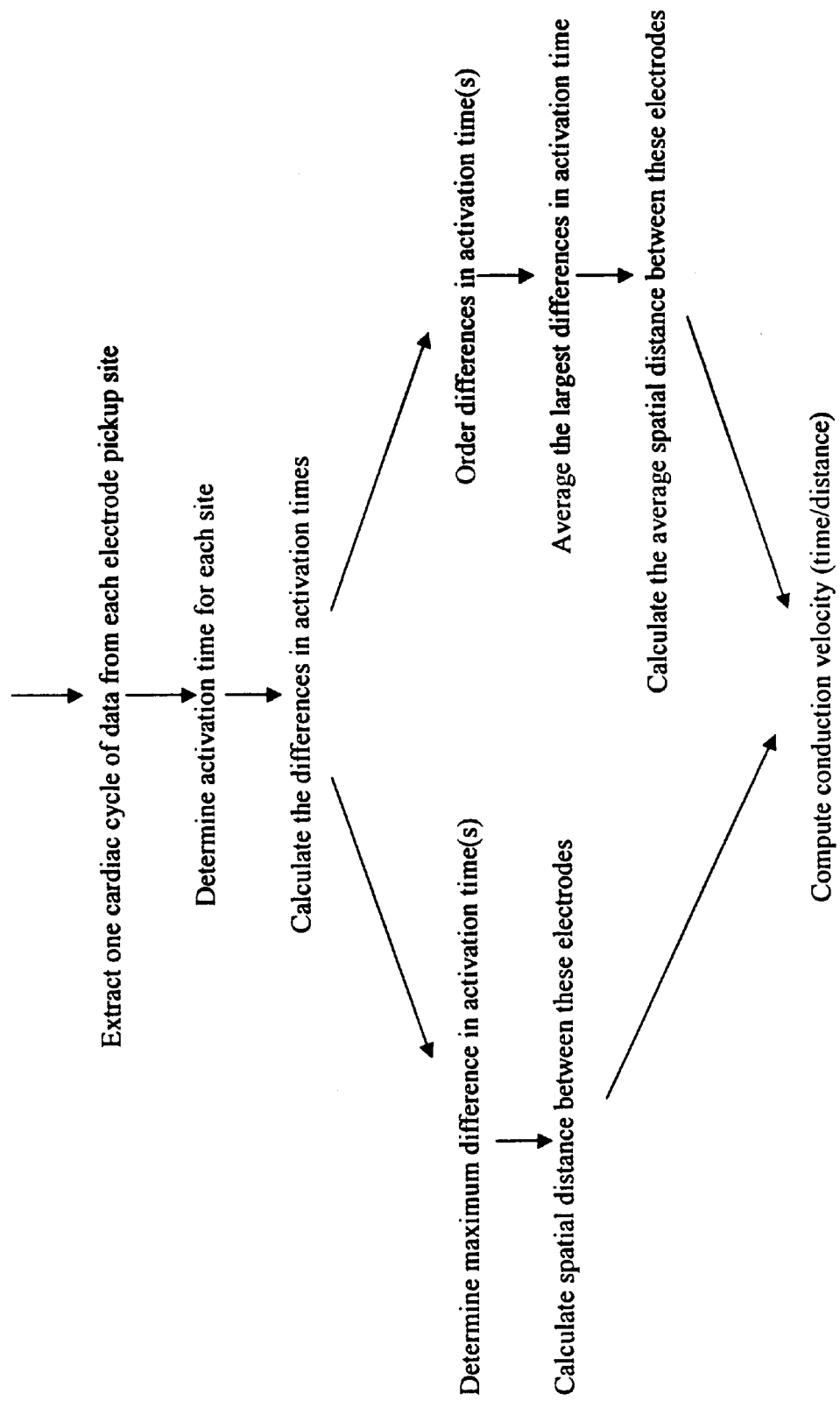
FIG. 34 CV—flow chart of the conduction velocity (CV) algorithm. The procedure to obtain and process the data to determine the magnitude and direction of the propagating wavefront with respect to the local site are given.
Figure 35:
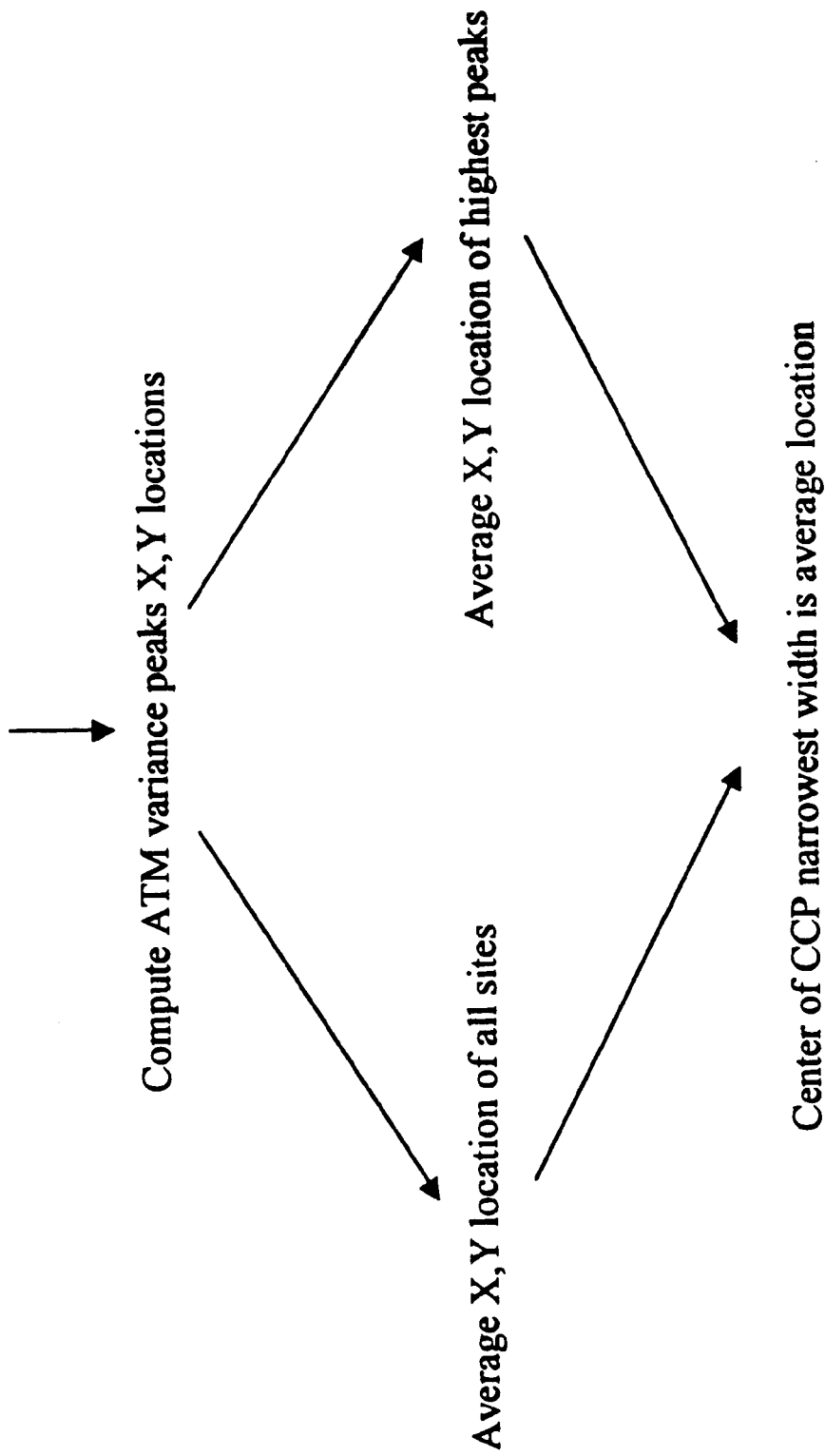
FIG. 35 CM—flow chart of the non-linear center of mass (CM) algorithm. The procedure to process the ATM weight variability peaks to determine the location of the narrowest CCP width are given.
Figure 36:
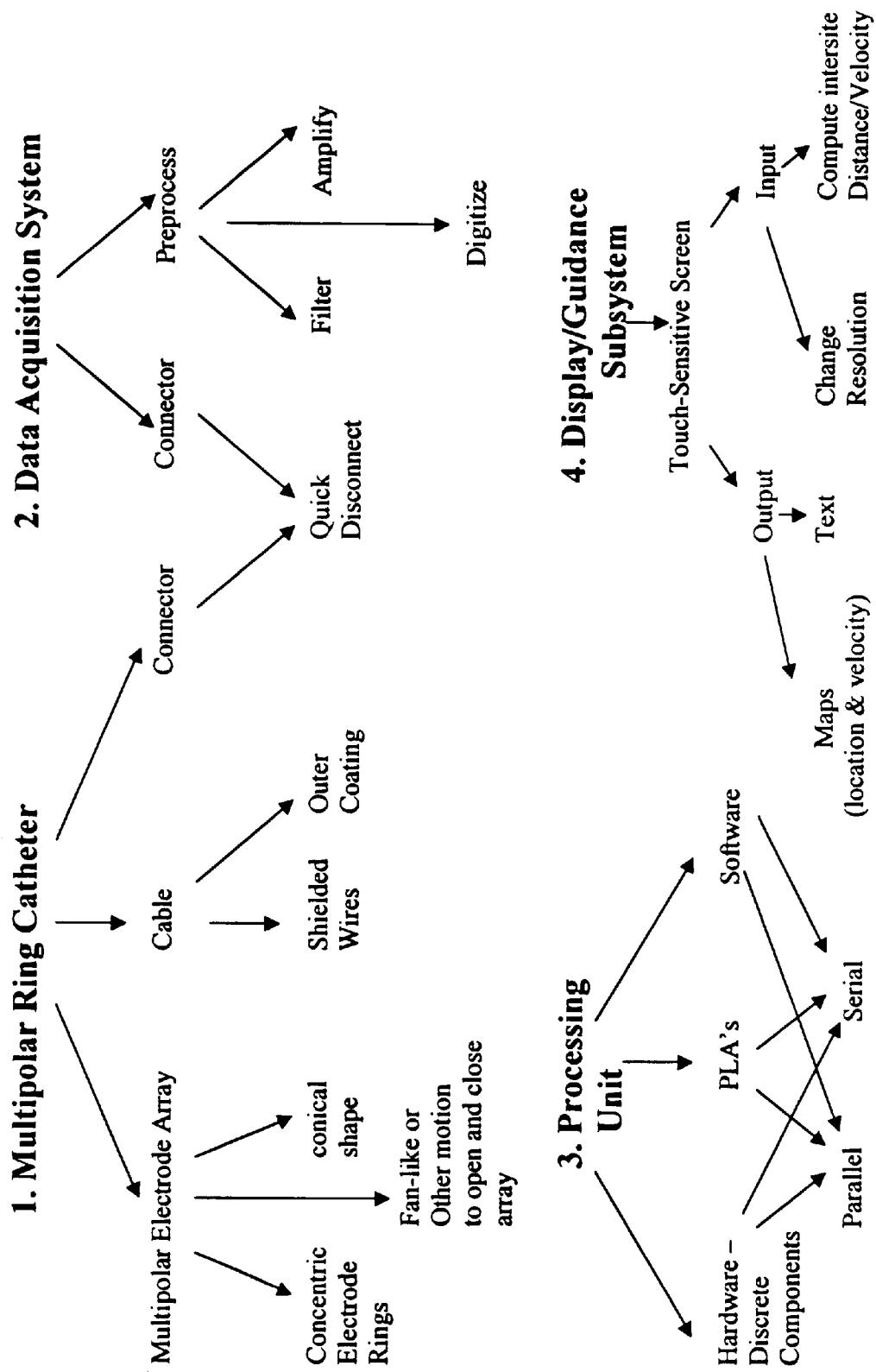
FIG. 36 Device—flow chart of the device subsystems and their major components are given.
Figure 38:
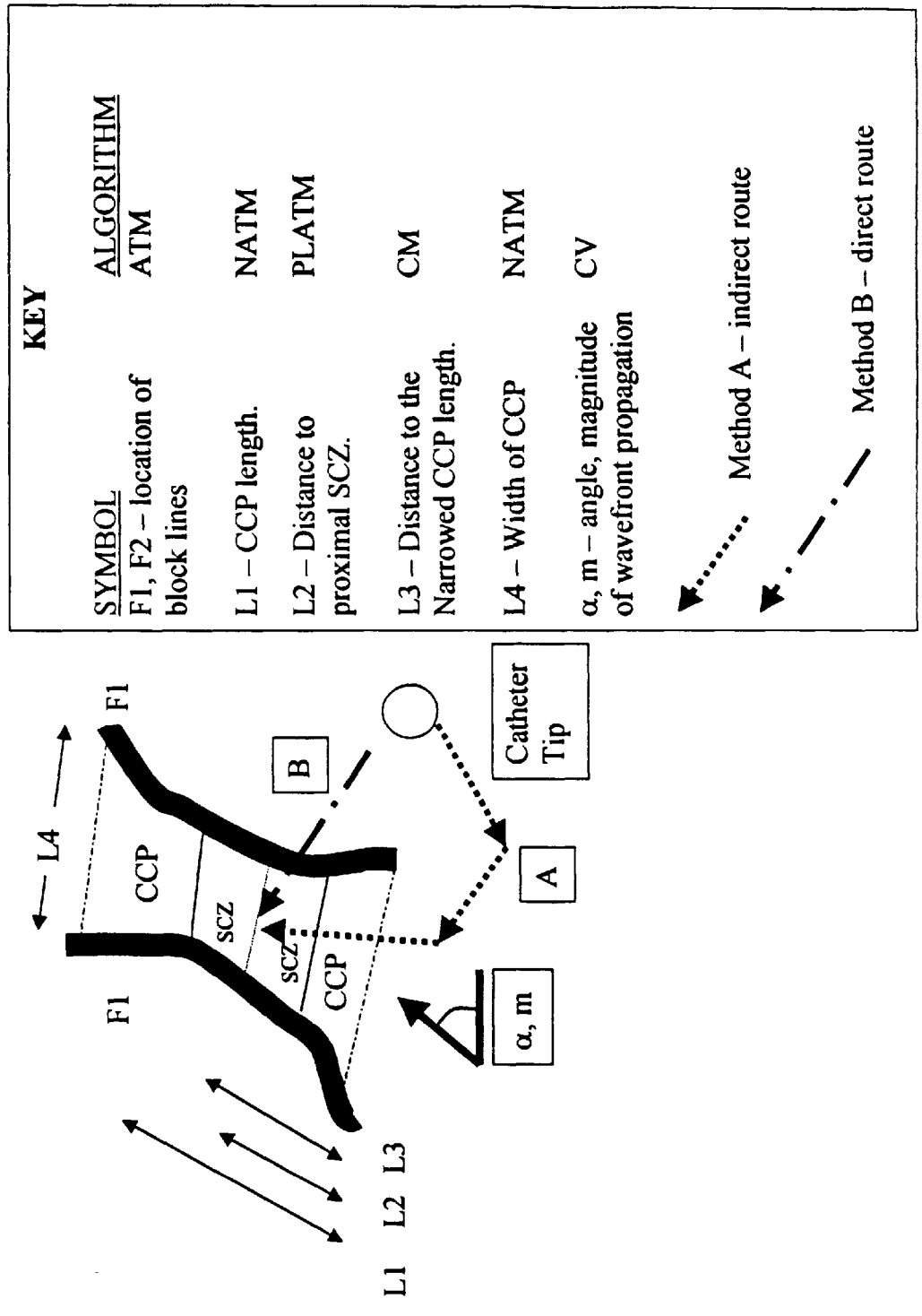
FIG. 38 Details of the display/guidance subsystem—the features exhibited by the display/guidance subsystem following quantification with RCFs algorithms are shown. The display is touch sensitive and accepts input. For example, the distance and velocity between any two points on the screen can be displayed.

Activation maps were constructed for all ventricular tachycardias to locate the reentrant circuits and the functional lines of block. FIG. 24A shows an activation map of the reentrant circuit during the unsustained ventricular tachycardia, which occurred during experiment 23A (Table 1). There are two approximately parallel functional lines of block (thick black line) bounding the central common pathway of the reentrant circuit. The central common pathway is located near the center of the electrode grid. The entrance to the central common pathway begins at around isochrone 90 (given in large numbers) and the exit of the central common pathway occurs at about isochrone 200. The propagating impulse exits toward the LAD/apical margin and bifurcates into two separate activating wavefronts. One activating wavefront courses around a functional line of block along the apical margin (at the left), toward the lateral margin of the grid. The other activating wavefront courses around the other functional line of block along the basal margin (at the right) and also propagates toward the lateral margin of the grid. The two wavefronts coalesce at the entrance to the central common pathway near the lateral margin. After the functional lines of block were located they were projected onto activation maps during sinus rhythm and ventricular pacing. In FIG. 24B, the sinus rhythm activation map is shown with the locations of the functional lines of block that were present for this same experiment during tachycardia (but not during sinus rhythm) superimposed as thick black lines. Activation begins around the margin of the electrode array and progresses toward the center which is activated last (isochrones 50–60) as is the pattern that occurs when there are no intramural connections (1). The last region to be activated overlaps partially with the location of the central common pathway (17, 18). FIG. 24C shows the activation pattern during stimulation at the LAD electrodes with the locations of the functional lines of block that were present during tachycardia (but not during LAD pacing) also superimposed as thick black lines. Activation progresses from the LAD margin toward the lateral margin without any evidence of conduction block or change in activation pattern in the region where the central common pathway was located during tachycardia. During pacing from the base (FIG. 3D), activation moving from the base toward the center of the electrode array is slower than during LAD pacing because the wavefront is moving transverse to the long axis of the myocardial fibers (1). The wavefront also moves from the margins of the border zone toward the center and the last region to be activated is the central common pathway of the tachycardia reentrant circuit. Similar maps were constructed for all experiments listed in Table 1.

2) Changes in Electrogram Morphology

The changes that occurred in electrogram morphology that were quantified by ATM during sinus rhythm, ventricular pacing and ventricular tachycardia were related to the regions in the EBZ where the electrograms were recorded and the location of the functional lines of block during tachycardia. FIG. 4 shows examples of changes in electrogram morphology at recording site 46 in FIG. 24 which is adjacent to the right functional line of block. Each panel shows the template electrogram (T) and electrograms selected during two of the 50 cycles of ATM recorded at the same site during sinus rhythm (Panel A), LAD and base pacing (Panel B and C) and ventricular tachycardia (Panel D). The electrograms are similar for all the illustrated cycles during sinus rhythm but they have changed during pacing and ventricular tachycardia. A plot of the cycle-to-cycle changes in ATM optimal weighting magnitudes for amplitude, phase lag, duration, and mean square error (MSE, shape) is shown in FIG. 5. The figure shows the changes that occurred over the entire 50 cycles that were analyzed at site (46) and at some other selected sites (55, 78, and 58 in FIG. 24) for the different rhythms. Electrograms show the least cycle-to-cycle changes in sinus rhythm. Large cycle-to-cycle changes are apparent during pacing and ventricular tachycardia although the magnitude of the changes differs at the recording sites. In general, sites 46 and 55 which are located closest to the functional lines of block in the reentrant circuit show the largest cycle-to-cycle changes, whereas sites 78 and 58 which are located farthest from functional lines of block show the least cycle-to-cycle changes.

3) Variance Maps

The changes in electrogram morphology as shown in FIG. 26 were expressed as three dimensional variance maps. FIG. 27 shows examples of the variance maps for the ATM parameters for signals acquired during sinus rhythm for Tachycardia 2A. High variance peaks are shown to occur at or adjacent to the functional lines of block for the amplitude parameter (panel A; 84% association), phase lag parameter (panel B; 67% association), duration parameter (panel C; 43% association), and normalized mean parameter (panel D; 54% association). FIG. 28 shows the variance maps for the ATM parameters for signals acquired during LAD pacing. High variance peaks are shown to occur at or adjacent to the functional lines of block for the amplitude parameter (panel A; 68% association), phase lag parameter (panel B; 74% association), duration parameter (panel C; 82% association), and normalized mean parameter (panel D; 69% association). FIG. 29 shows the variance maps for the ATM parameters for signals acquired during ventricular tachycardia in this same experiment. High variance peaks are shown to occur at or adjacent to the functional lines of block for the amplitude parameter (panel A; 85% association), phase lag parameter (panel B; 88% association), duration parameter (panel C; 95% association), and normalized mean parameter (panel D; 93% association).

TABLE 5

PERCENT ASSOCIATION OF ATM weight variability PEAKS WITH LINES OF BLOCK (MEAN STANDARD ERROR)

| Rhythm | Amplitude | Vert. Shift | Phase Shift | |
|---|---|---|---|---|
| SR | 59.5 ± 5.9 | 73.5 ± 5.1 | 57.9 ± 6.4 | |
| LAD | 66.1 ± 5.9 | 71.9 ± 5.5 | 64.8 ± 6.1 | |
| CENTER | 68.5 ± 4.9 | 64.8 ± 8.8 | 65.2 ± 6.1 | |
| LAT | 55.7 ± 10.4 | 74.7 ± 6.3 | 64.3 ± 8.9 | |
| BASE | 75.1 ± 9.6 | 53.8 ± 20.2 | 68.4 ± 6.6 | |
| <PACE> | 66.4 ± 4.0 | 66.3 ± 4.7 | 65.7 ± 0.9 | |
| VT | 93.2 ± 1.9 | 83.7 ± 4.6 | 84.4 ± 4.5 | |

| Rhythm | Duration | MSE | Norm $\mu$ | Mean |
|---|---|---|---|---|
| SR | 61.4 ± 5.4 | 52.7 ± 7.1 | 67.0 ± 4.5 | 61.1 ± 3.9 |
| LAD | 62.2 ± 6.2 | 54.7 ± 9.2 | 72.1 ± 5.1 | 65.5 ± 4.7 |
| CENTER | 62.9 ± 5.3 | 56.4 ± 11.6 | 67.7 ± 5.7 | 64.4 ± 4.7 |
| LAT | 56.9 ± 6.6 | 52.3 ± 11.8 | 66.3 ± 6.4 | 61.7 ± 4.9 |
| BASE | 81.9 ± 8.6 | 39.9 ± 8.8 | 63.8 ± 12.4 | 63.8 ± 6.7 |
| <PACE> | 66.0 ± 5.5 | 50.8 ± 3.7 | 67.5 ± 1.7 | 63.9 ± 0.8 |
| VT | 88.1 ± 3.2 | 80.8 ± 5.7 | 89.0 ± 2.2 | 86.5 ± 2.5 |

Legend for Table 5 above
Rhythm = rhythm type.
Vert. Shift = the vertical shift or average baseline of the signal.
Norm $\mu$ = the mean of the amplitude, vertical shift, phase shift, duration, and MSE variances following normalization.
Mean = the mean of the amplitude, vertical shift, phase shift, duration, MSE, and Norm $\mu$ variances.
<PACE> = mean for all pacing data.

Table 5 shows the mean association for all experiments of the variance peaks with functional lines of block, for.sinus rhythm and pacing at all sites. Also included in the table, is the mean association of variance peaks with functional lines of block during tachycardia which has been published (21). The mean value for association of all ATM parameters with the functional lines of block are also shown in Table 5. The vertical shift parameter, while included for completeness of the two dimensional algorithmic scale and shift operations because it provides independent information that is necessary to compute ATM weights (see 21), has doubtful physiological significance. For sinus rhythm, excluding baseline shifts, the normalized mean variance (67.0%), and the duration variance (61.4%) provided the best correlation while the MSE correlation (52.7%) was the poorest. Overall, the mean correlation for all parameters with the location of the functional lines of block during sinus rhythm was 61.1%. For ventricular pacing, the association of variance peaks for the different ATM parameters with the functional lines of block was dependent on the site of stimulation. The ATM parameter for normalized mean variance (72.1%) provided the best correlation for LAD pacing, while the MSE parameter provided the poorest (54.7%). For center pacing the amplitude parameter provided the best correlation (68.5%) while the MSE parameter was the poorest (56.4%). For lateral pacing, excluding baseline shifts, the normalized mean variance provided the best correlation (66.3%) while the MSE parameter was the poorest (52.3%). For base pacing the duration parameter provided the best correlation (81.9%) while the MSE parameter was the poorest (39.9%). The mean association of all variance peaks with functional lines of block for pacing from the LAD (65.6%), center (64.4%), lateral (61.7%), and base (63.8%) were not significantly different from each other. The mean association of variance peaks with functional lines of block for all pacing sites are, amplitude (66.4%), vertical shift (66.3%), phase lag (65.7%), duration (66.0%), MSE (50.8%) and normalized mean variance (67.5%) with a mean of 63.9% for the combined data. The correlation of the variances for all ATM parameters (amplitude, duration, phase lag, MSE, and the mean of all parameters) during sinus rhythm and pacing from each of the sites, was less than the correlation of these parameters during ventricular tachycardia (mean association 86.5%, Table 5).

4) Center of Mass

The Euclidean distances between the mean centers of mass of the ten highest variance peaks during sinus rhythm and pacing, to the position of the narrowest width of the central common pathway at the point equidistant between the bounding functional lines of block, are given in Table 6. All centers of mass were referenced with respect to an arbitrary (0,0) location at the top left-hand corner of the computerized grid. The mean center of mass for pacing data has a smaller mean Euclidean distance (0.61 cm) than the sinus rhythm center of mass (1.04 cm) in Table 6. The smallest Euclidean distance occurred during experiment 11 for the center of mass computed from ATM pacing data (0.22 cm) and during experiment 6 for the sinus rhythm data (0.42 cm). All pacing centers of mass resided within the central common pathway of the figure of eight reentrant circuit for all experiments (Table 6, column labeled PACE LOC). However the center of mass locations of variance peaks computed from sinus rhythm data resided within the central common pathway in only 5 of 12 experiments (Table 6, column labeled SR LOC). The center of mass location of variance peaks computed from sinus rhythm data resided on the edge of a functional line of block bounding the central common pathway in three experiments and outside of the central common pathway in four experiments.

TABLE 6

CENTERS OF MASS LOCATIONS

| Exp | X (cm) | $X_{pace}$ (cm) | $X_{SR}$ (cm) | Y (cm) | $Y_{pace}$ (cm) |
|---|---|---|---|---|---|
| 1 | 5.13 | 5.97 | 6.77 | 3.75 | 4.12 |
| 2 | 6.53 | 6.31 | 6.01 | 5.04 | 4.45 |
| 3 | 5.82 | 6.03 | 5.79 | 5.41 | 4.85 |
| 4 | 6.47 | 5.83 | 5.82 | 3.89 | 3.81 |
| 5 | 6.36 | 6.80 | 7.40 | 5.43 | 4.15 |
| 6 | 7.08 | 6.75 | 7.14 | 4.88 | 5.21 |

TABLE 6-continued

CENTERS OF MASS LOCATIONS

| | | | | | |
|---|---|---|---|---|---|
| 7 | 6.55 | 6.41 | 7.11 | 4.99 | 4.74 |
| 8 | 6.35 | 6.42 | 6.17 | 4.81 | 4.50 |
| 9 | 6.77 | 6.60 | 6.59 | 5.25 | 4.20 |
| 10 | 6.44 | 6.51 | 6.70 | 4.63 | 4.30 |
| 11 | 6.43 | 6.49 | 6.85 | 3.69 | 3.48 |
| 12 | 7.40 | 7.96 | 6.69 | 3.73 | 3.75 |
| Mean | 6.44 | 6.51 | 6.59 | 4.63 | 4.30 |

| $Y_{SR}$ (cm) | $ED_{Pace}$ (cm) | $ED_{SR}$ (cm) | PACE LOC | SR LOC |
|---|---|---|---|---|
| 4.76 | 0.92 | 1.92 | In | Out |
| 4.32 | 0.63 | 0.89 | In | In |
| 4.72 | 0.60 | 0.69 | In | Out |
| 3.92 | 0.64 | 0.65 | In | In |
| 4.01 | 1.35 | 1.76 | In | Edge |
| 5.29 | 0.47 | 0.42 | In | In |
| 3.26 | 0.29 | 1.82 | In | Out |
| 3.85 | 0.31 | 0.98 | In | Edge |
| 4.16 | 1.02 | 1.06 | In | In |
| 3.67 | 0.34 | 0.99 | In | Out |
| 3.87 | 0.22 | 0.46 | In | In |
| 4.12 | 0.56 | 0.81 | In | Edge |
| 4.16 | 0.61 | 1.04 | — | — |

Legend for Table 6 above
Exp = experiment number
X = location of the center of the narrowest central common pathway width in the X direction.
Y = location of the center of the narrowest central common pathway width in the Y direction.
$X_{pace}$ = X location of center of mass of 10 highest variance peaks during pacing.
$Y_{pace}$ = Y location of center of mass of 10 highest variance peaks during pacing.
$X_{SR}$ = X location of center of mass of 10 highest variance peaks during SR.
$Y_{SR}$ = Y location of center of mass of 10 highest variance peaks during SR.
$ED_{Pace}$ = Euclidean distance from center of mass of 10 highest variance peaks, to center of the narrowest central common pathway width, during pacing.
$ED_{SR}$ = Euclidean distance from center of mass of 10 highest variance peaks, to center of the narrowest central common pathway width, during sinus rhythm.
PACE LOC = location of mean center of mass of the 10 highest variance peaks during pacing, with respect to the central common pathway.
SR LOC = location of the center of mass of the 10 highest variance peaks during sinus rhythm, with respect to the central common pathway.
In, Out = within, outside of the central common pathway.
Edge = overlying a line of block bounding the central common pathway.

The relationship between the ATM weight variability peak centers of mass and the location of the narrowest central common pathway width is shown in FIG. 24 for experiment 2. The center position of the narrowest width of the central common pathway during reentrant ventricular tachycardia is marked by an "O" in the activation map of FIG. 24A. It is also projected onto the activation maps generated from sinus rhythm, and LAD and base pacing (FIGS. 24B–D) The mean variance peaks centers of mass computed from ATM analysis of the combined pacing and sinus rhythm data are marked by an "X" in FIG. 24A. The individual mean centers of mass of ATM weight variability peaks for sinus rhythm (FIG. 24B) and pacing at the LAD and base (FIGS. 24C–D) are also denoted by an X and they all reside within the central common pathway for this experiment. All variance peak centers of mass lie close to the location of the position of the center of the narrowest width of the central common pathway during ventricular tachycardia.

C. DISCUSSION

1) Location of Reentrant Circuits Causing Ventricular Tachycardia

Ventricular tachycardia late after myocardial infarction is often caused by reentry in the infarct region (1–11PLATM:29, 26, 31, 32, 33, 34, 35, 36, 27, 37, 28). These arrhythmias are sometimes difficult to abolish by ablation methods because the reentrant circuits often cannot be located with precision. In addition, identification of regions of the circuit where relatively small lesions can interrupt reentry, although desirable, cannot be accomplished because high-resolution activation maps of the circuits are rarely obtained (41). Ideally, a narrow region essential for continuation of reentry, such as an isthmus between regions of block would be the most appropriate target. Therefore, besides knowing if the pacing/ablation site resides in the circuit, it would be very useful to know the relationship between the proposed site and the bounding lines of block that contribute to reentry. Usually static measurements obtained during single cardiac cycles or several cardiac cycles, are used as part of the methodology to localize circuits and prospective sites for ablation. One of the most successful approaches is the location of a putative zone of slow conduction based on the characteristics and timing of electrograms recorded during tachycardia, followed by determination of whether pacing at that site results in concealed entrainment (38, 34, 35, 36) However, limitations of this approach are that it may involve multiple inductions of tachycardia, and stimulation at multiple sites during tachycardia both of which may be very time consuming, and it does not always locate the most optimum region in the circuit for ablation (38, 35, 36, 39, 40, 41, 42).

In attempts to eliminate the necessity for multiple inductions of tachycardia, accurate mapping of the circuits and the possibility of long protocols involving stimulation of the heart from multiple sites during tachycardia, methods to locate potential arrhythmogenic regions during sinus rhythm or pacing without tachycardia induction, have been studied (10, 11, 43, 44, 12, 17, 15, 45, 18, 46, 16). The hypothesis that electrogram characteristics determined during single beats of rhythms other than tachycardia might be useful is based on the premise that regions of slow and nonuniform conduction that are needed for reentry can be located during sinus rhythm or pacing on the basis of specific electrogram features such as low amplitude, long duration, fractionation, or occurrence during diastole (10, 44, 12, 15, 45, 18, 46, 16). However, the correlation between these electrogram characteristics and reentrant circuit location in general has not been satisfactory. Therefore the actual electrogram shape during single cycles has not proven to be a good indicator of the location of the recording site with respect to the circuit or more specifically, a narrow isthmus of conduction that might occur in the circuit such as the central common pathway. The likely explanation for the lack of specificity is that regions of slow, nonuniform activation that are associated with electrograms with the abnormalities described above, exist in regions of infarct border zones which are not involved in reentry. Any additional special electrophysiological properties leading to reentry have not been identified in static electrogram morphology.

Because of the limitations of characterizing electrograms for single beats for the localization of reentrant circuits, we tested the hypothesis in our previous study that dynamic changes of electrogram features from cycle to cycle during tachycardia might be indicative of reentrant circuit location (21). This hypothesis was based on the premise that conduction in regions where functional lines of block form in reentrant circuits is inherently unstable because mechanisms causing functional block involve some variabilities in conduction patterns which might be detected as cycle to cycle variabilities in electrogram features. However, a method was needed to precisely quantify these variabilities. For this purpose we modified the adaptive template methodology previously described by Widrow et al (20), to detect cycle to cycle changes in electrogram amplitude, duration, phase lag and shape. The ATM algorithm adapts weights that shift and scale the input signal so that it has optimal overlap with the template, based on an estimate of the mean square error between the template and input signals (23). When the mean square error is minimized, the weights provide a quantitative measure of the difference in signal shape between the template and input signals. The results of dynamic electrogram measurements using that methodology showed that the greatest cycle-to-cycle variability in electrograms during tachycardia does occur in the vicinity of the functional lines of block in reentrant circuits and that variances in ATM parameters can be used to locate functional lines of block and the central common pathway in figure of eight circuits in this canine model of infarction.

In the present study we applied the ATM methodology to the analysis of electrogram cycle to cycle changes during sinus rhythm and ventricular pacing. The hypothesis that we tested was that the regions where the functional lines of block formed when tachycardia was induced were not randomly located since multiple inductions of tachycardia results in similar reentrant circuit location (47, 48, 49) predetermined by special and unique electrophysiological characteristics. One determinant of these special characteristics in the canine infarct model that we used may be remodeling of gap junction location (64, 50, 51, 5) and nonuniform anisotropic conduction related to the remodeling (52, 1, 53). Although slow and nonuniform conduction can give rise to low amplitude or fractionated electrograms at sites remote from reentrant circuits, specific conduction properties conferred on it by these special anatomical characteristics i.e. remodeled gap junctions, would be located only at the site of the circuit. Although the unique electrophysiological properties where the functional lines of block form, have not yet been precisely defined and quantified, they might be detected as specific dynamic changes in electrograms.

The ATM method was used with further modification to quantify these changes. The ATM algorithm uses a convergent coefficient to determine the rate at which the weights adapt toward the weighting for best overlap of the template with the input signal. This convergent coefficient was held constant in a previous study (21); however, better overlap can be obtained (and therefore a better estimate of the changes in shape of template versus input signals) by optimizing the coefficient. This was done in the present study by adjusting the coefficient upward or downward until the mean squared error was minimized during the matching process. Since changes in electrogram morphology are smaller during sinus rhythm and ventricular pacing than during ventricular tachycardia (see FIG. 5), adjustment of the coefficient, which provided a more accurate quantification, was used for analysis of sinus rhythm and pacing data. The ATM weight estimation is done over many data points (100) making the method robust to random noise while preserving the measurements of cycle-by cycle variability in the data. Although signal averaging methods for detecting electrogram morphology are also robust to random noise, they eliminate cycle-to-cycle variability in the data and therefore are not useful for dynamic, cycle-to-cycle measurements. (65,66).

In this study we also added the center of mass determination to our analysis and found that during pacing, it was an excellent locator of the central common pathway. The center of mass measurement averages the positions of the highest ATM weight variability peaks in the x direction and in the y direction on the computerized grid. This average XY location is the center of mass. The method was used because it was our hypothesis that the average location of the functional lines of block bounding the central common pathway would approximately coincide with the center of the central common pathway at its narrowest width. Therefore, if the highest variance peaks are a good indicator of the positions of the functional lines of block, then the XY center of mass of these peaks would be useful as a locator of the center of the central common pathway. For clinical radiofrequency catheter ablation of the reentrant circuit using a linear lesion, it is important to determine the best direction that the line should have and to minimize its length. Knowing the locations of the bounding functional lines of block and the position of the narrowest width of the central common pathway using ATM analysis is potentially helpful to do this.

2) Limitations and Future Directions

We have shown that ATM analysis of dynamic electrogram characteristics during sinus rhythm, ventricular pacing and ventricular tachycardia, and the center of mass of the electrogram variances, are able to locate functional lines of block in reentrant circuits caused by anisotropic reentry in a canine model of healing infarction. However, it must still be determined if this method can be applied to the location of reentrant circuits in human ventricular tachycardia. As we have discussed, we attribute the instabilities in electrogram features to the functional nature of the lines of block and the remodeling of gap junctions. Similar remodeling has also been described in ischemic and infarcted human myocardium (54, 55, 56, 57, 58, 59, 61, 62, 67) and functional reentry caused by anisotropy may cause some clinical ventricular tachycardias (48, 63, 49).

However, reentrant circuits in humans may be dependent on regions of anatomical as well as functional block and it is unknown whether electrograms have high variances in these regions. Current studies that are underway to analyze electrograms in human patients with reentrant ventricular tachycardia should provide the answer.

REFERENCES FOR EXPERIMENT #3

1. Dillon S M, Allessie M A, Ursell P C, Wit A L. Influences of anisotropic tissue structure on reentrant circuits in epicardial border zone of subacute canine infarcts. Circ Res 1988; 63:182–206.
2. Coromilas J, Saltman A E, Waldecker B, Dillon S M, Wit A L. Electrophysiologic effects of flecainide on anisotropic conduction and reentry in infarcted canine hearts. Circulation 1995; 91:2245–2263.
3. Costeas C, Peters N S, Waldecker B, Ciaccio E J, Wit A L, Coromilas J. Mechanisms causing sustained ventricular tachycardia with multiple QRS morphologies: results of mapping studies in the infarcted canine heart. Circulation 1997; 96:3721–3731.
4. Josephson M E. Clinical Cardiac Electrophysiology: Techniques and interpretations. $2^{nd}$ Ed. Lea and Febiger, Philadelphia 1993.
5. Peters N S, Coromilas J, Severs N J, Wit A L. Disturbed connexin43 gap junction distribution correlates with the location of reentrant circuits in the epicardial border zone of healing canine infarcts that cause ventricular tachycardia. Circulation 1997; 95:988–996.

6. Spach M S, Barr R C, Johnson E A, et al. Cardiac extracellular potentials. Analysis of complex waveforms about the Purkinje networks in dogs. Circ Res 1973; 33:465–473.
7. Spach M S, Miller W T III, Miller-Jones E., Warren R B, and Barr R C. Extracellular potentials related to intracellular action potentials during impulse conduction in anisotropic canine cardiac muscle. Circ Res 1979; 45:188–204.
8. Spach M S, Miller W T III, Geselowitz D B, et al. The discontinuous nature of propagation in normal canine cardiac muscle. Evidence for recurrent discontinuities of intracellular resistance that affect the membrane currents. Circ Res 1981; 48:39–54.
9. Spach M S, Dolber P C. Relating extracellular potentials and their derivatives to anisotropic propagation at a microscopic level in human cardiac muscle. Evidence for electrical uncoupling of side to side fiber connections with increasing age. Circ Res 1986; 58:356–371.
10. Kienzle M G, Miller J, Falcone R A, Harken A, Josephson M E. Intraoperative endocardial mapping during sinus rhythm: relationship to site of origin of ventricular tachycardia. Circulation 1984; 70:957–965.
11. Miller J M, Harken A H, Hargrove W C, Josephson M E, Pattern of endocardial activation during sustained ventricular tachycardia. J Am Coll Cardiol 1985; 6:1280–1287.
12. Stevenson W G, Weiss J N, Wiener I, Rivitz S M, Nademanee K, Klitzner T, Yeatman L, Josephson M, Wohlgelernter D. Fractionated endocardial electrograms are associated with slow conduction in humans: evidence from pace-mapping J Am Coll Cardiol 1989 February; 13(2):369–376.
13. Wiener I, Mindich B, Pitchon R. Fragmented endocardial electrical activity in patients with ventricular tachycardia: a new guide to surgical therapy. Am Heart J. 1984; 107:86–90.
14. Shimizu A, Nozaki A, Rudy Y, Waldo A L. Characterization of double potentials in a functionally determined reentrant circuit. Multiplexing studies during interruption of atrial flutter in the canine pericarditis model. J of the American College of Cardiology 1993; 22:2022–2032.
15. Chinushi M, Aizawa Y, Kusano Y, Washizuka T, Shibata A. Evidence for slow conduction areas during pacing in patients with sinus rhythm, and their relation to the site of VT origin. Circulation 1994.
16. Schilling R J, Davies D W, Peters N S. Characteristics of sinus rhythm electrograms at sites of ablation of ventricular tachycardia relative to all other sites; a noncontact mapping study of the entire left ventricle. J Cardiovascular Electrophysiology 1998; 9:921–933.
17. Assadi M, Restivo M, Gough W B, el-Sherif N. Reentrant ventricular arrhythmias in the late myocardial infarction period: 17. Correlation of activation patterns of sinus and reentrant ventricular tachycardia. Am Heart J 1990; 119:1014–1024.
18. Scheinman M M, Ciaccio E J, Kassotis J, Sauberman R B, Coromilas J, Wit A L. Use of bipolar electrogram characteristics and activation pattern during sinus rhythm and ventricular pacing to predict the location of ventricular tachycardia reentrant circuits in a canine infarct model. Circulation 1995: (Abstract).
19. Ciaccio E J, Wit A L, Scheinman M M, Dunn S M, Akay Y, Coromilas J. Prediction of the location and time of spontaneous termination of reentrant ventricular tachycardia for radiofrequency catheter ablation. J Electrocardiol 1995; 28(Suppl):165–173.
20. Widrow B. The "rubber-mask" technique I. Pattern measurement and analysis. Pattern Recognition 1973; 5:175–197.
21. Ciaccio E J, Scheinman M M, Fridman V, Schmitt H, Coromilas J, Wit A L. A new approach to the analysis of electrogram features for the localization of reentrant circuits. J Cardiovasc Electrophysiology 1999: (accepted for publication).
22. El-Sherif N. The FIG. 8 model of reentrant excitation in the canine postinfarction heart. In: Zipes D P and Jalife J eds. Cardiac Electrophysiology. From Cell to Bedside. W.B. Saunders Co. Philadelphia Pa. 1995. pp 363–378.
23. Widrow B, Glover Jr. J R, McCool J M, Kaunitz J, Williams C S, Hearn R H, Zeidler J R, Dong Jr. E, and Goodlin R C. Adaptive noise canceling: principles and applications. Proc IEEE 1975; 63:1692–1716.
24. Scheaffer R L, Mendenhall W, Ott L. Elementary Survey Sampling, $2^{nd}$ ed. Duxbury Press, North Sciatuate Mass., 1979, p6.
25. Schalkoff R J. Pattern Recognition: Statistical, Structural, and Neural Approaches. J Wiley, New York, 1992.
26. Morady F, Frank R, Kou W H, Tonet J L, Nelson S D, Kounde S, De Buitleir M, Fontaine G. Identification and catheter ablation of a zone of slow conduction in the reentrant circuit of ventricular tachycardia in humans. J Am Coll Cardiol 1988 April; 11(4):775–82.
27. Wilber D J, Kopp D E, Glascock D N, Kinder C A, Kall J G Catheter ablation of the mitral isthmus for ventricular tachycardia associated with inferior infarction. Circulation 1995 December 15; 92(12):3481–9.
28. Sato M, Sakurai M, Yotsukura A, Betsuyaku T, Ito T, Yoshida I, Kitabatake A The efficacy of radiofrequency catheter ablation for the treatment of ventricular tachycardia associated with cardiomyopathy. Jpn Circ J 1997 January; 61(1):55–63.
29. Josephson M E, Horowitz L N, Farshidi A, Spielman S R, Michelson E L, Greenspan A M, Sustained ventricular tachycardia: evidence for protected localized reentry., Am J Cardiol 1978; 42:416–424.
30. Morady F, Frank R, Kou W H, Tonet J L, Nelson S D, Kounde S, De Buitleir M, Fontaine G. Identification and catheter ablation of a zone of slow conduction in the reentrant circuit of ventricular tachycardia in humans. J Am Coll Cardiol 1988; 11:775–782.
31. Chinushi M, Aizawa Y, Miyajima S, Funazaki T, Tamura M, Shibata A Proarrhythmic effects of antiarrhythmic drugs assessed by electrophysiologic study in recurrent sustained ventricular tachycardia. Jpn Circ J 1991; 55:133–141.
32. Aizawa Y, Niwano S, Chinushi M, Tamura M, Kusano Y, Miyajima T, Kitazawa H, Shibata A. Incidence and mechanism of interruption of reentrant ventricular tachycardia with rapid ventricular pacing. Circulation 1992; 85:589–595.
33. Habbab M A, el-Sherif N. Recordings from the slow zone of reentry during burst pacing versus programmed premature stimulation for initiation of reentrant ventricular tachycardia in patients with coronary artery disease. Am J Cardiol 1992; 70:211–217.
34. Stevenson W G, Sager P, Nademanee K, Hassan H, Middlekauff H R, Saxon L A, Wiener I. Identifying sites for catheter ablation of ventricular tachycardia. Herz 1992; 17:158–170.
35. Stevenson W G, Khan H, Sager P, Saxon L A, Middlekauff H R, Natterson P D, Weiner I. Identification of reentry circuit sites during catheter mapping and radiofrequency ablation of ventricular tachycardia late after myocardial infarction. Circulation 1993; 88:1647–1670.
36. Stevenson W G. Ventricular tachycardia after myocardial infarction: From Arrhythmia surgery to catheter ablation. J Cardiovasc Electrophys 1995; 6:942–950.

37. Okumura K, Yamabe H, Tsuchiya T, Tabuchi T, Iwasa A, Yasue H Characteristics of slow conduction zone demonstrated during entrainment of idiopathic ventricular tachycardia of left ventricular origin. Am J Cardiol 1996; 77:379–383.
38. Morady F, Kadish A, Rosenheck S, Calkins H, Kou W H, De Buitleir M, Sousa J. Concealed entrainment as a guide for catheter ablation of ventricular tachycardia in patients with prior myocardial infarction. J Am Coll Cardiol 1991; 17:678–689.
39. Aizawa Y, Kitazawa H, Washizuka T, Takahashi K, Shibata A. Conductive properties of the reentrant pathway of ventricular tachycardia during entrainment from outside and within the zone of slow conduction. Pacing Clin Electrophysiol 1995; 18:663–672.
40. Cao K, Gonska B D. Catheter ablation of incessant ventricular tachycardia: acute and long-term results. Eur Heart J1996; 17:756–763.
41. Stevenson W G, Harada T, Friedman P L, Sager P, Saxon L A. Preferential locations for critical reentry circuit sites causing ventricular tachycardia after inferior wall myocardial infarction. J Cardiovasc Electrophysiol 1997; 8:363–370.
42. Krishnan S C, Josephson M E. Mapping techniques and catheter ablation of ventricular tachycardia due to coronary artery disease. Arch Mal Coeur Vaiss 1998; 91 Spec No 1:21–26.
43. Agarwal J B, Naccarella F F, Weintraub W S, Helfant R H. Sinus rhythm mapping in healed experimental myocardial infarction: contrasting activation patterns for inducing ventricular tachycardia versus fibrillation. Am J Cardiol 1985; 55 (13 Pt 1):1601–1607.
44. Bourke J P, Campbell R W, Renzulli A, McComb J M, Cowan J C, Guzman F, Hilton C J. Surgery for ventricular tachycardia tachyarrhythmias based on fragmentation mapping in sinus rhythm alone. Eur J Cardiothorac Surgery 1989; 3:401–406.
45. Gonska B D, Cao K, Schaumann A, Dorszewski A, von zur Muhlen F, Kreuzer H. Catheter ablation of ventricular tachycardia in 136 patients with coronary artery disease: results and long-term follow-up. J Am Coll Cardiol 1994; 24:1506–1514.
46. Harada T, Stevenson W G, Kocovic D Z, Friedman P L. Catheter ablation of ventricular tachycardia after myocardial infarction: Relation of endocardial sinus rhythm late potentials to the reentry circuit. J Am Coll Cardiol 1997; 30:1015–1023.
47. Waspe L E, Bridman R, Kim S G, Matos J A, Johnston D R, Scavin G M, Fisher J D. Activation mapping in patients with coronary artery disease with multiple ventricular tachycardia configurations: occurrence and therapeutic implications of widely separate apparent sites of origin. J Am Coll Cardiol 1985; 5:1075–1086.
48. Downar E, Kimber S, Harris L, Mickleborough L, Sevaptsidis E, Masse S, Chen T C, Genga A. Endocardial mapping of ventricular tachycardia in the intact human heart. II. Evidence for multiuse reentry in a functional sheet of surviving myocardium. J American College Cardiology 1992; 20:869–878.
49. Downar E, Saito J, Doig J C, Sevaptsidis E, Masse S, Kimber S, Mickleborough L, Harris L. Endocardial mapping of ventricular tachycardia in the intact human ventricle. III. Evidence of multiuse reentry with spontaneous and induced block in portions of the reentrant path complex. J. American College Cardiology 1995; 25:1591–1600.
50. Luke R A, Saffitz J E. Remodeling of ventricular conduction pathways in healed canine infarct border zones. J Clinical Investigation 1991; 87:1594–1602.
51. Saffitz J E. Gap junctions: Functional effects of molecular structure and tissue distribution. Advances in Experimental Medicine & Biology 1997; 430:291–301.
52. Cardinal R, Vermeulen M, Shenasa M, Roberge F, Page P, Helie F, Savard P. Anisotropic conduction and functional dissociation of ischemic tissue during reentrant ventricular tachycardia in canine myocardial infarction. Circulation 1988; 77:1988.
53. Peters N S, Coromilas J, Hanna M S, Josephson M E, Costeas C, Wit A L. Characteristics of temporal and spatial excitable gap in anisotropic reentrant circuits causing sustained ventricular tachycardia. Circulation Research 1998; 82:279–293.
54. Smith J H, Green C R, Peters N S, Rothery S, Severs N J. Altered patterns of gap junction distribution in ischemic heart disease. An immunohistochemical study of human myocardium using laser scanning confocal microscopy. American J Pathology 1991; 139:801–821.
55. Sedlis S P. Mechanisms of ventricular arrhythmias in acute ischemia and reperfusion. Cardiovascular Clinics 1992; 22:3–18.
56. Holtz J. Myocardial hypertrophy after myocardial infarct: what is the significance of phenotype changes in cardiocytes? Herz 1993; 18 Suppl. 1:387–394.
57. Peters N S, Green C R, Poole-Wilson P A, Severs N J. Reduced content of connexin43 gap junctions in ventricular myocardium from hypertrophied and ischemic human hearts. Circulation 1993; 88:864–875.
58. Saffitz J E, Davis L M, Darrow B J, Kanter H L, Laing J G, Beyer E C. The molecular basis of anisotropy: role of gap junctions. J. Cardiovascular Electrophysiology 1995; 6:498–510.
59. Peters N S. Myocardial gap junction organization in ischemia and infarction. Microscopy Research & Technique 1995; 31:375–386.
60. Davis L M, Rodefeld M E, Green K, Beyer E C, Saffitz J E. Gap junction protein phenotypes of the human heart and conduction system. J. Cardiovascular Electrophysiology 1996; 7:382–383.
61. Peters N S. New insights into myocardial arrhythmogenesis: distribution of gap-junctional coupling in normal, ischaemic and hypertrophied human hearts. Clinical Science 1996; 90:447–452.
62. Kaprielian R R, Gunning M, Dupont E, Sheppard M N, Rithery S M, Underwood R, Pennell D J, Fox K, Pepper J, Poole-Wilson P A, Severs N J. Downregulation of immunodetectable connexin43 and decreased gap junction size in the pathogenesis of chronic hibernation in the human left ventricle. Circulation 1998; 7:651–660.
63. Steinbeck G. The pro-arrhythmic effects of anti-arrhythmic agents-theoretical and clinical aspects. Zeitschrift fur Kardiologie 1992; 81 Suppl. 4:139–143.
64. Spear J F, Moore E N. The importance of the electrophysiologic substrates in the development of venticular tachyarrhythmias. Puerto Rico Halth Sciences Journal. 1985: 4:73–78.
65. Verhueckx N A M, van der Elzen H C, Snijders F A M, van Gerwin P J. Disyal echo cancellation for base data transmission. IEEE Trans Acoust Speech Sig Proc 1979; ASSP-27:768–781.
66. El-Sherif N, Turitto G. High Resolution Electrocardiography. Futura Publishing Company, Mount Kisko, N.Y. 1992.
67. Davis L M, Rodefeld M E, Green K, Beyer E C, Saffitz J E. Gap junction protein phenotypes of the human heart and conduction system. J. Cardiovascular Electrophysiology. 1995; 6(10 Pt 1):813–822.

What is claimed is:

1. A method of using feature detection and localization (FDL) algorithms for identifying and localizing reentrant circuits from electrogram features in a heart of a subject comprising the steps of:
   a) using a contoured array of electrodes arranged in concentric circular patterns to obtain signals from the heart's surface to determine direction and velocity of an activating wavefront at the catheter location;
   b) obtaining and preprocessing analog electrogram signals, and then multiplexing and storing the signals in real time; and
   c) creating real-time maps and generating other textual information based on feature detection and localization (FDL) algorithms so as to thereby identify and localize reentrant circuits from electrogram features in the heart of the subject.

2. The method of claim 1 for quantifying dynamic, beat-to-beat changes in electrogram morphology.

3. The method of claim 2, wherein signal segments are adaptively matched for best overlap.

4. The method of claim 2 for quantifying the linear parameter of electrogram shape.

5. The method of claim 1, wherein the method is used for quantifying a piecewise linear parameter of electrogram shape.

6. The method of claim 1, wherein the method is used for quantifying a non-linear parameter of electrogram shape.

7. The method of claim 1, wherein mean square error or other criteria is used for adaption of weights.

8. The method of claim 7, wherein the mean square error or other criteria measures cycle-to-cycle changes in intrinsic electrogram shape.

9. The method of claim 1, wherein each electrogram on each cardiac cycle is compared to a reference electrogram or template electrogram.

10. The method of claim 9, wherein the method is used to obtain information about changes in electrogram morphology which occur over multiple cardiac cycles from one cardiac cycle to the next cardiac cycle.

11. The method of claim 1, wherein functional lines of block are located using an ATM algorithm.

12. The method of claim 1 to locate reentrant circuits for surgical incision or catheter ablation in a subject with ventricular tachycardia.

13. The method of claim 1, wherein reentrant circuit features are identified and located for catheter ablation of ventricular tachycardia without the necessity for recording from a large number of sites and without constructing activation maps.

14. The method of claim 13, wherein a region of greatest increase of a PLATM duration parameter when tachycardia cycle length increases resides at a location where slow conduction occurs in a central common pathway of a reentrant circuit.

15. The method of claim 13, wherein a region of greatest decrease of a PLATM duration parameter when tachycardia cycle length decreases resides at a location where slow conduction occurs in the central common pathway of a reentrant circuit.

16. The method of claim 14 or 15, wherein the method is used to update a location of an ablation catheter based on far-field electrogram deflections.

17. The method of claim 16, wherein a PLATM phase shift parameter is used to determine time of activation of the zone of slow conduction with respect to a local activation time at the position of the catheter.

18. The method of claim 17, wherein a model is used to convert the time of activation into a direction and distance from the current position of the catheter to the zone of slow conduction.

19. The method of claim 13 wherein an NATM filter coefficient is used to distinguish activation occurring inside of a central common pathway from activation occurring outside of a central common pathway.

20. The method of claim 19 wherein waveforms are compared at different cycle lengths to determine changes in an NATM filter coefficient.

21. The method of claim 20, wherein the method is used to update the location of an ablation catheter based on electrogram far-field directions.

22. The method of claim 13, wherein a concentric circular multielectrode ring and a conduction velocity (CV) algorithm are used to determine wavefront speed and direction at the location of the catheter tip.

23. The method of claim 22, wherein the direction of wavefront propagation is calculated based on the conduction velocity algorithm using the maximum difference in activation time of any two or more electrodes.

24. The method of claim 23, wherein the direction of the block lines with respect to the catheter tip are perpendicular to the direction of wavefront propagation when the catheter resides within the central common pathway at the slow conduction zone.

25. The method of claim 23, wherein conduction velocity of an activating wavefront is determined by dividing the maximum difference or maximum average difference in activation time of any two or more electrodes into the distance or average distande between those electrodes.

26. The method of claim 13, wherein the center of the narrowest width of the central common pathway of reentrant circuits is determined using 5–500 ATM weight variability peaks.

27. The method of claim 26, wherein the center of mass of the highest 2–400 variance peaks is determined, thereby approximating the center of the narrowest central common pathway width location.

28. The method of claim 26, wherein the center of mass of an average of all 5–500 variance peaks from highest to lowest is determined, thereby approximating the center of the narrowest central common pathway width location.

29. The method of claim 1, wherein ablation of a central common pathway between lines of functional block at a zone of slow conduction prevents tachycardia.

30. The method of claim 4, wherein the linear parameter of electrogram shape is scale.

31. The method of claim 30, wherein the scale is amplitude.

32. The method of claim 30, wherein the scale is duration.

33. The method of claim 4, wherein the linear parameter is shift.

34. The method of claim 33, wherein the shift is average baseline.

35. The method of claim 33, wherein the shift is phase lag.

36. The method of claim 4, wherein the linear parameters are weighted by ramp function, sigmoidal function or step function in combination with uniform weighting.

37. The method of claim 5, wherein the piecewise linear parameter is scale.

38. The method of claim 37, wherein the scale is amplitude.

39. The method of claim 37, wherein the scale is duration.

40. The method of claim 5, wherein the piecewise linear parameter is shift.

41. The method of claim 40, wherein the shift is average baseline.

42. The method of claim 40, wherein the shift is phase lag.

43. The method of claim 5, wherein the piecewise linear parameter is weighted by ramp function, sigmoidal function, or step function in combination with uniform weighting.

44. The method of claim 6, wherein the non-linear parameter is a low pass filter coefficient.

45. The method of claim 6, wherein the non-linear parameter a high pass filter coefficient.

46. The method of claim 6, wherein the non-linear parameter is a notch pass filter coefficient.

47. The method of claim 6, wherein the non-linear parameter is a bandpass pass filter coefficient.

48. The method of claim 6, wherein the non-linear parameter is an exponential or other nonlinear coefficient.

49. The method of claim 6, wherein the non-linear parameter is weighted by ramp function, sigmoidal function or step function in combination with uniform weighting.

50. The method of claim 9, wherein the reference electrogram or template electrogram is obtained from a representative cycle.

51. The method of claim 9, wherein the reference electrogram or template electrogram is obtained from a combination of multiple cycles.

52. The method of claim 10, which uses a differential steepest descent method or other adaptive method to compute weight update.

53. The method of claim 52, wherein magnitude and direction for weight adjustment are determined by calculating a derivative or other function of error based on finite difference changes or other changes in weighting.

54. The method of claim 53, wherein the method minimizes a misadjustment of weight update.

55. The method of claim 53, wherein a convergence coefficient is optimized so as to minimize misadjustment of weight update.

56. The method of claim 55, wherein a convergence coefficient is incremented up or down so as to minimize mean square error or other error function during weight update.

57. The method of claim 53, wherein the number of data samples or length of segment are maximized so as to minimize misadjustment of weight update.

58. The method of claim 57, wherein maximum length of segment is between 50 milliseconds to 1000 milliseconds.

59. The method of claim 53, wherein finite difference is optimized so as to minimize misadjustment of weight update.

60. The method of claim 59, wherein finite difference is incremented up or down so as to minimize mean square error or other error function during weight update.

61. The method of claim 11, wherein functional lines of block in reentrant circuits are located by analyzing ATM variances or other weight variabilities from data obtained during sustained monomorphic ventricular tachycardia.

62. The method of claim 11, wherein functional lines of block in reentrant circuits are located by analyzing ATM variances or other weight variabilities from data obtained during unsustained monomorphic ventricular tachycardia.

63. The method of claim 11, wherein functional lines of block in reentrant circuits are located by analyzing ATM variances or other weight variabilities from data obtained during polymorphic ventricular tachycardia.

64. The method of claim 11, wherein functional lines of block in reentrant circuits are located by analyzing ATM variances or other weight variabilities from data obtained during sinus rhythm.

65. The method of claim 11, wherein functional lines of block in reentrant circuits are located by analyzing ATM variances or other weight variabilities from data obtained during ventricular pacing during sinus rhythm.

66. The method of claim 11, wherein functional lines of block in reentrant circuits are located by analyzing ATM variances or other weight variabilities from data obtained during pacing during ventricular tachycardia.

67. The method of claim 11, wherein analysis is performed by computer processing.

68. The method of claim 1, wherein regions of greatest variance of ATM parameters are adjacent to the location of functional lines of block which form boundaries of the central common pathway in reentrant circuits.

69. The method of claim 68, wherein a combination of variances for sites with low variance is used as a threshold.

70. The method of claim 13 wherein changes in a PLATM parameter when tachycardia cycle length changes reside at a location where slow conduction occurs in the central common pathway of a reentrant circuit.

71. The system of claim 70, wherein the PLATM parameter is duration, phase lag, amplitude or average baseline.

72. The method of claim 16, wherein a PLATM duration parameter is used to determine time of activation of a zone slow conduction with respect to a current position of the catheter.

73. The method of claim 72, wherein a model is used to convert time of activation into a direction and distance from a current position of the catheter to the zone of slow conduction.

74. The method of claim 73, wherein a location of the catheter tip can be directed toward a location of the optimal site to ablate the heart based on distance from the catheter tip to the slow conduction zone (SCZ) proximal and distal borders.

75. The method of claim 13, wherein a slow conduction zone in reentrant circuits can be located by analyzing PLATM parameters from data obtained during unsustained monomorphic ventricular tachycardia.

76. The method of claim 13, wherein a slow conduction zone in reentrant circuits can be located by analyzing PLATM parameters from data obtained during polymorphic ventricular tachycardia.

77. The method of claim 13, wherein a slow conduction zone in reentrant circuits can be located by analyzing PLATM parameters from data obtained during sinus rhythm.

78. The method of claim 13, wherein a slow conduction zone in reentrant circuits can be located by analyzing PLATM parameters from data obtained during ventricular pacing during sinus rhythm.

79. The method of claim 13, wherein a slow conduction zone in reentrant circuits can be located by analyzing PLATM parameters from data obtained during pacing during ventricular tachycardia.

80. The method of claim 13, wherein analysis is performed by computer processing.

81. The method of claim 21, wherein the catheter tip location is directed toward an optimal site to ablate the heart based on a distance from the catheter tip to the central common pathway entrance and exit.

82. The method of claim 21, wherein an NATM filter coefficient change when cycle length changes is used to determine time of activation of the borders of the central common pathway's entrance and exit with regard to local activation time at the portion of the catheter.

83. The method of claim 82, wherein a model is used to determine distance from the local site to the central common pathway's entrance and exit.

84. The method of claim 83, wherein the length of the central common pathway's length and the length of the bounding block lines are determined based on the distances from the catheter tip to the central common pathway entrance and exit.

85. The method of claim 84, wherein the central common pathway's location and length and bounding block lines' length are determined by analyzing NATM coefficients from data obtained during sustained monomorphic ventricular tachycardia.

86. The method of claim 84, wherein the central common pathway's location and bounding block lines' length are determined by analyzing NATM coefficients from data obtained during unsustained monomorphic ventricular tachycardia.

87. The method of claim 84, wherein the central common pathway's location and length and bounding block lines' length are determined by analyzing NATM coefficients from data obtained during polymorphic ventricular tachycardia.

88. The method of claim 84, wherein the central common pathway's location and length and bounding block lines' length are determined by analyzing NATM coefficients from data obtained during sinus rhythm.

89. The method of claim 84, wherein the central common pathway's location and length and bounding block lines' length are determined by analyzing NATM coefficients from data obtained during ventricular pacing during sinus rhythm.

90. The method of claim 84, wherein the central common pathway's location and length and bounding block lines' length are determined by analyzing ATM variances or other weight variabilities from data obtained during ventricular pacing during ventricular tachycardia.

91. The method of claim 26, wherein a narrowest central common pathway width location can be located by using center of mass data obtained during sustained monomorphic ventricular tachycardia.

92. The method of claim 26, wherein a narrowest central common pathway width location can be located by using center of mass data obtained during polymorphic ventricular tachycardia.

93. The method of claim 26, wherein a narrowest central common pathway width location can be located by using center of mass data obtained during sinus rhythm.

94. The method of claim 26, wherein center of mass width location can be located by using center of mass data obtained during ventricular pacing during sinus rhythm.

95. The method of claim 26, wherein center of mass width location can be located by using center of mass data obtained during ventricular pacing during ventricular tachycardia.

96. The method of claim 1, further comprising ablating a heart to stop ventricular tachycardia when pattern of reentry is that of a single loop or of multiple loops.

97. The method of claim 1 further comprising ablating a heart to stop ventricular tachycardia when lines of block around which activating wavefront traverses are anatomical, partially anatomical, or functional.

98. The method of claim 1 further comprising ablating a heart to stop ventricular tachycardia when pattern of reentry is intramural or transmural.

99. The method of claim 1 wherein the method is used to pinpoint sites or specific areas for drug delivery.

100. The method of claim 1 wherein the method is used to detect and localize pathologic conditions in a heart, brain, lung, gastrointestinal system, musculoskeletal system or other system.

101. The method of claim 1, wherein the real time maps and other textual information are displayed on a computer screen.

102. A system for identifying and localizing reentrant circuits from electrogram features in a heart of a subject using feature detection and localization (FDL) algorithms which comprises:
   a) a multipolar ring electrode catheter which uses a contoured array of electrodes arranged in concentric circular patterns to obtain signals from the heart's surface to determine the speed and direction and velocity of an activating wavefront at the catheter location;
   b) a data acquisition subsystem for obtaining and preprocessing analog electrogram signals, and for multiplexing and storing the signal in real-time, either in analog or digital form;
   c) a processing unit comprising software and hardware for using multiple electrode signals, and feature detection and localization (FDL) algorithms; and
   d) a display/guidance subsystem for creating real-time maps and generating other textual information based on reentrant circuit features algorithms.

103. The system of claim 102, wherein the multipolar ring electrode catheter comprises electrodes attached to wires at a tip of the catheter for recording electrogram signals and for ablating the heart from any of the electrodes.

104. The system of claim 103, wherein the wires are insulated.

105. The system of claim 103, wherein the wires are shielded.

106. The system of claim 103, wherein the wires are thin.

107. The system of claim 102, wherein the multipolar ring electrode catheter comprises a configuration of electrodes in concentric circular patterns.

108. The system of claim 107, wherein the configuration of electrodes in concentric circular patterns are located at a tip of the catheter.

109. The system of claim 108, wherein the electrodes record electrogram signals and ablate the heart with radiofrequency or other energy.

110. The system of claim 102, wherein the multipolar ring electrode catheter comprises an electrode array.

111. The system of claim 110, wherein the electrode array is conical-shaped.

112. The system of claim 110, wherein the electrode array is capable of being folded.

113. The system of claim 112 wherein the electrode array is capable of being folded in a fan-like folding action.

114. The system of claim 112, wherein the electrode array is folded when located in a human artery.

115. The system of claim 112, wherein the electrode array is opened into a conical-shape when located in a ventricular cavity of the heart so as to fit the contour of the heart.

116. The system of claim 102, wherein the multipolar ring electrode catheter comprises a catheter shell.

117. The system of claim 116, wherein the catheter shell is flexible.

118. The system of claim 116, wherein the catheter shell contains wires.

119. The system of claim 118, wherein the wires are used to record electrograms and to ablate the heart.

120. The system of claim 102, wherein the multipolar ring electrode catheter comprises a terminal mount.

121. The system of claim 120, wherein the terminal mount is used to connect and disconnect the catheter at its end which is proximal to the data acquisition subsystem.

122. The system of claim 102, wherein the data acquisition subsystem comprises circuitry.

123. The system of claim 122, wherein the circuitry amplifies signals so as to thereby reduce noise pickup.

124. The system of claim 122, wherein the circuitry increases voltage resolution of the digitized signals.

125. The system of claim 122, wherein the circuitry low pass filters signals so as to thereby prevent aliasing during digitization.

126. The system of claim 122, wherein the circuitry high pass filters signals so as to prevent buildup of bias voltage and prevent motion artifacts.

127. The system of claim 122, wherein the circuitry mutiplexes and stores electrogram signals.

128. The system of claim 127, wherein the electrogram signals are stored in analog form.

129. The system of claim 127, wherein the electrogram signals are stored in digital form.

130. The system of claim 102, wherein the processing unit comprises algorithms for identification and location of reentrant circuit features.

131. The system of claim 102, wherein the algorithms are hardwired using analog circuitry for serial or parallel processing.

132. The system of claim 102, wherein the algorithms are hardwired using integrated circuits for serial or parallel processing.

133. The system of claim 102, wherein the algorithms are downloaded to programmable logic array integrated circuits for serial or parallel processing.

134. The system of claim 102, wherein the algorithms are written in software code for serial or parallel processing using a microprocessor or parallel processing using multiple microprocessors.

135. The system of claim 102, wherein the display/guidance subsystem displays wavefront, speed, direction and conduction velocity.

136. The system of claim 135, wherein the wavefront, speed, direction and conduction velocity are determined based on electrogram signals obtained from the multipolar electrode array and the conduction velocity algorithm.

137. The system of claim 136, wherein location of block lines is determined based on measurements made using an ATM algorithm.

138. The system of claim 136, wherein direction of the slow conduction zone with respect to catheter location is determined based on measurements made using a PLATM algorithm.

139. The system of claim 136, wherein distance to proximal and distal borders of the slow conduction zone with respect to the catheter location is determined.

140. The system of claim 136, wherein the central common pathway's entrance and exit are located based on measurements made using an NATM algorithm.

141. The system of claim 136, wherein lengths of bounding functional line of block are determined based on measurements made using an NATM algorithm.

142. The system of claim 136, for locating a narrowed width of the central common pathway based on a center of mass algorithm.

143. The system of claim 136, which further comprises a system of symbols which den te features of the reentrant circuit on a real-time display map.

144. The system of claim 143, wherein the system of symbols comprises shaded and extured shapes.

145. The system of claim 136, which further comprises a system of symbols which denote distance and directional information pertaining to a location of reentrant circuit features with respect to a location of the catheter on a real-time display map.

146. The system of claim 145, wherein the system of symbols comprises arrows and angles.

147. The system of claim 136, wherein maps and textual information are updated in near-real time based on reentrant circuit feature algorithms and on new data obtained at each new site at which the catheter tip is positioned.

148. The system of claim 147, wherein the maps and textual information are updated on the display screen.

149. The system of claim 102 for ablating the heart to stop ventricular tachycardia when the pattern of reentry is a single loop or multiple loops.

150. The system of claim 102 for ablating the heart to stop ventricular tachycardia when lines of block around which an activating wavefront traverses are anatomical.

151. The system of claim 102 which uses sensors other than electrodes selected from the group consisting of magnetometers, microphones, pressure transducers, thermistors, charge-coupled diode arrays, or gas analyzers.

152. The system of claim 151, wherein the sensors obtain signal or image information for detection and localization of pathologic conditions in the heart, brain, lung, gastroinestinal system or musculoskeletal system.

153. The system of claim 102, wherein the real time maps and other textual information are displayed on a computer screen.

154. The system of claim 153, wherein the computer screen is touch sensitive.

155. The system of claim 102, for ablating the heart to stop ventricular tachycardia when the pattern of reentry is intramural or transmural.

156. The system of claim 102 for pinpointing sites or specific areas for drug delivery.

157. The system of claim 102 used to detect and localize pathologic conditions in the heart, brain, lung, gastrointestinal system, musculoskeletal system and other systems.

\* \* \* \* \*